US007452908B2

(12) United States Patent
Sagara et al.

(10) Patent No.: US 7,452,908 B2
(45) Date of Patent: *Nov. 18, 2008

(54) AMIDE DERIVATIVES

(75) Inventors: Yufu Sagara, Tsukuba (JP); Minaho Uchiyama, Tsukuba (JP); Akira Naya, Tsukuba (JP); Toshifumi Kimura, Tsukuba (JP); Tomoshige Numazawa, Tsukuba (JP); Toru Fujikawa, Tsukuba (JP); Norikazu Otake, Tsukuba (JP); Kazuhito Noguchi, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 456 days.

This patent is subject to a terminal disclaimer.

(21) Appl. No.: 10/838,340

(22) Filed: May 5, 2004

(65) Prior Publication Data

US 2004/0204369 A1    Oct. 14, 2004

Related U.S. Application Data

(62) Division of application No. 10/031,716, filed as application No. PCT/JP00/04762 on Jul. 14, 2000, now Pat. No. 6,809,108.

(30) Foreign Application Priority Data

Jul. 23, 1999  (JP) ................................. 99/209292
Nov. 29, 1999  (JP) ................................. 99/338617

(51) Int. Cl.
*A61K 31/445*  (2006.01)
*C07D 211/32*  (2006.01)

(52) U.S. Cl. .................................... 514/331; 546/234

(58) Field of Classification Search ................. 514/326, 514/317; 546/208, 229
See application file for complete search history.

(56) References Cited

U.S. PATENT DOCUMENTS 5,750,540 A    5/1998  Tsuchiya et al.

FOREIGN PATENT DOCUMENTS

| EP | 747355 | * 11/1996 |
| EP | 747355 | 12/1996 |
| EP | 823423 | 2/1998 |
| WO | 95/06635 | 3/1995 |

OTHER PUBLICATIONS

Silverman "The organic chemistry of drug design . . . " p. 71-73 (1993).*
Pratesi et al. "Molecular properties . . . " CA 63:62596 (1965).*
Katzung, Basic and Clinical Pharmacology, Fourth Edition, pp. 83-92 (1989).
Doods, Drug News & Perspective, 5(6), pp. 345-362 (1992).

* cited by examiner

*Primary Examiner*—Celia Chang
(74) *Attorney, Agent, or Firm*—Wenderoth, Lind & Ponack, L.L.P.

(57) ABSTRACT

This invention relates to compounds which are represented by the general formula [I]

$$Ar^1-\underset{Ar^3}{\underset{|}{\overset{Ar^2}{\overset{|}{C}}}}-\overset{R^1}{\underset{|}{C}}H-\overset{O}{\overset{\|}{C}}-\overset{R^2}{\underset{|}{N}}-\overset{R^3}{\underset{|}{C}}H-(CH_2)_k-X-\overset{R^4}{\underset{|}{Y}}-$$

$$-\overset{R^5}{\underset{|}{C}}H-(CH_2)_m-\overset{O}{\overset{\|}{C}}-\overset{H}{\underset{|}{N}}-(CH_2)_n-A$$

[in which A stands for a group of the following formula [$a_o$] or [$b_o$]]

[$a_o$]

[$b_o$]

$Ar^1$, $Ar^2$ and $Ar^3$ stand for optionally substituted phenyl; k stands for 0 or 1; m, n and s stand for 0, 1 or 2; $R^1$ stands for hydrogen or optionally substituted lower alkyl; $R^2$, $R^3$, $R^4$ and $R^5$ either stand for hydrogen or optionally substituted lower alkyl, or $R^2$ and $R^3$, or $R^4$ and $R^5$ together stand for trimethylene and the like; $R^{60}$ stands for hydrogen, alkyl, or the like; $R^{61}$ and $R^{71}$ either stand for alkyl and the like, or together stand for trimethylene and the like; X stands for carbonyl or methylene; Y stands for nitrogen or methine; and $Q^-$ stands for anion], and the like.

The compounds of the invention exhibit selective antagonism to muscarinic $M_3$ receptors, and therefore are useful as safe and effective agents showing little side effect, for treating diseases of the respiratory, urinary and digestive systems.

14 Claims, No Drawings

AMIDE DERIVATIVES

This is a divisional of Ser. No. 10/031,716, filed Mar. 26, 2002, now U.S. Pat. No. 6,809,108 which is a 371 of PCT/JP00/04762, filed Jul. 14, 2000.

TECHNICAL FIELD

This invention relates to novel amide derivatives, processes for preparing them, pharmaceutics containing them and their use as medicines, especially in the treatment of various diseases of the respiratory, urinary and digestive systems.

BACKGROUND ART

Antagonism to muscarinic receptors are known to cause bronchodilation, gastrointestinal hypanakinesis, gastric hyposecretion, dry mouth, mydriasis, suppression of bladder contraction, hypohidrosis, tachycardia and the like [cf. *Basic and Clinical Pharmacology*, 4th ed., APPLETON & LANGE, pp. 83-92 (1989) and *Drug News & Perspective*, 5(6), pp. 345-352 (1992)].

It has recently been made clear that there are at least three subtypes of muscarinic receptors; $M_1$ receptors being present mainly in the brain; $M_2$ receptors, mainly in the heart, and $M_3$ receptors, on smooth muscles and glandular tissues. Whereas, all of the large number-of compounds heretofore known to exhibit antagonism to muscarinic receptors non-selectively antagonize the three subtypes of muscarinic receptors. Consequently, attempts to use these compounds as therapeutic or prophylactic agents for diseases of the respiratory system have caused undesirable side effects such as dry mouth, nausea and mydriasis. Still in addition, particularly serious side effects associated with the central nervous system, such as dementia, attributable to $M_1$ receptors and those associated with the heart, such as tachycardia mediated by $M_2$ receptors pose problems and their solution has been strongly in demand.

DISCLOSURE OF THE INVENTION

An object of the present invention is to provide treating agents of diseases associated with muscarinic $M_3$ receptors, said agents exhibiting highly selective antagonism to muscarinic $M_3$ receptors and little side effects, and being safe and effective.

We have discovered that those compounds which are represented by the following general formula [I]

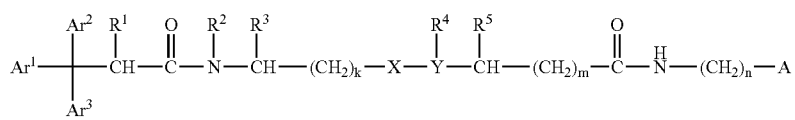

[in which A stands for a group of the following formula [$a_o$] or [$b_o$]

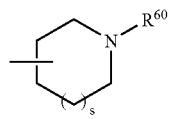

-continued

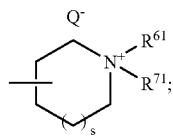

$Ar^1$, $Ar^2$ and $Ar^3$ each independently stands for optionally substituted phenyl, the substituent being selected from the group consisting of halogen, hydroxyl, lower alkyl, lower alkenyl, lower alkoxy, carbamoyl, lower alkylcarbamoyl and di-lower alkylcarbamoyl; k means 0 or 1; m, n and s each independently means 0, 1 or 2; $R^1$ stands for hydrogen or optionally substituted lower alkyl, the substituent being selected from the group consisting of hydroxyl, amino, carbamoyl, lower alkylcarbamoyl, di-lower alkylcarbamoyl and imidazolyl; $R^2$, $R^3$, $R^4$ and $R^5$ each independently stands for hydrogen or optionally substituted lower alkyl, the substituent being selected from the group consisting of hydroxyl, amino, carbamoyl, lower alkylcarbamoyl, di-lower alkylcarbamoyl and imidazolyl, or $R^2$ and $R^3$, or $R^4$ and $R^5$, may together stand for, independently of each other, optionally substituted trimethylene, propenylene, tetramethylene or 2-butenylene group, the substituent being selected from the group consisting of oxo, hydroxyl, amino, lower alkoxy, lower alkanoyloxy, lower alkylamino, di-lower alkylamino, (imino-lower alkyl)amino, lower alkanoylamino, lower alkoxycarbonylamino, (lower alkylcarbamoyl)amino, lower alkylsulfonylamino, guanidino, lower alkoxycarbonyl, carbamoyl, lower alkylcarbamoyl, di-lower alkylcarbamoyl, imidazolyl and a group represented by —$R^7$, $R^7$ standing for optionally substituted lower alkyl, the substituent being selected from the group consisting of hydroxyl, amino, carbamoyl, lower alkylcarbamoyl di-lower alkylcarbamoyl lower alkoxycarbonyl and imidazolyl; $R^{60}$ stands for hydrogen, $C_1$-$C_{10}$ alkyl lower alkenyl, cycloalkyl, cycloalkyl-lower alkyl whose ring portion may be substituted with lower alkyl, cycloalkenyl-lower alkyl or aralkyl; $R^{61}$ and $R^{71}$ each independently stands for $C_1$-$C_{10}$ alkyl, lower alkenyl, cycloalkyl, cycloalkyl-lower alkyl whose ring portion may be substituted with lower alkyl, cycloalkenyl-lower alkyl or aralkyl, or $R^{61}$ and $R^{71}$ may together stand for optionally substituted trimethylene, tetramethylene, 2-butenylene, pentamethylene, 3-oxapentamethylene or 2,3-epoxytetramethylene group, the substituent being selected from the group consisting of oxo, hydroxyl, lower alkyl and lower alkoxy; X stands for carbonyl or methylene; Y stands for nitrogen or methine; and $Q^-$ stands for anion]

exhibit highly selective antagonism to muscarinic $M_3$ receptors, little side effect and high safety, and are very useful for treating various diseases which are associated with muscarinic $M_3$ receptors, eg., such respiratory diseases as chronic obstructive pulmonary diseases, chronic bronchitis, asthma, chronic respiratory tract obstruction, fibroid lung, pulmonary emphysema and rhinitis; digestive diseases such as irritable bowel syndrome, convulsive colitis, gastroduodental ulcer, convulsion or hyperanakinesia of digestive tract, diverticulitis and pain accompanying contraction of smooth muscles of the digestive system; urinary diseases accompanied by dysuria like urinary incontinence, urgency and pollakiuria in nervous pollakiuria, neurogenic bladder, nocturnal enuresis, unstable bladder, cystospasm and chronic cystisis; and motion sickness; and have completed the present invention.

The present invention relates to the compounds represented by above general formula [I] or salts thereof, processes for their preparation and their use.

Hereafterthe invention is explained in further details, in which the terms used mean the following.

"Halogen" means fluorine, chlorine, bromine and iodine atoms.

"Lower alkyl" means $C_1$-$C_6$ linear or branched alkyl groups, examples of which include methyl, ethyl, propyl, isopropyl, butyl, isobutyl, sec-butyl, tert-butyl, pentyl, isopentyl, hexyl and isohexyl groups.

"Lower alkenyl" means $C_2$-$C_6$ linear or branched alkenyl groups, examples of which include vinyl, 1-propenyl, 2-propenyl isopropenyl, 3-butenyl, 2-butenyl, 1-butenyl, 1-methyl-2-propenyl, 1-methyl-1-propenyl, 1-ethyl-l-ethenyl, 2-methyl-2-propenyl, 2-methyl-1-propenyl, 3-methyl-2-butenyl and 4-pentenyl groups.

"Lower alkoxy" means $C_1$-$C_6$ linear or branched alkoxy groups, examples of which include methoxy, ethoxy, propoxy, isopropoxy, butoxy, sec-butoxy, isobutoxy, tert-butoxy, pentyloxy, isopentyloxy, hexyloxy and isohexyloxy groups.

"Lower alkylcarbamoyl" means carbamoyl groups which are mono-substituted with said lower alkyl groups, examples of which include methylcarbamoyl, ethylcarbamoyl, propylcarbamoyl, isopropylcarbamoyl butylcarbamoyl sec-butylcarbamoyl and tert-butylcarbamoyl groups.

"Di-lower alkylcarbamoyl" means carbamoyl groups which are di-substituted with said lower alkyl groups, examples of which include dimethylcarbamoyl, diethylcarbamoyl, ethylmethylcarbamoyl, dipropylcarbamoyl, methylpropylcarbamoyl and di-isopropyl-carbamoyl groups.

"Lower alkylamino" means amino groups which are mono-substituted with said lower alkyl groups, examples of which include methylamino, ethylamino, propylamino, isopropylamino, butylamino, sec-butylamino and tert-butylamino groups.

"Di-lower alkylamino" means amino groups which are di-substituted with said lower alkyl groups, examples of which include dimethylamino, diethylamino, ethylmethylamino, dipropylamino, methylpropylamino and di-isopropylamino groups.

"Imino-lower alkyl" means said lower alkyl groups which are mono-substituted with imino group, examples of which include formimidoyl, acetimidoyl, propanimidoyl, butanimidoyl, pentanimidoyl and hexanimidoyl groups.

"(Imino-lower alkyl) amino" means amino groups which are mono-substituted with said imino-lower alkyl groups, examples of which include formimidoylamino, acetimidoylamino, propanimidoylamino, butanimidoylamino, pentanimidoylamino and hexanimidoylamino groups.

"Lower alkanoyl" means $C_1$-$C_6$ linear or branched alkanoyl groups, examples of which include formyl, acetyl, propionyl, butyryl, isobutyryl, valeryl, isovaleryl and pivaloyl groups.

"Lower alkanoyloxy" means alkanoyloxy groups having said lower alkanoyl groups, examples of which include acetoxy, propionyloxy, butyryloxy, isobutyryloxy, valeryloxy, isovaleryloxy and pivaloyloxy groups.

"Lower alkanoylamino" means amino groups which are mono-substituted with said lower alkanoyl groups, examples of which include formylamino, acetylamino, propionylamino, butyrylamino, isobutyrylamino, valerylamino, isovalerylamino and pivaloylamino groups.

"(Lower alkylcarbamoyl) amino" means amino groups which are mono-substituted with said lower alkylcarbamoyl groups, examples of which include (methylcarbamoyl)amino, (ethylcarbamoyl)amino, (propylcarbamoyl)amino, (isopropylcarbamoyl)amino, (butylcarbamoyl)amino, (sec-butylcarbamoyl)amino and (tert-butylcarbamoyl)amino groups.

"Lower alkylsulfonyl" means alkylsulfonyl groups having said lower alkyl groups, examples of which include methylsulfonyl, ethylsulfonyl, propylsulfonyl, isopropylsulfonyl, butylsulfonyl, sec-butylsulfonyl and tert-butylsulfonyl groups.

"Lower alkylsulfonylamino" means amino groups which are mono-substituted with said lower alkylsulfonyl groups, examples of which include methylsulfonylamino, ethylsulfonylamino, propylsulfonylamino, isopropylsulfonylamino, butylsulfonylamino, sec-butylsulfonylamino and tert-butylsulfonylamino groups.

"Lower alkoxycarbonyl" means alkoxycarbonyl groups having said lower alkoxy groups, examples of which include methoxycarbonyl, ethoxycarbonyl, propoxycarbonyl, isopropoxycarbonyl butoxycarbonyl, isobutoxycarbonyl, tert-butoxycarbonyl and pentyloxycarbonyl groups.

"Lower alkoxycarbonylamino" means amino groups which are mono-substituted with said lower alkoxycarbonyl groups, examples of which include methoxycarbonylamino, ethoxycarbonylamino, propoxycarbonylamino, isopropoxycarbonylamino, butoxycarbonylamino, isobutoxycarbonylamino, tert-butoxycarbonylamino and pentyloxycarbonylamino groups.

"$C_1$-$C_{10}$ alkyl" means $C_1$-$C_{10}$ linear or branched alkyl groups, examples of which includes, besides those earlier exemplified lower alkyl groups, 2-methylbutyl, 2-ethylbutyl, 2-methylpentyl, heptyl, octyl, nonyl and decyl groups.

"Cycloalkyl" means $C_3$-$C_{10}$ cycloalkyl groups, examples of which include cyclopropyl, cyclobutyl, cyclopentyl, cyclohexyl, cycloheptyl, cyclooctyl, cyclononyl and cyclodecyl groups.

"Cycloalkyl-lower alkyl" means said lower alkyl groups having above cycloalkyl groups, examples of which include cyclopropylmethyl, 2-cyclopropylethyl, cyclobutylmethyl, cyclopentylmethyl, 1-cyclopentylethyl, 2-cyclopentylethyl, cyclohexylmethyl, 1-cyclohexylethyl, 2-cyclohexylethyl, cycloheptylmethyl and cyclooctylmethyl groups.

"Cycloalkyl-lower alkyl whose ring portion may be substituted with lower alkyl" means either above cycloalkyl-lower alkyl groups or said cycloalkyl-lower alkyl groups having one, two or more, preferably one or two same or different, earlier named lower alkyl groups at the optional, substitutable position or positions on the cycloalkyl group, examples of which include, besides above-exemplified cycloalkyl-lower alkyl groups, 1-(1-methylcyclopropyl)ethyl, 2-(1-methylcyclopropyl)ethyl, (2,2-dimethylcyclopentyl)methyl, 1-(2,2-dimethylcyclopentyl)ethyl and 2-(2,2-dimethylcyclopentyl) ethyl groups.

"Cycloalkenyl" means $C_3$-$C_{10}$ cycloalkenyl groups, examples of which include cyclopropenyl, cyclobutenyl, cyclopentenyl, cyclohexenyl, cycloheptenyl, cyclooctenyl, cyclononenyl and cyclodecenyl groups.

"Cycloalkenyl-lower alkyl" means said lower alkyl groups having said cycloalkenyl groups, examples of which include cyclopropenylmethyl, cyclobutenylmethyl, cyclopentenylmethyl, cyclohexenylmethyl, cycloheptenylmethyl, cyclooctenylmethyl, cyclononenylmethyl and cyclodecenylmethyl groups.

"Aralkyl" means said lower alkyl groups having aryl groups such as phenyl, naphthyl or anthryl, examples of which include benzyl, 1-phenylethyl, 2-phenylethyl, 1-naphthylmethyl and 2-naphthylmethyl groups.

"Anion" means those forming a pair with ammonium ions on the compounds of the present invention, which electrically neutralize said compounds. While they are not subject to particular limitations so long as they are pharmaceutically acceptable, anions formed from halogen atoms, inorganic acids, organic sulfonic acids, carboxylic acids and the like, such as
F$^-$, Cl$^-$, Br$^-$, I$^-$,

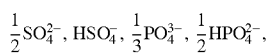

H$_2$PO$_4^-$, NO$_3^-$, CH$_3$OSO$_3^-$,
CH$_3$SO$_3^-$, CH$_3$CH$_2$SO$_3^-$,

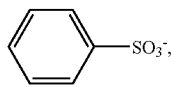

HCOO$^-$, CH$_3$COO$^-$,

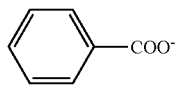

may be named as examples.

"Salts" of the compounds represented by the general formula [I] means, for example, those pharmaceutically acceptable and customarily used salts of the compounds whose A is expressed by the formula [a$_o$], referring to the general formula [I]. As examples of such salts, acid addition salts at the positions of basic nitrogen atom may be named.

Examples of the acid addition salts include inorganic acid salts such as hydrochloride, sulfate, nitrate, phosphate and perchlorate; organic acid salts such as maleate, fumarate, tartarate, citrate, ascorbate and trifluoroacetate; and sulfonic acid salts such as methanesulfonate, isethionate, benzenesulfonate and p-toluenesulfonate.

"Treating agent" means medicines which are used for treatment and/or prophylaxis of various diseases.

The compounds of the present invention in occasions have stereoisomers such as optical isomers, diastereoisomers or geometrical isomers, depending on the form of the substituents therein. The compounds of the present invention cover all of those stereoisomers and their mixtures.

For more specific disclosures of the compounds of the present invention which are represented by the general formula [I], the symbols used in said formula [I] are explained in further details in the following, citing their preferred specific examples.

A stands for a group of the following formula [a$_o$] or [b$_o$]:

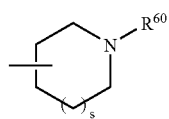

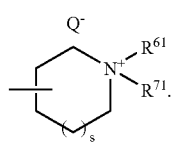

R$^{60}$ stands for hydrogen, C$_1$-C$_{10}$ alkyl, lower alkenyl cycloalkyl, cycloalkyl-lower alkyl whose ring portion may be substituted with lower alkyl, cycloalkenyl-lower alkyl or aralkyl.

Examples of C$_1$-C$_{10}$ alkyl groups as R$^{60}$ include methyl, ethyl, propyl, isopropyl, butyl, isobutyl, pentyl, 2-methylbutyl, hexyl, 2-methylpentyl, heptyl octyl and decyl.

Preferred examples of lower alkenyl group as R$^{60}$ include 2-propenyl and 3-butenyl.

Preferred examples of cycloalkyl group as R$^{60}$ include cyclopentyl and cyclohexyl.

Preferred examples of cycloalkyl-lower alkyl group whose ring portion may be substituted with lower alkyl as R$^{60}$ include cyclopropylmethyl, cyclobutylmethyl, 2-(1-methylcyclopropyl)ethyl, cyclopentylmethyl, (2,2-dimethylcyclopentyl)methyl, 1-cyclopentylethyl, cyclohexylmethyl and 1-cyclohexylethyl.

Preferred examples of cycloalkenyl-lower alkyl group as R$^{60}$ include cycloheptenyl and cyclononenyl.

Preferred examples of aralkyl group as R$^{60}$ include benzyl.

Preferred examples of R$^{60}$ include hydrogen, C$_1$-C$_{10}$ alkyl, cycloalkyl and cycloalkyl-lower alkyl whose ring portion may be substituted with lower alkyl.

R$^{61}$ and R$^{71}$ each independently stands for C$_1$-C$_{10}$ alkyl, lower alkenyl, cycloalkyl, cycloalkyl-lower alkyl whose ring portion may be substituted with lower alkyl, cycloalkenyl-lower alkyl or aralkyl; or R$^{61}$ and R$^{71}$ may together stand for optionally substituted trimethylene, tetramethylene, 2-butenylene, pentamethylene, 3-oxapentamethylene or 2,3-epoxytetramethylene group, the substituent being selected from the group consisting of oxo, hydroxyl, lower alkyl and lower alkoxy.

Preferred examples of C$_1$-C$_{10}$ alkyl groups as R$^{61}$ and R$^{71}$ include C$_1$-C$_6$ alkyl, in particular, methyl ethyl propyl and 2-methylbutyl.

Preferred examples of lower alkenyl as R$^{61}$ and R$^{71}$ include 2-propenyl and 3-butenyl.

Preferred example of cycloalkyl as R$^{61}$ and R$^{71}$ is cyclohexyl.

Preferred examples of cycloalkyl-lower alkyl whose ring portion may be substituted with lower alkyl as R$^{61}$ and R$^{71}$ include cyclopropylmethyl, cyclohexylmethyl, cycloheptylmethyl and cyclooctylmethyl, in particular, cyclopropylmethyl and cyclohexylmethyl, inter alia, cyclopropylmethyl.

Preferred examples of cycloalkenyl-lower alkyl as R$^{61}$ and R$^{71}$ include cycloheptenylmethyl and cyclononenylmethyl.

Preferred examples of aralkyl as R$^{61}$ and R$^{71}$ include benzyl.

"Trimethylene, tetramethylene, 2-butenylene, pentamethylene, 3-oxapentamethylene or 2,3-epoxytetramethylene group, the substituent being selected from the group consisting of oxo, hydroxyl, lower alkyl and lower alkoxy" means unsubstituted trimethylene, tetramethylene, 2-butenylne, pentamethylene, 3-oxapentamethylene or 2,3-expoxytetramethylene; or those having one, two or more, preferably one or two substituents which may be same or different, which are selected from the group consisting of oxo, hydroxyl, lower alkyl and lower alkoxy, at optional substitutable position or positions.

Preferred examples of lower alkyl serviceable as the above substituent include methyl, ethyl and propyl, in particular, methyl.

Preferred examples of lower alkoxy serviceable as the above substituent include methoxy and ethoxy.

Preferred examples of the above substituents include lower alkyl groups.

Among the trimethylene, tetramethylene, 2-butenylene, pentamethylene, 3-oxapentamethylene or 2,3-epoxytetramethylene groups, for example, tetramethylene, 2-butenylene, pentamethylene or 2,3-epoxytetramethylene are preferred.

Hence, among the optionally substituted trimethylene, tetramethylene, 2-butenylene, pentamethylene, 3-oxapentamethylene or 2,3-epoxytetramethylene represented jointly by $R^{61}$ and $R^{71}$, those preferred include unsubstituted tetramethylene, 2-butenylene, pentamethylene and 2,3-epoxytetramethylene; and lower alkyl-substituted tetramethylene, 2-butenylene, pentamethylene and 2,3-epoxytetramethylene.

Preferred embodiments of $R^{61}$ and $R^{71}$ include: those wherein $R^{61}$ and $R^{71}$ each independently is selected from $C_1$-$C_{10}$ alkyl lower alkenyl or cycloalkyl-lower alkyl; or $R^{61}$ and $R^{71}$ together stand for trimethylene, tetramethylene, 2-butenylene, pentamethylene, 3-oxapentamethylene or 2,3-epoxytetramethylene which optionally have substituent(s) selected from the group consisting of oxo, hydroxyl, lower alkyl and lower alkoxy. More specifically, the preferred embodiments include those wherein both $R^{61}$ and $R^{71}$ are methyl, ethyl, propyl, 2-propenyl or cyclopropylmethyl; $R^{61}$ is cyclohexylmethyl and $R^{71}$ is methyl; or $R^{61}$ and $R^{71}$ together form tetramethylene, 2-butenylene, pentamethylene or 2,3-epoxytetramethylene group.

As $Q^-$, for example, anions formed from halogen atoms such as $Cl^-$, $Br^-$ and $I^-$ are preferred;

s means 0, 1 or 2; and $Q^-$ stands for anion, convenient s being 1.

$Ar^1$, $Ar^2$ and $Ar^3$ each independently stands for optionally substituted phenyl, the substituent being selected from the group consisting of halogen, hydroxyl, lower alkyl, lower alkenyl lower alkoxy, carbamoyl, lower alkylcarbamoyl and di-lower alkylcarbamoyl.

Said "optionally substituted phenyl, the substituent being selected from the group consisting of halogen, hydroxyl, lower alkyl, lower alkenyl, lower alkoxy, carbamoyl, lower alkylcarbamoyl and di-lower alkylcarbamoyl" mean unsubstituted phenyl or phenyl having substituent(s) at substitutable, optional position(s), said one, two or more, preferably one or two same or different substituents being selected from the group consisting of halogen, hydroxyl, lower alkyl, lower alkenyl, lower alkoxy, carbamoyl, lower alkylcarbamoyl and di-lower alkylcarbamoyl.

Among the halogen atoms as the substituent, for example, fluorine, chlorine and bromine, inter alia, fluorine, are preferred.

Among the lower alkyl groups as the substituent, for example, methyl, ethyl and propyl are preferred.

Among the lower alkenyl groups as the substituent, for example, vinyl, 1-propenyl and 2-propenyl are preferred.

Among the lower alkoxy groups as the substituent, for example, methoxy and ethoxy are preferred.

Among the lower alkylcarbamoyl groups as the substituent, for example, methylcarbamoyl and ethylcarbamoyl are preferred.

Among the di-lower alkylcarbamoyl groups as the substituent, for example, dimethylcarbamoyl and diethylcarbamoyl are preferred.

As the substituent, halogen atoms and lower alkyl groups are preferred.

As $Ar^1$, $Ar^2$ and $Ar^3$, independently of each other, phenyl which is optionally substituted with halogen or lower alkyl are preferred. In particular, such cases wherein all of them are unsubstituted phenyl, or phenyl substituted with halogen, inter alia, fluorine, are preferred.

The suffix k stands for 0 or 1; and m and n, each independently, 0, 1 or 2, preferred n being 1 or 2.

$R^1$ stands for hydrogen or optionally substituted lower alkyl, the substituent being selected from the group consisting of hydroxyl, amino, carbamoyl, lower alkylcarbamoyl, di-lower alkylcarbamoyl and imidazolyl.

Said "optionally substituted lower alkyl, the substituent being selected from the group consisting of hydroxyl, amino, carbamoyl, lower alkylcarbamoyl, di-lower alkylcarbamoyl and imidazolyl" mean unsubstituted lower alkyl groups as above-named or the lower alkyl groups having substituent(s) at substitutable, optional position(s), said one, two or more, preferably one or two same or different substituents being selected from the group consisting of hydroxyl, amino, carbamoyl, lower alkylcarbamoyl, di-lower alkylcarbamoyl and imidazolyl.

Among the above lower alkylcarbamoyl as the substituent, for example, methylcarbamoyl and ethylcarbamoyl are preferred.

Among the di-lower alkylcarbamoyl as the substituent, for example, dimethylcarbamoyl and diethylcarbamoyl are preferred.

Preferred substituents include hydroxyl, amino and carbamoyl groups.

As the $R^1$ lower alkyl, for example, methyl, ethyl and propyl are preferred.

Thus, specific examples of $R^1$ include hydrogen, methyl, ethyl, propyl, hydroxymethyl, 2-hydroxyethyl, aminomethyl, 2-aminoethyl, carbamoylmethyl, 2-carbamoylethyl, methylcarbamoylmethyl, 2-methylcarbamoylethyl, dimethylcarbamoylmethyl, 2-dimethylcarbamoylethyl, 4-imidazolylmethyl and 2-(4-imidazolyl)ethyl. Of those, hydrogen, methyl, ethyl, propyl, hydroxymethyl, 2-hydroxyethyl, aminomethyl, 2-aminoethyl, carbamoylmethyl and 2-carbamoylethyl are preferred, in particular, hydrogen is preferred.

$R^2$, $R^3$, $R^4$ and $R^5$ each independently stands for hydrogen or optionally substituted lower alkyl, the substituent being selected from the group consisting of hydroxyl, amino, carbamoyl, lower alkylcarbamoyl, di-lower alkylcarbamoyl and imidazolyl or $R^2$ and $R^3$, or $R^4$ and $R^5$, may together stand for, independently of each other, optionally substituted trimethylene, propenylene, tetramethylene or 2-butenylene group, the substituent being selected from the group consisting of oxo, hydroxyl, amino, lower alkoxy, lower alkanoyloxy, lower alkylamino, di-lower alkylamino, (imino-lower alkyl) amino, lower alkanoylamino, lower alkoxycarbonylamino, (lower alkylcarbamoyl)amino, lower alkylsulfonylamino, guanidino, lower alkoxycarbonyl, carbamoyl, lower alkylcarbamoyl, di-lower alkylcarbamoyl, imidazolyl and a group represented by —$R^7$.

Said "optionally substituted lower alkyl, the substituent being selected from the group consisting of hydroxyl, amino, carbamoyl, lower alkylcarbamoyl, di-lower alkylcarbamoyl and imidazolyl" mean unsubstituted lower alkyl groups as above-named or the lower alkyl groups having substituent(s) at substitutable, optional positions(s), said one, two ore more, preferably one or two same or different substituents being selected from the group consisting of hydroxyl, amino, carbamoyl, lower alkylcarbamoyl, di-lower alkylcarbamoyl and imidazolyl.

Among the lower alkylcarbamoyl as the substituent, for example, methylcarbamoyl and ethylcarbamoyl are preferred.

Among the di-lower alkylcarbamoyl as the substituent, for example, dimethylcarbamoyl and diethylcarbamoyl are preferred.

Preferred substituents include hydroxyl, amino, carbamoyl and imidazolyl groups.

As the lower alkyl groups as $R^2$, $R^3$, $R^4$ or $R^5$, for example, methyl, ethyl and propyl are preferred.

Thus, examples of the optionally substituted lower alkyl as $R^2$, $R^3$, $R^4$ or $R^5$ are same to those earlier named optionally substituted lower alkyl groups as $R^1$, among which methyl, ethyl, propyl, hydroxymethyl, 2-hydroxyethyl, aminomethyl 2-aminoethyl, carbamoylmethyl, 2-carbamoylethyl and 4-imidazolylmethyl, inter alia, methyl and 4-imidazolylmethyl, are preferred.

Said "optionally substituted trimethylene, propenylene, tetramethylene or 2-butenylene group, the substituent being selected from the group consisting of oxo, hydroxyl, amino, lower alkoxy, lower alkanoyloxy, lower alkylamino, di-lower alkylamino, (imino-lower alkyl)amino, lower alkanoylamino, lower alkoxycarbonylamino, (lower alkylcarbamoyl) amino, lower alkylsulfonylamino, guanidino, lower alkoxycarbonyl, carbamoyl, lower alkylcarbamoyl, di-lower alkylcarbamoyl, imidazolyl and a group represented by —$R^7$" mean unsubstituted trimethylene, propenylene, tetramethylene and 2-butenylene groups, or those having substituent(s) at substitutable, optional position(s), said one, two or more, preferably one or two same or different substituents being selected from the group consisting of oxo, hydroxyl, amino, lower alkoxy, lower alkanoyloxy, lower alkylamino, di-lower alkylamino, (imino-lower alkyl)amino, lower alkanoylamino, lower alkoxycarbonylamino, (lower alkylcarbamoyl)amino, lower alkylsulfonylamino, guanidino, lower alkoxycarbonyl, carbamoyl, lower alkylcarbamoyl, di-lower alkylcarbamoyl, imidazolyl and a group represented by —$R^7$.

Among the lower alkoxy as the substituent, for example, methoxy, ethoxy, propoxy and tert-butoxy are preferred.

Among the lower alkanoyloxy as the substituent, for example, acetoxy and propionyloxy are preferred.

Among the lower alkylamino as the substituent, for example, methylamino, ethylamino and propylamino are preferred.

Among the di-lower alkylamino as the substituent, for example, dimethylamino and diethylamino are preferred.

Among the (imino-lower alkyl)amino as the substituent, for example, formimidoylamino, acetimidoylamino and propanimidoylamino are preferred.

Among the lower alkanoylamino as the substituent, for example, acetylamino and propionylamino are preferred.

Among the lower alkoxycarbonylamino as the substituent, for example, methoxycarbonylamino, ethoxycarbonylamino and propoxycarbonylamino are preferred.

Among the (lower alkylcarbamoyl)amino as the substituent, for example, (methylcarbamoyl)amino, (ethylcarbamoyl)amino and (propylcarbamoyl)amino are preferred.

Among the lower alkylsulfonylamino as the substituent, for example, methylsulfonylamino, ethylsulfonylamino and propylsulfonylamino are preferred.

Among the lower alkoxycarbonyl as the substituent, for example, methoxycarbonyl, ethoxycarbonyl and propoxycarbonyl are preferred.

Among the lower alkylcarbamoyl as the substituent, for example, methylcarbamoyl, ethylcarbamoyl and propylcarbamoyl are preferred.

Among di-lower alkylcarbamoyl as the substituent, for example, dimethylcarbamoyl and diethylcarbamoyl are preferred.

$R^7$ stands for optionally substituted lower alkyl group, the substituent being selected from the group consisting of hydroxyl, amino, carbamoyl, lower alkylcarbamoyl, di-lower alkylcarbamoyl, lower alkoxycarbonyl and imidazolyl.

"Optionally substituted lower alkyl group, the substituent being selected from the group consisting of hydroxyl, amino, carbamoyl, lower alkylcarbamoyl, di-lower alkylcarbamoyl, lower alkoxycarbonyl and imidazolyl" means unsubstituted lower alkyl groups as above-named or the lower alkyl groups having substituent(s) at substitutable, optional position(s), said one, two or more, preferably one or two same or different substituents being selected from the group consisting of hydroxyl, amino, carbamoyl, lower alkylcarbamoyl, di-lower alkylcarbamoyl, lower alkoxycarbonyl and imidazolyl.

Among the lower alkylcarbamoyl as the substituent, for example, methylcarbamoyl ethylcarbamoyl and propylcarbamoyl are preferred.

Among the di-lower alkylcarbamoyl as the substituent, for example, dimethylcarbamoyl and diethylcarbamoyl are preferred.

Among the lower alkoxycarbonyl as the substituent, for example, methoxycarbonyl, ethoxycarbonyl and propoxycarbonyl are preferred.

As the substituent groups, for example, hydroxyl, amino and carbamoyl are preferred.

As the lower alkyl groups as $R^7$, for example, methyl and ethyl are preferred.

Hence, preferred examples of $R^7$ include methyl, ethyl, propyl, hydroxymethyl, 2-hydroxyethyl, aminomethyl, 2-aminoethyl, carbamoylmethyl, 2-carbamoylethyl, methylcarbamoylmethyl, 2-methylcarbamoylethyl, dimethylcarbamoylmethyl, 2-dimethylcarbamoylethyl, methoxycarbonylmethyl, 2-methoxycarbonylethyl, 4-imidazolylmethyl and 2-(4-imidazolyl)ethyl. In particular, methyl, ethyl, hydroxymethyl, aminomethyl and carbamoylmethyl are preferred.

As the substituent(s) on trimethylene, propenylene, tetramethylene or 2-butenylene, oxo, hydroxyl, amino, lower alkoxy, lower alkylamino and di-lower alkylamino, inter alia, hydroxyl and amino, are preferred.

Among trimethylene, propenylene, tetramethylene and 2-butenylene groups, trimethylene is the preferred.

Accordingly, among those optionally substituted trimethylene, propenylene, tetramethylene and 2-butenylene formed together by $R^2$ and $R^3$, or $R^4$ and $R^5$, unsubstituted trimethylene and hydroxyl- or amino-substituted trimethylene are particularly preferred.

Preferred embodiments of $R^2$, $R^3$, $R^4$ and $R^5$ include one wherein $R^2$, $R^3$, $R^4$ and R, are hydrogen atoms at the same time; those wherein either one of $R^2$ and $R^3$ is hydrogen and the other is an optionally substituted lower alkyl, the substituent being selected from the group consisting of hydroxyl, amino, carbamoyl, lower alkylcarbamoyl, di-lower alkylcarbamoyl and imidazolyl, and both $R^4$ and $R^5$ are hydrogen atoms; and those wherein $R^2$ and $R^3$, or $R^4$ and $R^5$ together stand for, independently of each other, optionally substituted trimethylene, the substituent being selected from the group consisting of oxo, hydroxyl, amino, lower alkoxy, lower alkanoyloxy, lower alkylamino, di-lower alkylamino, (iminolower alkyl)amino, lower alkanoylamino, lower alkoxycarbonylamino, (lower alkylcarbamoyl)amino, lower alkylsulfonylamino, guanidino, lower alkoxycarbonyl, carbamoyl, lower alkylcarbamoyl, di-lower alkylcarbamoyl, imidazolyl and —$R^7$ (here $R^7$ has the earlier defined signification).

Among the compounds represented by the general formula [I], therefore, for example those in which $Ar^1$, $Ar^2$ and $Ar^3$ are each independently phenyl which may be halogen- or lower alkyl-substituted, n is 1 or 2, s is 1, and $R^1$ is hydrogen, are preferred. In particular, the compounds represented by the following general formula [I-a]:

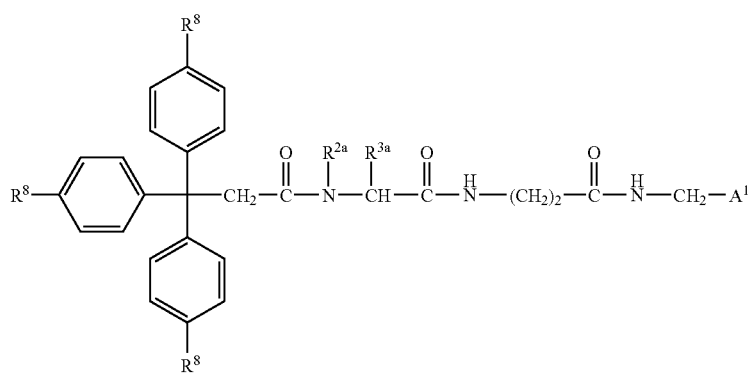
[I-a]

[wherein $A^1$ stands for a group represented by the formula $[a_1]$ or $[b_1]$]

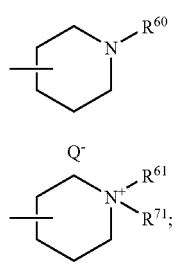
[$a_1$]

[$b_1$]

$R^{2a}$ and $R^{3a}$ each independently stands for hydrogen, or optionally substituted lower alkyl, the substituent being selected from hydroxyl, amino, carbamoyl, lower alkylcarbamoyl, di-lower alkylcarbamoyl and imidazolyl; $R^8$ stands for hydrogen, halogen or lower alkyl; $R^{60}$, $R^{61}$, $R^{71}$ and $Q^-$ have the earlier defined significations];

the compounds represented by the general formula [I-b]:

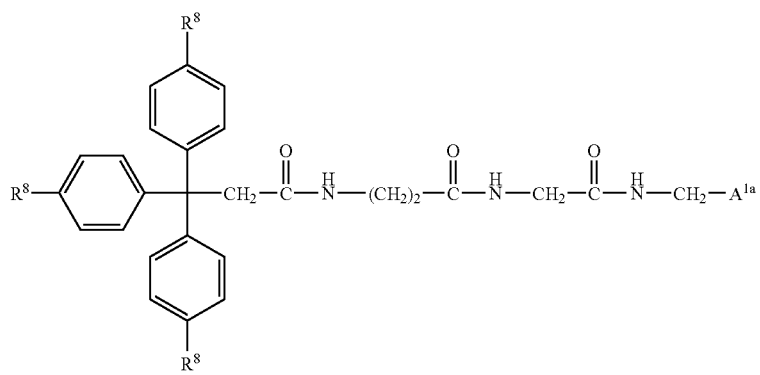
[I-b]

[wherein $A^{1a}$ stands for a group of the formula $[a_1]$]

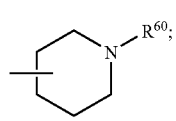
[$a_1$]

and $R^8$ and $R^{60}$ have the earlier defined significations];

the compounds represented by the general formula [I-c]:

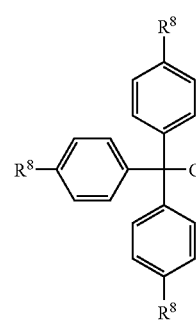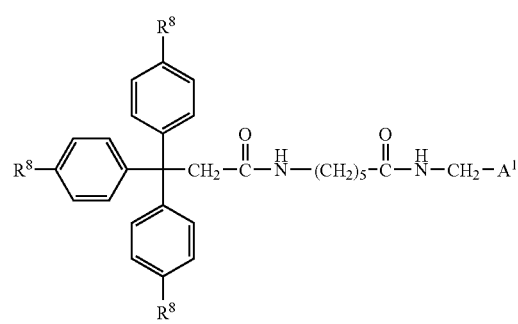
[I-c]

[in which $A^1$ and $R^8$ have the earlier defined significations];

the compounds represented by the general formula [I-d]:

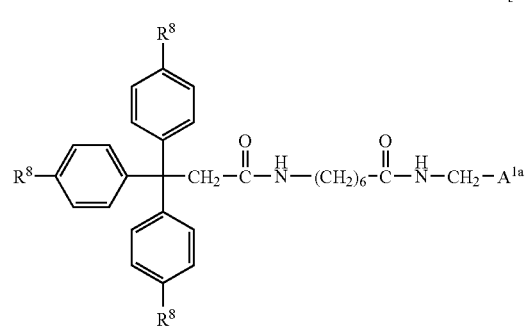
[I-d]

[in which $A^{1a}$ and $R^8$ have the earlier defined significations];

and the compounds represented by the general formula [I-e]

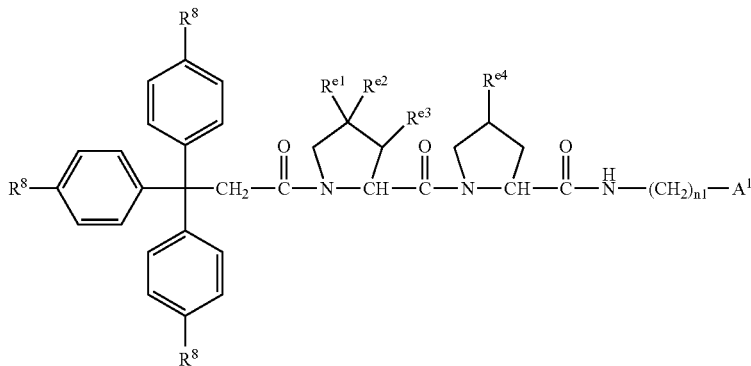

[I-e]

[in which n1 stands for 1 or 2; $R^{e1}$, $R^{e2}$, $R^{e3}$ and $R^{e4}$ each independently stands for hydrogen, hydroxyl, amino, lower alkoxy, lower alkanoyloxy, lower alkylamino, di-lower alkylamino, (imino-lower alkyl)amino, lower alkanoylamino, lower alkoxycarbonylamino, (lower alkylcarbamoyl)amino, lower alkylsulfonylamino, guanidino, lower alkoxycarbonyl, carbamoyl, lower alkylcarbamoyl di-lower alkylcarbamoyl imidazolyl and a group represented by —$R^7$; or $R^{e1}$ and $R^{e2}$ together signify oxo group; and $A^1$, $R^7$ and $R^8$ have the earlier defined significations]

are preferred.

Among the compounds represented by the general formula [I-a], the preferred are those in which $R^{2a}$ is hydrogen and $R^{3a}$ is hydrogen, methyl, ethyl, propyl, hydroxymethyl, 2-hydroxyethyl, aminomethyl, 2-aminoethyl, carbamoylmethyl, 2-carbamoylethyl or 4-imidazolylmethyl, in particular, hydrogen or 4-imidazolylmethyl; or those in which $R^2a$ is methyl and $R^3a$ is hydrogen.

Among the compounds represented by the general formula [I-e], the preferred are those in which $R^{e1}$, $R^{e2}$, $R^{e3}$ and $R^{e4}$ each independently is hydrogen, hydroxyl, amino, methoxy, ethoxy, propoxy, tert-butoxy, acetoxy, methylamino, ethylamino, propylamino, dimethylamino and diethylamino, or those in which $R^{e1}$ and $R^{e2}$ together form oxo group and $R^{e3}$ and $R^{e4}$ both are hydrogen atoms. In particular, the compounds in which $R^{e1}$ is hydroxyl or amino, preferably hydroxyl, and $R^{e2}$, $R^{e3}$ and $R^{e4}$ are hydrogen atoms at the same time; those in which both $R^{e1}$ and $R^{e3}$ are hydroxyl groups and both $R^{e2}$ and $R^{e4}$ are hydrogen atoms; or those in which both $R^{e1}$ and $R^{e2}$ are hydroxyl groups and both $R^{e3}$ and $R^{e4}$ are hydrogen atoms are advantageous. Inter alia, the compounds where $A^1$ is a group represented by the formula [$b_1$], $R^{61}$ and $R^{71}$ are at the same time methyl, ethyl, propyl, 2-propenyl or cyclopropylmethyl, in particular, ethyl, propyl or cyclopropylmethyl; or $R^{61}$ is cyclohexylmethyl and $R^{71}$ is methyl; or $R^{61}$ and $R^{71}$ together form tetramethylene, 2-butenylene or pentamethylene, in particular, tetramethylene or 2-butenylene, can be advantageously used.

Referring to those general formulae [I-a], [I-b], [I-c], [I-d] and [I-e], convenient $R^8$ is, for example, hydrogen or halogen, in particular, hydrogen or fluorine.

Now processes for preparing the compounds of the present invention are explained.

The compounds of the present invention can be prepared by the following processes or those as shown in working examples, it being understood that the preparation processes of compounds of this invention are not limited to those reaction examples.

Production Process 1

Carboxylic acid of the general formoula [II]:

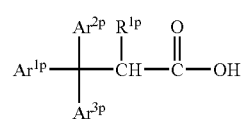

[II]

[in which $Ar^{1p}$, $Ar^{2p}$ and $Ar^{3p}$ each independently stands for optionally substituted phenyl the substituent being selected from the group consisting of halogen, lower alkyl, lower alkenyl, lower alkoxy and di-lower alkylcarbamoyl and optionally protected hydroxyl, carbamoyl and lower alkylcarbamoyl; and $R^{1p}$ stands for hydrogen or optionally substituted lower alkyl, the substituent being selected from the group consisting of di-lower alkylcarbamoyl optionally protected hydroxyl, amino, carbamoyl, lower alkylcarbamoyl and imidazolyl groups]

or salt or reactive derivative thereof is reacted with a compound of the general formula [III]:

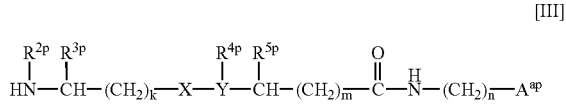

[III]

[in which $A^{ap}$ stands for a group of the formula [$a_{op}$]]

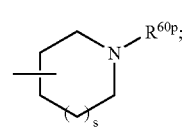

[$a_{op}$]

$R^{2p}$, $R^{3p}$, $R^{4p}$ and $R^{5p}$ each independently stands for hydrogen or optionally substituted lower alkyl, the substituent being selected from the group consisting of di-lower alkylcarbamoyl and optionally protected hydroxyl, amino, carbamoyl, lower alkylcarbamoyl and imidazolyl groups, or $R^{2p}$ and $R^{3p}$, or $R^{4p}$ and $R^{5p}$, together form, each independently of the other pair, optionally substituted trimethylene, propenylene, tetramethylene or 2-butenylene, the substituent being selected from the group consisting of lower alkoxy, lower alkanoyloxy, di-lower alkylamino, lower alkoxycarbonyl, di-lower alkylcarbamoyl, a group represented by $—R^{7p}$ and optionally protected oxo, hydroxyl, amino, lower alkylamino, (imino-lower alkyl)amino, lower alkanoylamino, lower alkoxycarbonylamino, (lower alkylcarbamoyl)amino, lower alkylsulfonylamino, guanidino, carbamoyl, lower alkylcarbamoyl and imidazolyl groups; $R^{7p}$ stands for optionally substituted lower alkyl, the substituent being selected from the group consisting of di-lower alkylcarbamoyl and lower alkoxycarbonyl, and optionally protected hydroxyl, amino, carbamoyl, lower alkylcarbamoyl and imidazolyl groups; $R^{60p}$ stands for imino-protecting group, $C_1$-$C_{10}$ alkyl, lower alkenyl, cycloalkyl, cycloalkyl-lower alkyl whose ring potion being optionally substituted with lower alkyl, cycloalkenyl-lower alkyl or aralkyl; and k, m, n, s, X and Y have the earlier defined significations]

or salt thereof, to form a compound represented by the general formula [IV-1]

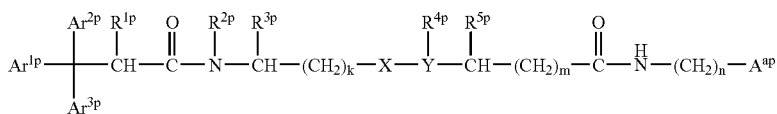

[in which $A^{ap}$, $Ar^{1p}$, $Ar^{2p}$, $Ar^{3p}$, k, m, n, $R^{1p}$, $R^{2p}$, $R^{3p}$, $R^{4p}$, $R^{5p}$ P X and Y have the earlier defined significations]

or a salt thereof, and if necessary the protective group(s) are removed to produce a compound represented by the general formula [I-1]

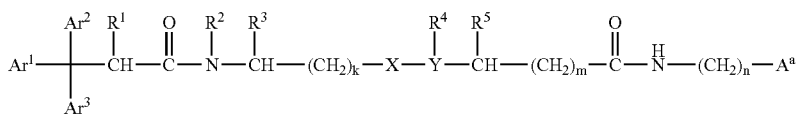

[in which $A^{a}$ stands for a group of the formula [$a_0$]

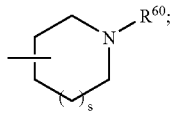

$Ar^1$, $Ar^2$, $Ar^3$, k, m, n, $R^2$, $R^3$, $R^4$, $R^5$, $R^{60}$, s, X and Y have the earlier defined significations]

or salts thereof.

The above production process 1 is the process for producing, among the compounds of the present invention which are represented by the general formula [I], those in which A in said general formula is a group represented by the formula [$a_0$]

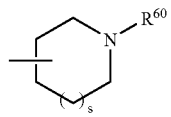

[in which $R^{60}$ and s have the earlier defined significations], i.e., the compounds expressed by the earlier given general formula [I-1].

Where the reactants in the above reaction contain oxo, hydroxyl, amino or imino groups which do not participate in the reaction, those groups are preferably suitably protected by respective protective groups before the reaction, and are deprotected after the reaction.

Examples of "oxo-protective group" include acetals and ketals such as ethylene ketal, trimethylene ketal and dimethyl ketal.

Examples of "hydroxyl-protective group" include alkyl such as tert-butyl; substituted silyls such as trimethylsilyl, tert-butyldimethylsilyl and tert-butyldiphenylsilyl; lower alkoxymethyl such as methoxymethyl and 2-methoxyethoxymethyl; tetrahydropyranyl; trimethylsilylethoxymethyl; aralkyl such as benzyl, p-methoxybenzyl, 2,3-dimethyoxybenzyl, o-nitrogenzyl, p-nitrobenzyl and triphenylmethyl; and acyl such as formyl and acetyl. In particular, tert-butyl, benzyl, methoxymethyl, tetrahydropyranyl, triphenylmethyl, trimethylsilylethoxymethyl, tert-butyldimethylsilyl and acetyl groups are preferred.

Examples of "amino- or imino-protective group" include aralkyl such as benzyl, p-methoxybenzyl, 3,4-dimethoxybenzyl, o-nitrobenzyl, p-nitrobenzyl, benzhydryl and triphenylmethyl; lower alkanoyl such as formyl, acetyl, propionyl, butyryl and pivaloyl; benzoyl; arylalkanoyl such as phenylacetyl and phenoxyacetyl; lower alkoxycarbonyl such as methoxycarbonyl, ethoxycarbonyl, propyloxycarbonyl and tert-butoxycarbonyl; aralkyloxycarbonyl such as benzyloxycarbonyl, p-nitrobenzyloxycarbonyl and phenethyloxycarbonyl; lower alkylsilyl such as trimethylsilyl and tert-butyldimethylsilyl; phthaloyl; and aralkylidene such as benzylidene, p-chlorobenzylidene and o-nitrobenzylidene. In particular, acetyl, pivaloyl, benzoyl, ethoxycarbonyl, benzyloxycarbonyl and tert-butoxycarbonyl groups are preferred.

The reaction of a carboxylic acid of the general foromula [II] or salt or reactive derivative thereof with a compound expressed by the general formula [III] or salt thereof is usually carried out using 1-5 mols, preferably 1-2 mols, of the carboxylic acid of the formula [II] or salt or reactive derivative thereof, per mol of the compound of the formula [III] or salt thereof.

"Salt" of said carboxylic acid of the formula [II] means base addition salt at the carboxyl group, examples of which include alkali metal salt such as sodium salt and potassium salt; alkaline earth metal salt such as calcium salt and magnesium salt; ammonium salt; and organic amine salt such as trimethylamine salt, triethylamine salt, dicyclohexylamine salt, ethanolamine salt, diethanolamine salt, triethanolamine salt, procaine salt and N,N-dibenzylethylenediamine salt.

Examples of "reactive derivative" of the carboxylic acid of the formula [II] are mixed acid anhydrides, active esters and active amides.

Where said carboxylic acid of the formula [II] or salt thereof is used in the reaction, the reaction is preferably carried out in the presence of a condensing agent such as, for example, N,N'-dicyclohexylcarbodiimide, 1-ethyl-3-(3-dimethylaminopropyl)carbodiimide, diphenylphosphoryl azide and dipyridyldisulfide-triphenylphosphin, in particular, 1-ethyl-3-(3-dimethylaminopropyl)carbodiimide hydrochloride.

The use rate of the condensing agent is not strictly limited, while it is usually in the range of 1-5 mols, preferably 1-2 mols, per mol of the carboxylic acid of the formula [II] or salt thereof.

The reaction is usually carried out in an inert solvent, examples of which include diethyl ether, tetrahydrofuran, N,N-dimethylformamide, dioxane, benzene, toluene, chlorobenzene, methylene chloride, chloroform, carbon tetrachloride, dichloroethane and trichloroethylene; and mixtures of those solvents. In particular, diethyl ether, tetrahydrofuran, N,N-dimethylformamide, chloroform and dioxane are preferred.

The reaction temperature usually ranges from −70° C. to the boiling point of the solvent used in the reaction, preferably −20° C.-100° C.

Mixed acid anhydride of carboxylic acid of the formula [II] can be obtained by reacting carboxylic acid of the formula [II] with, for example, alkyl chlorocarbonate such as ethyl chlorocarbonate; aliphatic carboxylic acid chloride such as acetyl chloride, pivaloyl chloride and the like, according to usual method.

Active esters of carboxylic acid of the formula [II] can be obtained by reacting the carboxylic acid of said formula [II] with, for example, an N-hydroxy compound such as N-hydroxysuccinimide, N-hydroxyphthalimide or 1-hydroxybenzotriazole; or a phenol compound such as 4-nitrophenol, 2,4-dinitrophenol, 2,4,5-trichlorophenol, pentachlorophenol or the like; in the presence of a condensing agent, e.g., N,N'-dicyclohexylcarbodiimide, 1-ethyl-3-(3-dimethylaminopropyl)carbodiimide hydrochloride, diphenylphosphoryl azide or dipyridyl disulfide-triphenylphosphine, according to usual method.

Active amide of the carboxylic acid of the formula [II] can be obtained by reacting the carboxylic acid of formula [II] with 1,1'-carbonyldiimidazole, 1,1'-carbonylbis(2-methylimidazole) or the like according to usual methods.

After completion of the reaction, ordinary treatment is given to provide crude product of a compound expressed by the general formula [IV-1], which is optionally purified according to usual method and further if necessary subjected to a reaction for removing protective group(s) of oxo, hydroxyl, amino or imino, to provide a compound of the formula [I-1].

Method for removing the protective group(s) differs depending on the kind of the protective group and stability of the object compound [I-1], but those methods known per se may be employed, for example, those taught in *Protective Groups in Organic Synthesis,* T. W. Greene, John Wiley & Sons Co. (1981) or methods analogous thereto, for example, solvolysis using an acid or base, that is, using for example 0.01 mol—a large excess of an acid, preferably trifluoroacetic acid, formic acid, hydrochloric acid or the like, or an equimolar or largely excessive amount of a base, preferably potassium hydroxide, calcium hydroxide or the like; chemical reduction using hydrogenated metal complex or catalytic reduction using palladium-carbon catalyst or Raney nickel catalyst.

Production Process 2

By following the steps of reacting a compound expressed by the following general formula [IV-1a]:

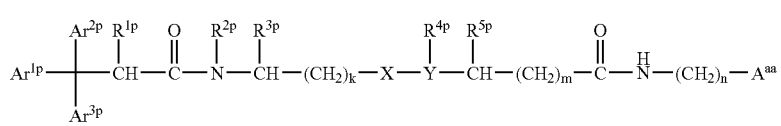

[IV-1a]

The reaction time usually ranges from 5 minutes to 7 days, preferably from 10 minutes to 24 hours.

The reaction may also be carried out in the presence of a base, for smooth progress of the reaction.

Examples of useful base include aliphatic tertiary amine such as triethylamine and diisopropylethylamine; and aromatic amines such as pyridine, 4-dimethylaminopyridine and quinoline. Of those, triethylamine and 4-dimethylaminopyridine are preferred.

The use rate of said basecan be within a range of 1-5 mols, preferably 1-2 mols, per mol of the carboxylic acid expressed by the formula [II] or salt or reactive derivative thereof.

[in which $A^{aa}$ signifies a group represented by the formula $[a_{oa}]$

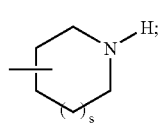

$[a_{0a}]$ $Ar^{1p}, Ar^{2p}, Ar^{3p}, k, m, n, R^{1p}, R^{2p}, R^{3p}, R^{4p}, R^{5p}, S, X,$ and Y have the earlier defined significations]

or a salt thereof, with a compound of a general formula [V]

$$O=R^{61a} \quad [V]$$

[in which $R^{61a}$ signfies $C_1$-$C_{10}$ alkylidene, lower alkenylidene, cycloalkylidene, cycloalkyl lower alkylidene whose ring portion may be substituted with lower alkyl, cycloalkenyl lower alkylidene or aralkylidene]

under reducing conditions to form a compound of a general formula [IV-1b]:

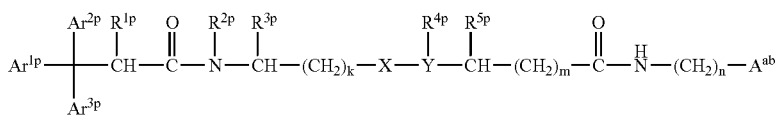

[IV-1b]

[in which $A^{ab}$ signifies a group represented by the formula $[a_{ob}]$

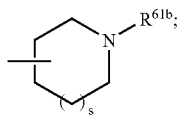

[$a_{0b}$]

$R^{61b}$ signifies $C_1$-$C_{10}$ alkyl, lower alkenyl, cycloalkyl, cycloalkyl-lower alkyl whose ring portion may be substituted with lower alkyl, cycloalkenyl-lower alkyl or aralkyl; $Ar^{1p}, Ar^{2p}, Ar^{3p}, k, m, n, R^{1p}, R^{2p}, R^{3p}, R^{4p}, R^{5p}$, S, X, and Y have the earlier defined significations]

or a salt thereof, and if necessary removing the protective groups, a compound of the general formula [1-2]:

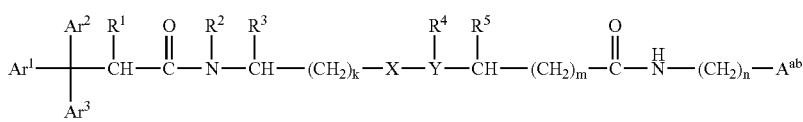

[I-2]

[in which $A^{ab}, Ar^1, Ar^2, Ar^3, k, m, n, R^1, R^2, R^3, R^4, R^5$, S, X and Y have the earlier defined significations]

or a salt thereof can be produced.

The production process 2 is a process for producing, among the compounds of the present invention represented by the general formula [I], those in which A is the group expressed by the formula $[a_{ob}]$:

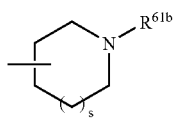

[$a_{0b}$]

[in which $R^{61b}$ and s have the earlier defined significations], i.e., the compounds expressed by the general formula [I-2].

Said "$C_1$-$C_{10}$ alkylidene, lower alkenylidene, cycloalkylidene, cycloalkyl-lower alkylidene whose ring portion may be substituted with lower alkyl, cycloalkenyl-lower alkylidene or aralkylidene" as $R^{61a}$ mean those which are capable of becoming the corresponding "$C_1$-$C_{10}$ alkyl, lower alkenyl, cycloalkyl, cycloalkyl-lower alkyl whose ring portion may be substituted with lower alkyl, cycloalkenyl-lower alkyl or aralkyl", respectively, after completion of the above reaction.

The reaction of a compound represented by the general formula [IV-1a] or a salt thereof with a compound represented by the general formula [V] under reducing conditions is a so-called reductive alkylatin reaction of an amino group, and conducted using a mol or molar excess, preferably 1-2 mols, of the compound of the general formula [V] per mol of the compound of the general formula [IV-1a] or salt thereof, in the presence of a reducing agent or under catalytic redution, in an inert solvent which has no adverse effect on the reaction.

As the inert solvent, for example, alcohols such a methanol or ethanol; ethers such as diethyl ether, methyl tert-butyl ether, tetrahydrofuran or dioxane; aromatic hydrocarbons such as benzene or toluene; halogenated hydrocarbons such as dichloroethane; or their mixtures can be named, in particular, methanol ethanol, tetrahydrofuran, dichloroethane or toluene being preferred.

Where the reaction is carried out in the presence of a reducing agent, examples of useful reducing agent include complex metal hydrides such as sodium boron hydride, sodium cyanoboron hydride, aluminium lithium hydride, aluminium diisobutyl hydride and sodium triacetoxyboron hydride; in particular, sodium boron hydride, sodium cyanoboron hydride or sodium triacetoxyboron hydride being preferred.

The use rate of said reducing agent is usually a mol to molar excess, preferably 1-10 mols, per mol of the compound represented by the general formula [IV-1a] or salt thereof.

The reaction temperature usually ranges from about −30° C. to about 200° C., preferably from about 0° C. to 100° C.; and the reaction time usually ranges from an instant to 7 days, preferably from an instant to 24 hours.

Where the reaction is carried out under catalytic reduction, for example, palladium-carbon catalyst, Raney nickel catalyst or the like is used as the catalyst.

The hydrogen pressure in the catalytic reduction reaction is usually and conveniently from atmospheric to 2 atmospheres, and the use rate of the catalyst is usually from 1/100 to 1, preferably 1/100-1/10 by weight to the starting compound [IV-1a].

The reaction temperature usually ranges from about −30° C. to 50° C., preferably from about 0° C. to room temperature, and the reaction time usually ranges from an instant to 7 days, preferably from an instant to 24 hours.

As the means of reduction in this reaction, the above-described reduction method using the complex metal hydride is convenient.

This reaction may be conducted under weakly acidic conditions, in which Schiff base is easily formed. As examples of acid useful for pH control for that purpose include p-toluenesulfonic acid, hydrochloric acid, sulfuric acid, acetic acid and trifluoroacetic acid.

In this step it is also possible not to conduct the reaction in the presence of a reducing agent or under catalytic reduction, but to first react a compound of the general formula [IV-1a] or salt thereof with a compound of the general formula [V] to form an imine in advance, and then to subject said imine to a reducing reaction.

In the above reaction where such groups as oxo, hydroxyl, amino or imino which do not participate in the reaction are present in the reactants, it is desirable to suitably protect them with protective groups of oxo, hydroxyl, amino or imino, respectively, before the reaction and to remove the protective groups after the reaction.

As the protective groups suitable for oxo, hydroxyl, amino or imino, those respective protective groups as described in relation to the production process 1 are applicable as they are.

Upon completion of the reaction, after removing the protective groups in the compound of the general formula [IV-1b] where they are present; or where no protective group is present in the product, without such an intervening treatment, the product is processed in the usual manner to produce a compound of the general formula [1-2].

For removing the protective groups and conducting the post-treatment, those methods as described as to the production process 1 are applicable.

Production Process 3

By following the steps of reacting a compound of the general formula [IV-1a]:

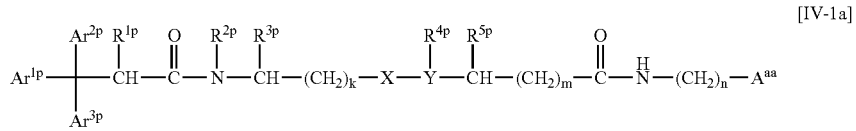
[IV-1a]

[in which $A^{aa}$, $Ar^{1p}$, $Ar^{2p}$, $Ar^{3p}$, k, m, n, $R^{1p}$, $R^{2p}$, $R^{3p}$, $R^{4p}$, $R^{5p}$, X and Y have the earlier defined significations]

or a salt thereof with a compound of the general formula [VI-1]

[VI-1]

[in which $L^1$ signifies a leaving group, and $R^{61b}$ has the earlier defined signification]

to form a compound expressed by the general formula [IV-1b]

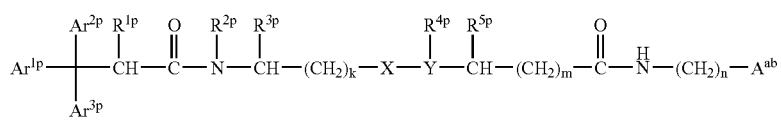
[IV-1b]

[in which $A^{ab}$, $Ar^{1p}$, $Ar^{2p}$, $Ar^{3p}$, k, m, n, $R^{1p}$, $R^{2p}$, $R^{3p}$, $R^{4p}$, $R^{5p}$, X and Y have the earlier defined significations]

or salt thereof, and if necessary removing the protective groups, a compound of the general formula [I-2]

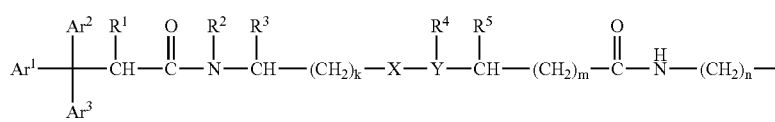
[I-2]

[in which $A^{ab}$, $Ar^1$, $Ar^2$, $Ar^3$, k, m, n, $R^1$, $R^2$, $R^3$, $R^4$, $R^5$, s, X and Y have the earlier defined significations]

or a salt thereof can be produced.

The production process 3 is a method for producing the compounds expressed by the general formula [I-2], same as above production process 2.

Examples of "leaving group" expressed by $L^1$ include halogen atoms such as chlorine, bromine and iodine; alkylsulfonyloxy groups such as methylsulfonyloxy; or arylsulfonyloxy groups such as p-toluenesulfonyloxy.

The reaction of a compound of the general formula [IV-1a] or a salt thereof with a compound of the general formula [IV-1] is usually conducted using a mol or molar excess, preferably 1-2 mols, of the compound of the formula [VI-1] per mol of the compound of formula [IV-1a] or salt thereof, in an inert solvent which is not detrimental to the reaction.

As such inert solvent, for example, ethers such as diethyl ether, tetrahydrofuran and dioxane; aromatic hydrocarbons such as benzene, toluene, chlorobenzene and xylene; and aprotic polar solvents such as dimethylsulfoxide, N,N-dimethylformamide, acetonitrile and hexamethylphosphoric triamide; or mixtures of the foregoing can be used.

For smooth progress, the reaction may be carried out in the presence of base and/or a reaction assistant.

As the base, for example, alkali metal bicarbonates such as sodium hydrogencarbonate and potassium hydrogencarbonate; alkali metal carbonates such as sodium carbonate and potassium carbonate; tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo-[5.4.0]undec-7-ene (DBU) and 1,5-diazabicyclo[4.3.0]non-5-ene (DBN); and aromatic amines such as pyridine, 4-dimethylaminopyridine, picoline, lutidine, quinoline and isoquinoline can be used. Of those, potassium carbonate, N,N-diisopropylethylamine and triethylamine are preferred.

The use rate of the base is usually a mol or molar excess, preferably 1-3 mols, per mol of the compound of the formula [IV-1a].

As assistant useful for the reaction, for example, alkali metal iodides such as lithium iodide, sodium iodide and potassium iodide may be named. Of these, potassium iodide is preferred.

The use rate of the assistant is usually from catalytic to excessive amount, preferably from catalytic amount to one equivalent, to the compound of the formula [IV-1a].

The reaction temperature may usually range from about 0° C. to the boiling point of the solvent used in the reaction, and the reaction time may usually range from 10 minutes to 48 hours.

In the above reaction where such groups as oxo, hydroxyl, amino or imino which do not participate in the reaction are present in the reactants, it is desirable to suitably protect them with protective groups of oxo, hydroxyl, amino or imino, respectively, before the reaction and to remove the protective groups after the reaction.

As the protective groups suitable for oxo, hydroxyl, amino or imino, those respective protective groups as described in relation to the production process 1 are applicable as they are.

Upon completion of the reaction, after removing the protective groups in the compound of the general formula [IV-1b] where they are present; or where no protective group is present in the product, without such an intervening treatment, the product is processed in the usual manner to produce a compound of the general formula [I-2].

For removing the protective groups and conducting the post-treatment, those methods as described as to the production process 1 are applicable Production Process 4

By following the steps of reacting a compound of the general formula [VI-2]:

[in which $L^2$ signifies a leaving group; $R^{71a}$ signifies $C_1$-$C_{10}$ alkyl, lower alkenyl, cycloalkyl, cycloalkyl-lower alkyl whose ring portion may be substituted with lower alkyl, cycloalkenyl-lower alkyl or aralkyl]

or a salt thereof with a compound of the general formula [IV-1b]:

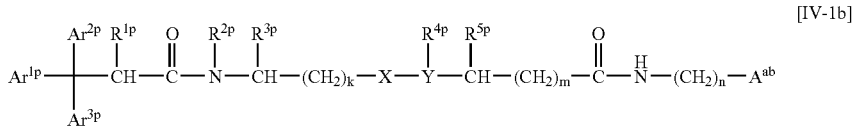

[in which $A^{ab}$, $Ar^{1p}$, $Ar^{2p}$, $Ar^{3p}$, k, m, n, $R^{1p}$, $R^{2p}$, $R^{3p}$, $R^{4p}$, $R^{5p}$, s, X and Y have the earlier defined significations]

or a salt thereof, to form a compound expressed by the general formula [IV-2]:

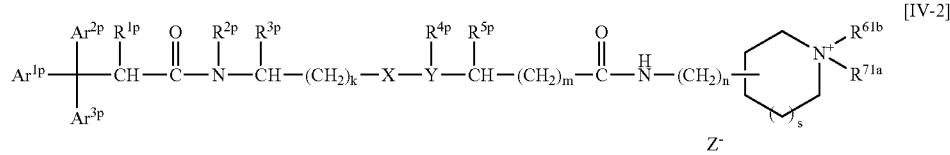

[in which $Z^-$ signifies anion; $Ar^{1p}$, $Ar^{2p}$, $Ar^{3p}$, k, m, n, $R^{1p}$, $R^{2p}$, $R^{3p}$, $R^{4p}$, $R^{5p}$, $R^{61b}$, $R^{71a}$, s, X and Y have the earlier defined significations]

and if necessary removing the protective group(s) and/or exchanging the anion, a compound of the general formula [I-3]:

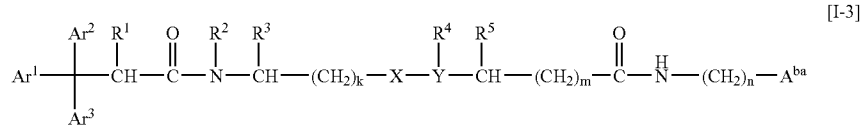

[in which $A^{ba}$ signifies a group expressed by the formula [$b_{oa}$]

$Ar^1$, $Ar^2$, $Ar^3$, k, m, n, $R^1$, $R^2$, $R^3$, $R^4$, $R^5$, $R^{61b}$, $R^{71a}$, s, X, Y and $Q^-$ have the earlier defined significations]

can be produced.

The production process 4 is a method for producing, among the compounds of the present invention represented by the general formula [I], those in which A is a group expressed by the formula [$b_{oa}$]:

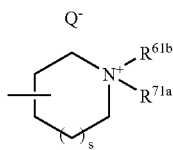

[b0a]

[in which $R^{61b}$, $R^{71a}$, s and $Q^-$ have the earlier defined significations], i.e., the compounds represented by the general formula [I-3].

As the "leaving group" expressed by $L^2$, those leaving groups exemplified as $L^1$ in the production process 3 are equally applicable.

In the above reaction where such groups as oxo, hydroxyl, amino or imino which do not participate in the reaction are present in the reactants, it is desirable to suitably protect them with protective groups of oxo, hydroxyl, amino or imino, respectively, before the reaction and to remove the protective groups after the reaction.

As the protective groups suitable for oxo, hydroxyl amino or imino, those respective protective groups as described in relation to the production process 1 are applicable as they are.

The reaction of a compound expressed by the general formula [VI-2] or salt thereof with a compound of the general formula [IV-1b] or salt thereof is usually carried out using a mol or molar excess, preferably a large molar excess, of the compound of formula [VI-2] or salt thereof, per mol of the compound of the formula [IV-1b] or salt thereof, in the absence of a solvent or in an inert solvent which is not detrimental to the reaction, non-use of solvent being preferred.

As such inert solvent, for example, ethers such as diethyl ether, tetrahydrofuran and dioxane; aromatic hydrocarbons such as benzene, toluene, chlorobenzene and xylene; halogenated hydro-carbons such as chloroform, dichloromethane and dichloroethane; and aprotic polar solvents such as dimethyl sulfoxide, N,N-dimethylformamide, acetonitrile and hexamethylphosphoric triamide; or mixtures of the foregoing can be used, in particular, chloroform and acetonitrile being preferred.

For smooth progress, the reaction may be carried out in the presence of base and/or a reaction assistant.

As the base, for example, alkali metal bicarbonates such as sodium hydrogencarbonate and potassium hydrogencarbonate; alkali metal carbonates such as sodium carbonate and potassium carbonate; tertiary aliphatic amines such as trimethylamine, diethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-diazabicyclo[4.3.0]-non-5-ene (DBN); and aromatic amines such as pyridine, 4-dimethylaminopyridine, picoline, lutidine, quinoline and isoquinoline can be used. Of those, potassium carbonate, diethylamine, triethylamine and N,N-diisopropylethylamine are particularly suitable.

The use rate of the base is usually a mol or molar excess, preferably 1-3 mols, per mol of the compound of the formula [IV-1b].

As assistant useful for the reaction, for example, alkali metal iodides such as lithium iodide, sodium iodide and potassium iodide may be named. Of these, potassium iodide is preferred.

The use rate of the assistant is usually from catalytic to excessive amount, preferably from catalytic amount to one equivalent, to the compound of the formula [IV-1b].

The reaction temperature may usually range from about 0° C. to the boiling point of the solvent or reagent used in the reaction, preferably from 20° C. to the boiling point of the solvent or reagent used in the reaction, and the reaction time may usually range from 10 minutes to 48 hours, preferably 1-10 hours.

Upon completion of the reaction, after removing the protective groups in the compound of the general formula [IV-2] where they are present; or where no protective group is present in the product, without such an intervening treatment, the product is processed in the usual manner to produce a compound of the general formula [I-3].

For removing the protective groups and conducting the post-treatment, those methods as described as to the production process 1 are applicable.

Those compounds of the general formula [I-3] are isolated as those having a certain or more than one kind of anions, and thereafter the anions can be changed to other desired anions.

As the method of changing anions, for example, one comprising adsorbing the formula [I-3] compound onto a column filled with an adequate carrier, treating the same with a salt of an acid having an excess of desired anions, and eluting the intended formula [I-3] compound as formed.

Production Process 5

By following the steps of reacting a compound of the general formula [VII]:

$$L^3\text{-}R^{71bp}\text{-}L^4 \qquad [VII]$$

[in which $L^3$ and $L^4$ each independently signifies a leaving group, and $R^{71bp}$ signifies optionally substituted trimethylene, tetramethylene, 2-butenylene, pentamethylene, 3-oxapentamethylene or 2,3-epoxytetramethylene, the substituent being selected from the group consisting of lower alkyl lower alkoxy, and optionally protected oxo and hydroxyl]

or a salt thereof with a compound of a general formula [IV-1a]

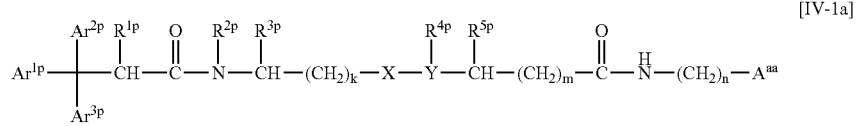

[IV-1a]

[in which $A^{aa}$, $Ar^{1p}$, $Ar^{2p}$, $Ar^{3p}$, k, m, n, $R^{1p}$, $R^{2p}$, $R^{3p}$, $R^{4p}$, $R^{5p}$, s, X and Y have the earlier defined significations]

or a salt thereof, to form a compound of the general formula [IV-3]

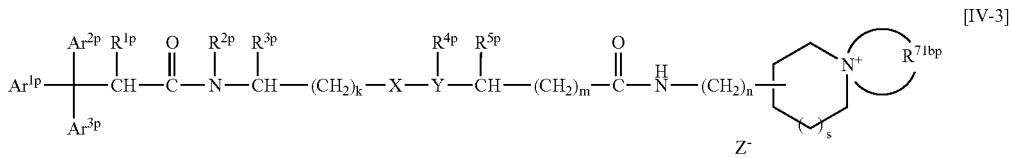

[in which $Ar^{1p}$, $Ar^{2p}$, $Ar^{3p}$, k, m, n, $R^{1p}$, $R^{2p}$, $R^{3p}$, $R^{4p}$, $R^{5p}$, $R^{71bp}$, s, X, Y and $Z^-$ have the earlier defined significations], and if necessary removing protective groups and/or exchanging the anion, a compound expressed by the general formula [I-4]:

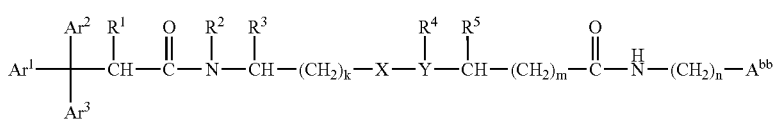

[in which $A^{bb}$ signifies a group expressed by the formula [$b_{ob}$]:

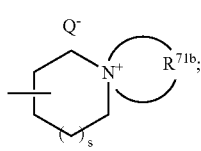

$Ar^1$, $Ar^2$, $Ar^3$, $R^1$, $R^2$, $R^3$, $R^4$, $R^5$, $R^{71b}$, k, m, s, X, Y and $Q^-$ have the earlier defined significations]

can be produced.

The production process 5 is a method for producing, among the compounds of the present invention represented by the general formula [I], those in which A is a group expressed by the formula [$b_{ob}$]:

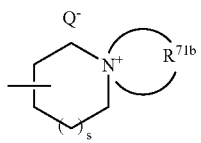

[in which $R^{71b}$, s and $Q^-$ have the earlier defined significations], i.e., the compounds represented by the general formula [I-4].

As the "leaving group" expressed by $L^3$ or $L^4$, those exemplified as $L^1$ in the production process 3 are applicable independently of each other.

In the above reaction where such groups as oxo, hydroxyl amino or imino which do not participate in the reaction are present in the reactants, it is desirable to suitably protect them with protective groups of oxo, hydroxyl, amino or imino, respectively, before the reaction and to remove the protective groups after the reaction.

As the protective groups suitable for oxo, hydroxyl, amino or imino, those respective protective groups as described in relation to the production process 1 are applicable as they are.

The reaction of a compound expressed by the general formula[IV-1a] or salt thereof with a compound of the general formula [VII] or salt thereof is usually carried out using a mol or molar excess, preferably 1-5 mols, of the compound of the formula [VII] or salt thereof, per mol of the compound of the formula [IV-1a] or salt thereof, in an inert solvent which is not detrimental to the reaction.

As such inert solvent, for example, ethers such as diethyl ether, tetrahydrofuran and dioxane; aromatic hydrocarbons such as benzene, toluene, chlorobenzene and xylene; halogenated hydrocarbons such as chloroform, dichloromethane and dichloroethane; and aprotic polar solvents such as dimethyl sulfoxide, N,N-dimethylformamide, acetonitrile and hexamethylphosphoric triamide; or mixtures of the foregoing can be used, among which chloroform and acetonitrile are preferred.

For smooth progress, the reaction may be carried out in the presence of base and/or a reaction assistant.

As the base, for example, alkali metal bicarbonates such as sodium hydrogencarbonate and potassium hydrogencarbonate; alkali metal carbonates such as sodium carbonate and potassium carbonate; tertiary aliphatic amines such as trimethylamine, diethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-diazabicyclo-[4.3.0]non-5-ene (DBN); and aromatic amines such as pyridine, 4-dimethylaminopyridine, picoline, lutidine, quinoline and isoquinouine can be used. Of those, potassium carbonate, diethylamine, triethylamine and N,N-diisopropylethylamine are preferred.

The use rate of the base is usually a mol or molar excess, preferably 1-3 mols, per mol of the compound of the formula [IV-1a].

As assistant useful for the reaction, for example, alkali metal iodides such as lithium iodide, sodium iodide and potassium iodide may be named. Of these, potassium iodide is preferred.

The use rate of the assistant is usually from catalytic to excessive amount, preferably from catalytic amount to one equivalent, to the compound of the formula [IV-1a].

The reaction temperature may usually range from about 0° C. to the boiling point of the solvent or reagent which is used in the reaction, preferably from 20° C. to the solvent or reagent used in the reaction, and the reaction time may usually range from 10 minutes to 48 hours, preferably 1-10 hours.

Upon completion of the reaction, after removing the protective groups in the compound of the general formula [IV-3] where they are present; or where no protective group is present in the product, without such an intervening treatment, the product is processed in the usual manner or if necessary exchanged of the anions therein to produce a compound of the general formula [1-4].

For removing the protective groups and other post-treatments, those methods as described in the explanation of the production process 1 are applicable as they are, and for changing anions, the method as described as to above production process 4 is applicable as it is.

Isolation and purification of those compounds of the general formulae [I-1], [I-2], [I-3] or [I-4] which are obtained in above processes can be accomplished by customarily practiced separation means such as column chromatography using silica gel, adsorptive resins and the like, thin-layer chromatography, liquid chromatography, solvent extraction or recrystallization-reprecipitation, applied singly or in combination.

Compounds of the general formula [I-1] or [I-2] are convertible to pharmaceutically acceptable salts by customary means and conversely, conversion from the salts to free compounds can also be conducted following customary means.

As those compounds represented by general formulae [II], [III], [IV-1a], [V], [VI-1], [VI-2] or [VII], commercial products may be used, or they can be prepared by methods which are described in literature references (cf. M. Bodansky and M. A. Ondetti, *Peptide Synthesis,* Interscience, New York, 1966; F. M. Finn and K. Hofmann, *The Proteins,* Vol. 2, ed. by H. Nenrath and R. L. Hill, Academic Press Inc., New York, 1976; Nobuo Izumiya, et al., Peptide Gosei (synthesis), Maruzen Co., 1975; and Official Patent KOKAI (laid-open) Gazette, KOKAI No. Sho 62(1987)-215588), methods analogous to the above, methods described in the following or those used in working and referential examples given in this specification.

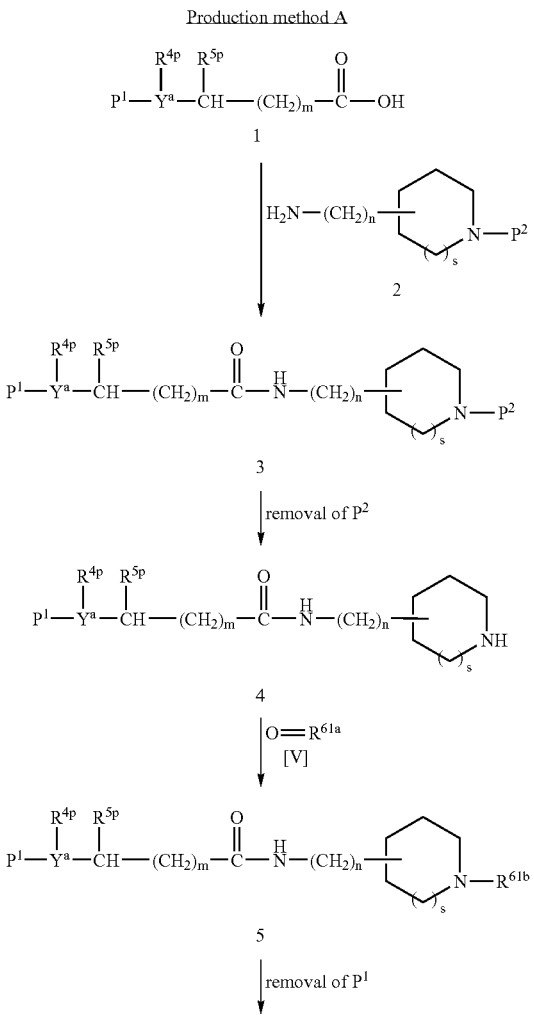

Production method A

-continued

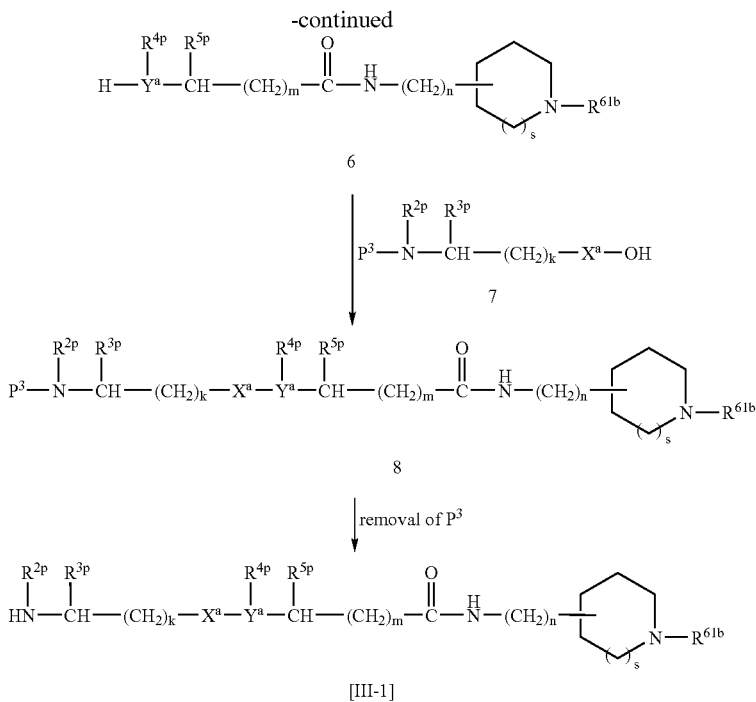

[in the above formulae, $P^1$ and $P^3$ signify protective groups of amino or imino group; $P^2$ signifies a protective group of imino group; $X^a$ signifies carbonyl group; $Y^a$ signifies nitrogen atom; and k, m, n, $R^{2p}$, $R^{3p}$, $R^{4p}$, $R^{5p}$, $R^{61a}$, $R^{61b}$ and s have the earlier defined significations].

This production method is that for producing the compounds represented by the general formula [III-1], according to which the compounds of the general formula [III-1] can be produced by the steps of having a compound of the general formula 2 act on a compound of the general formula 1 to form a compound of the general formula 3; removing therefrom the protective group $P^2$ to form a compound 4 on which a compound of the general formula [V] is acted to form a compound of the general formula 5; removing therefrom the protective group $P^1$ to form a compound 6 on which a compound of the general formula 7 is acted to form a compound of the general formula 8; and finally removing therefrom the protective group $P^3$.

The step of preparing a compound 3 from a compound 1 and that of preparing a comound 3 from a compound 1 can each be conducted similarly to the step in the production process 1 of reacting a carboxylic acid of the general formula [II] or salt or reactive derivative thereof with a compound of the general formula [III] or salt thereof, and hence the reaction conditions earlier described about the reaction can be applied.

As examples of the protective groups $P^1$, $P^2$ or $P^3$ for amino or imino group, those used as to the production process 1 can be named.

Steps for removing said protective groups can each be conducted following those methods taught in the literature references cited in respect of said production process 1.

The step of producing a compound 5 from a compound 4 can be conducted in the manner similar to the step of reacting a compound of the general formula [IV-1a] or salt thereof with a compound of the general formula [V] in the production process 2, and hence similar conditions are applicable as the reaction conditions.

Furthermore, as those compounds expressed by the general formulae 1, 2 or 7, either thosechemicals on the market may be used or they may be prepared according to known processes, those described in the working or referential examples given in this specification or those analogous thereto, if necessary in suitable combinations.

Production method B

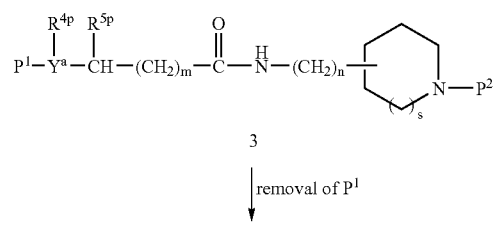

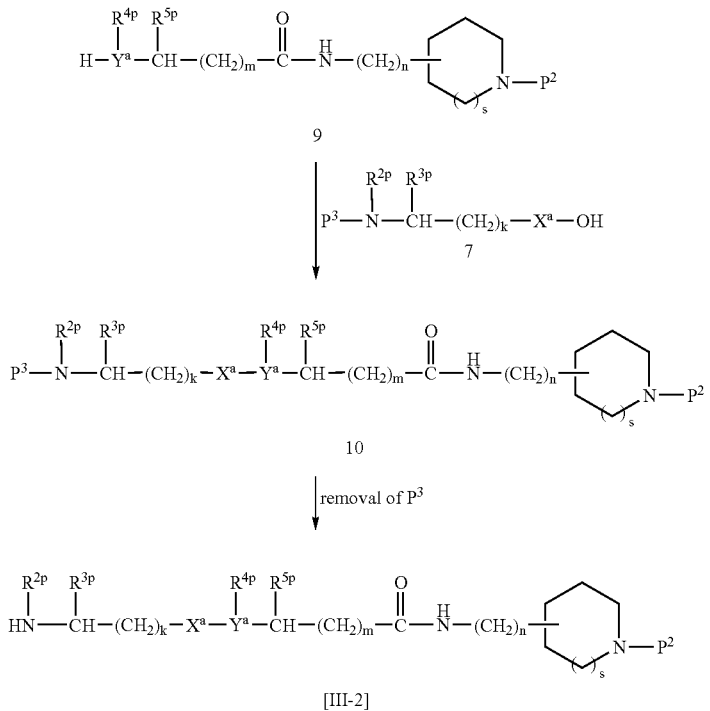

[III-2]

[in which k, m, n, $P^1$, $P^2$, $P^3$, $R^{2p}$, $R^{3p}$, $R^{4p}$, $R^{5p}$, s, $X^a$ and $Y^a$ have the earlier defined significations].

This production method is that for preparing the compounds represented by the general formula [III-2]. According to this method, the compounds of the general formula [III-2] can be produced by the steps of converting a compound of the general formula 3 to one of the general formula 9 by removing the protective group $P^1$ from the former; having a compound of the general formula 7 act on said compound 9 to form a compound of the general formula 10; and finally removing the protective group $P^3$ from said compound 10.

The step of preparing a compound 10 from a compound 9 can be conducted similarly to the step in the production process 1 of reacting a carboxylic acid of the general formula [II] or salt or reactive derivative thereof with a compound of the general formula [III] or salt thereof, and hence the reaction conditions earlier described about the reaction can be applied.

Steps for removing the protective groups of amino or imino, which are expressed as $P^1$ or $P^3$ can each be conducted following those methods taught in the literature references cited in respect of said production process 1.

Production method C

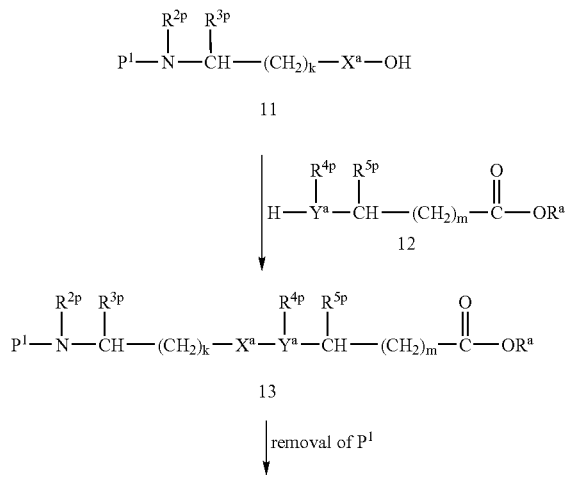

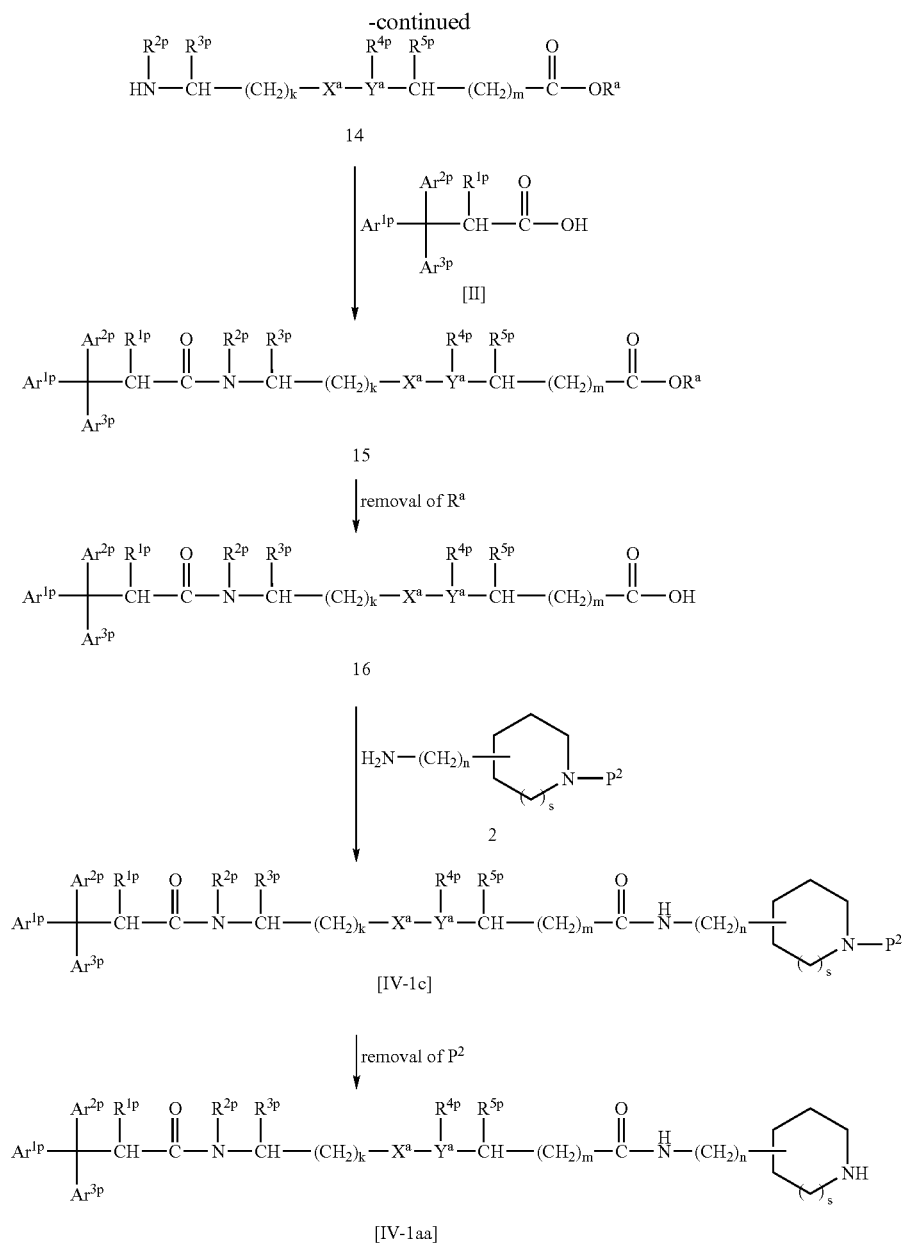

[in which $R^a$ stands for lower alkyl; and $Ar^{1p}$, $Ar^{2p}$, $Ar^{3p}$, k, m, n, $P^1$, $P^2$, $R^{1p}$, $R^{2p}$, $R^{3p}$, $R^{4p}$, $R^5$p, s, $X^a$ and $Y^a$ have the earlier defined significations]

This production method is that for producing the compounds represented by the general formula [IV-1aa], according to which the compounds of the general formula [IV-1aa] can be produced by the steps of having a compound of the general formula 12 act on a compound of the general formula 11 to form a compound of the general formula 13; removing therefrom the protective group $P^1$ to form a compound 14 on which a compound of the general formula [II] is acted to form a compound of the general formula 15; removing therefrom the lower alkyl $R^a$ to form a compound 16 on which a compound of the general formula 2 is acted to form a compound of the general formula [IV-1c]; and finally removing therefrom the protective group $P^2$.

The step of preparing a compound 13 from a compound 11 that of preparing a compound 15 from a compound 14 and that of preparing a compound [IV-1c] from a compound 16 can each be conducted similarly to the step in the production process 1 of reacting a carboxylic acid of the general formula [II] or salt or reactive derivative thereof with a compound of the general formula [III] or salt thereof, and hence the reaction conditions earlier described about the reaction can be applied.

Steps for removing said protective groups of amino or imino, which are expressed as $P^1$ or $P^2$, and for removing the lower alkyl expressed as $R^a$ can each be conducted following those methods taught in the literature references cited in respect of said production process 1.

Furthermore, as those compounds expressed by the general formulae 11 or 12, either thosechemicals on the market may be used or they may be prepared according to known processes, those described in the working or referential examples given in this specification or those analogous thereto, if necessary in suitable combinations.

Utility of those compounds of the present invention is demonstrated by the following results of the tests on inhibition of binding to muscarinic receptors and those on antagonism against various muscarinic receptors.

Tests on Inhibition of Binding to Muscarinic Receptors

These tests were performed according to a modification of the method of Hargreaves, et al. (*Br. J. Pharmacol.* 107: 494-501, 1992). Namely, muscarinic acetylcholine receptors of human $m_1$, $m_2$, $m_3$, $m_4$ and $m_5$ expressed in CHO cells (Receptor Biology, Inc.) were incubated with 0.2 nM [$^3$H]-N-methylscopolamine (82Ci/mmol, New England Nuclear, Inc.) and a test compound to be tested in 0.5 ml of 50 mM Tris-HCl, 10 mM $MgCl_2$, 1 mM EDTA solution (pH 7.4) for 120 minutes at room temperature (about 20-25° C.), followed by suction filtration over a glass filter (UniFilter plate-GF/C; Packard). Then the filter was washed four times with 1 ml of ice-cold Tris-HCl buffer and dried at 50° C. for an hour. After adding a scintillator (Microscinti 0; Packard), the radioactivity of [$^3$H]-N-methylscopolamine binding to the filter was counted with a microplate scintillation counter (TopCount™; Packard). Non-specific receptor binding of [$^3$H]-N-methylscopolamine was measured by adding 1 μM N-methylscopolamine. According to the method of Cheng and Prusoff (*Biochem. Pharmacol.* 22: 3099-3108, 1973), the binding affinity of a compound of the present invention for muscarinic receptors is expressed by dissociation constant (Ki) which is calculated from the concentration ($IC_{50}$) of the test compound which achieves 50% inhibition of binding of [$^3$H]-N-methylscopolamine, the labeled ligand. The results are shown in Tables 1-1 and 1-2.

Tests for Antagonism to Muscarinic Receptors (in vitro)

1) Test for Antagonism to $M_2$ Receptor in Isolated Rat Right Atrium

The test was performed according to a conventional method. Male SD strain rats (weighing 300-500 g) were killed by exsanguination, and from each of them the right atrium was isolated. Each preparation was isometrically suspended in a Magnus tube filled with 20 ml of Krebs-Henseleit solution (gassed with 95% $O_2$-5% $CO_2$ and kept at 32° C.) with an initial tension of 0.5 g. The heart rate was recorded with a heart rate counter. After the preparation was equilibrated for 30 minutes, carbachol ($10^{-9}$ to $10^{-6}$ M) was cumulatively administered from a low concentration to three-fold increasing doses and accompanying decrease in heart rate was measured to obtain a dose-responsecurve for the control experiment. After the preparation was washed with fresh solution to restore the heart rate, a test compound was administered thereto. Ten minutes later, carbachol was cumulatively administered again. Responses to carbachol were expressed as percentages based on the heart rate before administration of carbachol as 100%. The antagonistic potency ($K_B$ value) of the test compound was determined from the degree of shift of the dose-responsecurve attributable to the treatment with individual test compound of the present invention. The results were as shown in Tables 2-1 and 2-2.

2) Test for Antagonism to the Airway $M_3$ Receptor in Isolated Rat Trachea

The test was performed according to a conventional method. Male SD strain rats (weighing 300-500 g) were killed by exsanguination, and from each of them the trachea was isolated. Annular segments (2 mm wide) were cut out from the trachea and cut transversely at the anterior cartilage part to make open ring preparation. Each preparation was suspended in a Magnus tube filled with 5 ml of Krebs-

TABLE 1-1

Inhibitory Effects on Binding to Muscarinic $m_1$, $m_2$, $m_3$, $m_4$ and $m_5$ Receptors

| Compound | Ki(nM) | | | | | Selectivity (times) | | | |
| --- | --- | --- | --- | --- | --- | --- | --- | --- | --- |
| | $m_1$ | $m_2$ | $m_3$ | $m_4$ | $m_5$ | $m_1/m_3$ | $m_2/m_3$ | $m_4/m_3$ | $m_5/m_3$ |
| Example 6 | 860 | 250 | 1.8 | 66 | 82 | 480 | 140 | 37 | 46 |
| Example 12 | 140 | 34 | 0.38 | 18 | 32 | 370 | 89 | 47 | 84 |
| Example 19 | 270 | 30 | 0.75 | 8.1 | 19 | 360 | 40 | 11 | 25 |
| Example 28 | 130 | 85 | 1.2 | 36 | 220 | 110 | 71 | 30 | 180 |

TABLE 1-2

Inhibitory Effects on Binding to Muscarinic $m_1$, $m_2$, $m_3$, $m_4$ and $m_5$ Receptors

| Compound | Ki(nM) | | | | | Selectivity (times) | | | |
| --- | --- | --- | --- | --- | --- | --- | --- | --- | --- |
| | $m_1$ | $m_2$ | $m_3$ | $m_4$ | $m_5$ | $m_1/m_3$ | $m_2/m_3$ | $m_4/m_3$ | $m_5/m_3$ |
| Example 133 | >2500 | 810 | 3.2 | 140 | 1600 | >780 | 250 | 44 | 500 |
| Example 144 | 110 | 110 | 1.3 | 27 | 230 | 85 | 85 | 21 | 180 |
| Example 146 | 1200 | 1000 | 15 | 360 | 490 | 80 | 67 | 24 | 33 |
| Example 150 | 150 | 490 | 4.7 | 310 | 850 | 32 | 100 | 66 | 180 |
| Example 151 | 450 | 460 | 3.5 | 74 | 890 | 130 | 130 | 21 | 250 |

As is clear from the results indicated in above Tables 1-1 and 1-2, those compounds of the present invention exhibited far higher binding-inhibitory activity to $m_3$ receptor, than to $m_1$, $m_2$, $m_4$ and $m_5$ receptors.

Henseleit solution (gassed with 95% $O_2$-5% $CO_2$ and kept at 32° C.) with an initial tension of 1.0 g and a resting tension of 0.6 g. The tension of the preparation was recorded isometrically. After being equilibrated for an hour, the preparation was made to contract twice by treatment with $10^{-4}$ M carbachol, and the second contraction induced by carbachol was used as the reference contraction. After washing the preparation with fresh solution to restore it to the base line, a test compound was administered thereto (or no treatment was given). Ten minutes later, carbachol ($10^{-8}$ to $10^{-3}$ M) was cumulatively administered in three-fold increasing doses to obtain a dose-response curve. The dose-responsecurve was plotted by expressing responses as percentages based on the reference contraction of the preparation as 100%. The antagonistic potency ($K_B$ value) of the test compound was determined from the degree of shift of the dose-responsecurve attributable to the treatment with the test compound. The results were as shown in Tables 2-1 and 2-2.

TABLE 2-1

Antagonism to Muscarinic Receptors (in vitro)

| Compound | $K_B$(nM) | | Selectivity (times) |
| --- | --- | --- | --- |
|  | Right Atrium $M_2$ | Trachea $M_3$ | $M_2/M_3$ |
| Example 12 | 160 | 2.3 | 70 |

TABLE 2-2

Antagonism to Muscarinic Receptors (in vitro)

| Compound | $K_B$(nM) | | Selectivity (times) |
| --- | --- | --- | --- |
|  | Right Atrium $M_2$ | Trachea $M_3$ | $M_2/M_3$ |
| Example 133 | 41 | 0.71 | 58 |

As is clear from the results indicated in above Tables 2-1 and 2-2, the compounds of the present invention exhibited far more powerful antagonism to the trachea $M_3$ receptor than to the right atrium $M_2$ receptor. Therefore, the compounds of the present invention are more selective for trachea $M_3$ receptor.

Tests for Antagonism Against Muscarinic Receptors (in vivo)

1) Test for Antagonism to $M_1$ Receptor (Inhibitory Effects on McNeil-A-343-induced Vasopressor Reaction in Cervical Vertebrae-separated Rats)

Male SD strain rats (weighing 300-500 g) were anesthetized with intraperitoneal administration of pentobarbital (50 mg/kg). Each rat's airway was cannulated by laryngotomy. Also by femoral incision, femoral artery and vein were isolated each and cannulated, which were used as routes for heart rate counting and chemical administration, respectively. Using a pulmotor for small animals (Type 7025, Ugo Basile Co.), artificial respiration was conducted under the conditions of ventilation rate of 6 ml/kg per breath and respiration rate of 90 breaths/min. The heart rate and blood pressure variations were measured with a heart rate counter (AT-601 G, Nippon Koden Co.) and a tonometer (AP-641G, Nippon Koden Co.), via a pressure transducer (DX-312, Nippon Koden Co.). After the blood pressure was stabilized, the cervical vertebrae was separated with an injection needle pricked from the occipital region. After the average blood pressure dropped to not higher than 70 mmHg, test compound (test compound-treated group) or isotonic sodium chloride solution (control group) was intravenously administered. Five (5) minutes thereafter, McNeil-A-343 (0.3 mg/kg) was intravenously administered, and whereby induced hypertension variation was recorded. In this experiment one-dose evaluation per one animal was conducted. The inhibitory effect (inhibition ratio) of the test compound on the McNeil-A-343-induced vasopressor reaction was determined by the following equation:

Inhibition ratio (%) =

$$\left(1 - \frac{\text{blood pressure variation in test compound-treated group}}{\text{blood pressure variation in control group}}\right) \times 100$$

The 50% inhibition dose ($ED_{50}$; μg/kg) was calculated from the inhibition ratio of each dose of the tested compound. The results were as shown in Tables 3-1 and 3-2 as the antagonism to $M_1$ receptor of the tested compounds.

2) Test for Antagonism to $M_2$ Receptor (Inhibitory Effects to Acetylcholine-induced Bradycardia Reaction in Rats)

Male SD strain rats (weighing 300-500 g) were anesthetized with urethane (1 g/kg) and α-chloralose (50 mg/kg) administered intraperitoneally. The airway, carotid artery and vein of each rat were isolated by laryngotomy and cannulated. The carotid artery and vein cannulae were made the routes for heart rate counting and drug administration. After suppressing the rats' spontaneous respiration by hypodermic administration of succinylcholine (5 mg/body), artificial ventilation was conducted under the conditions of ventilation rate of 6 ml/kg per breath and respiration rate of 90 breaths/min., using a pulmotor for small animals (Model 681, Harvard Co.). The variations in heart rate and blood pressure were measured with a heart rate counter (AP-601G, Nippon Koden Co.) and a tonometer (AP-641G, Nippon Koden Co.), via a pressure transducer (DX-312, Nippon Koden Co.). After about 10 minutes' stabilization period, heart rate change was induced by intravenous administration of acetylcholine (10 μg/kg), and the mean value of the change was recorded as the value before the drug administration (pre-value) of the body. After calculating the pre-values, the test compound (test compound-treated group) or isotonic sodium chloride solution (control group) was intravenously administered. Five minutes thereafter, acetylcholine was intravenously administered and whereby induced change in the heart rate was recorded. In this experiment, one-dosage evaluation was conducted per one animal of the tested rats. The change in acetylcholine-induced bradycardia reaction (% of pre-value) caused by the test compound and isotonic sodium chloride solution was determined by the following Equatin 1:

Equation 1:

Percent of pre-value =

$$\frac{\text{heart rate change after administration of test compound (isotonic sodium chloride solution)}}{\text{heat rate change before administration (pre-value) of test compound (isotonic sodium chloride solution)}} \times 100$$

The inhibitory effect (inhibition ratio) of each test compound on the acetylcholine-induced bradycardia reaction was determined according to the following Equation 2:

Equation 2:

Inhibition ratio (%) =

$$\left(1 - \frac{\text{\% of pre-value (test compound-treated group)}}{\text{\% of pre-value (control group)}}\right) \times 100$$

Fifty (50%) inhibition dose ($ED_{50}$; μg/kg) was calculated from the inhibition ratio of each dose of the tested compound.

The results were as shown in Tables 3-1 and 3-2 as the antagonism to $M_2$ receptor of tested compounds.

3) Test for Antagonism to Muscarinic $M_3$ Receptor (Inhibitory Effects on Acetylcholine-induced Airway Resistance-increasing Reaction in Rats)

Male SD strain rats (weighing 300-500 g) were anesthetized with urethane (1 g/kg) and α-chloralose (50 mg/kg) administered intraperitoneally. The airway and carotid artery of each rat were isolated by laryngotomy and cannulated. The carotid artery cannula was used as the test compound administration route. After suppressing spontaneous respiration by hypodermic administration of succinylcholine (5 mg/body), the rats were transferred into Plethysmograph-box (PLYAN, Buxco) and artificially ventilated under the conditions of ventilation rate of 6 ml/kg per breath and respiration rate of 90 breaths/min., using a pulmotor for small animals (Model 681, Harvard Co.). Measurements of air rate and intracellular pressure, calculation of airway resistance and lung compliance and their recording were conducted with lung function analyzer (Model 6, Buxco). After about 10 minutes' stabilization period, the change in airway resistance induced by intravenous administration of acetylcholine (50 μg/kg) was measured twice at 5 minutes' interval. The change in airway resistance induced by the second acetylcholine administration was recorded as the pre-administration of the tested rat (pre-value). Five (5) minutes afterthe second acetylcholine-induced reaction measurement, the test compound or isotonic sodium chloride solution was intravenously administered. Five (5) minutes thereafter, acetylcholine was administered and whereby induced airway resistance change was measured. In this experiment, one-dosage evaluation was conducted per one animal of the tested rats. The changes in acetylcholine-induced airway resistance-increasing reaction (% of pre-value) caused by the tested compound and isotonic sodium chloride solution were calculated by the following Equation 1:

Equation 1:

$$\text{Percent of pre-value} = \frac{\text{change in airway resistance after administration of test compound (isotonic sodium chloride solution)}}{\text{change in airway resistance before administration of test compound (isotonic sodium chloride solution)}} \times 100$$

The inhibitory effect (inhibition ratio) of each test compound on the acetylcholine-induced airway resistance-increasing reaction was determined according to the following Equation 2.

Equation 2:

$$\text{Inhibition ratio (\%)} = \left(1 - \frac{\text{\% of pre-value (test compound-treated group)}}{\text{\% of pre-value (control group)}}\right) \times 100$$

Fifty (50)% inhibition dose (ED50; μg/kg) was calculated from the inhibition ratio of each dose of the tested compound. The results were as shown in Tables 3-1 and 3-2 as the antagonism to $M_3$ receptor of the tested compounds.

TABLE 3-1

Antagonism to Muscarinic Receptors (in vivo)

$ED_{50}$ (μg/kg, i.v.)

| Compound | vaso-pressor $M_1$ | bradycardia $M_2$ | Airway constriction $M_3$ | Selectivity (times) $M_1/M_3$ | $M_2/M_3$ |
|---|---|---|---|---|---|
| Example 12 | >3000 | 1550 | 15 | >200 | 100 |
| atoropine | 19 | 5.2 | 4.3 | 4.4 | 1.2 |

TABLE 3-2

Antagonism to Muscarinic Receptors (in vivo)

$ED_{50}$ (μg/kg, i.v.)

| Compound | vaso-pressor $M_1$ | bradycardia $M_2$ | Airway constriction $M_3$ | Selectivity (times) $M_1/M_3$ | $M_2/M_3$ |
|---|---|---|---|---|---|
| Example 133 | >300 | 114 | 2.1 | >143 | 54 |
| atoropine | 19 | 5.2 | 4.3 | 4.4 | 1.2 |

As is clear from the results as shown in above Tables 3-1 and 3-2, the compounds of the present invention exhibited high $M_3$ selectivity also in vivo.

4) Test for Antagonism to $M_3$ Receptor (Bronchodilation in Anesthetized Dogs)

The bronchodilation action of inhaled test compound was evaluated by measuring the compounds' inhibitory action on respiratory resistance-increasing reaction induced by a methacholine provocation test. For the experiment, 12 to 36 months old male beagle dogs (weighing 10-15 kg) were used. After being anesthetized by intravenous pentobarbital administration (30 mg/kg), the dogs were intubated cannulae in their trachea. After their respiration became stable, the cannulae were connected with Astograph (TCK-6100H, Chest) and a methacholine provocation test by 3 Hz oscillation method was conducted. The inhaling inducer, methacholine, was diluted with isotonic sodium chloride solution in 10-grade concentration levels starting from 40,000 μg/ml, successively as 20,000 to 10,000, 5,000, 2500, 1250, 625, 312.5, 156 and 78 μg/ml. The dogs were caused to inhale these methacholine solutions each for one minute starting from the one of low concentration with the nebulizer in the Astograph, and changes in respiratory resistance were continuously plotted. The methacholine concentration at which the respiratory resistance increased to twice the initial value was recorded as the methacholine reaction threshold value. Before evaluating the test compounds, the methacholine reaction threshold value[1]) under no drug treatment was measured at least twice at a week's interval, to select the dogs showing reproducible reaction.

The inhaling administration of each test compound (1 mg/ml) was conducted for 10 minutes under pentobarbital anesthetization (30 mg/kg, i.v.), with the nebulizer in the Astograph. Thereafter pentobarbital was additionally administered when necessary, to maintain the anesthetized condition. Four hours afterthe administration, a methacholine provocation test was conducted, to measure the methacholine reaction threshold value[2]) after administration of each test compound. The bronchodilator activity (shift value) of each tested compound was determined according to the following equation:

Shift value =

$$\frac{\text{methacholine reaction threshold value}^{1)}}{\text{methacholine reaction threshold value}^{2)}}$$
$$\text{after drug administration}$$
$$\text{without drug administration}$$

TABLE 4

Antagonism to Muscarinic Receptor
(in vivo: Anesthetized Dogs)

| Compound | Shift (fold) Airway constriction $M_3$ |
|---|---|
| Example 133 | 20.2 |
| Example 151 | >40.0 |

As is clearly demonstrated in above Table 4, the compounds of the present invention exhibited powerful bronchodilation action and long duration of the action.

As above, the compounds of formula [I] of the present invention exhibit potent and selective antagonistic activity against muscarinic $M_3$ receptor. Hence, they can be administered to patients orally or parenterally as safe pharmaceutics exhibiting little side effects, for treating, in particular, such respiratory diseases as chronic obstructive pulmonary diseases, chronic bronchitis, asthma, chronic respiratory tract obstruction, fibroid lung, pulmonary emphysema and rhinitis; digestive diseases such as irritable bowel syndrome, convulsive colitis; gastroduodental ulcer, convulsion or hyperanakinesia of digestive tract, diverticulitis and pain accompanying contraction of smooth muscles of the digestive system; urinary diseases accompanied by dysuria like urinary incontinence, urgency and pollakiuria in nervous pollakiuria, neurogenic bladder, nocturnal enuresis, unstable bladder, cystospasm and chronic cystisis; and motion sickness.

For actual use of thosecompounds of the present invention for therapeutic treatment or prophylaxis of diseases as exemplified above, they may be combined with pharmaceutically acceptable adjuvants in the usual manner to formulate pharmaceutical preparations of forms suitable for administration. For this purpose, there can be used a variety of adjuvants which are commonly used in the field of pharmaceutics. Such adjuvants include, for example, gelatin, lactose, sucrose, titanium oxide, starch, crystalline cellulose, hydroxypropylmethylcellulosecarboxymethylcellulosecorn starch, microcrystalline wax, white petrolatum, magnesium aluminate metasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light anhydrous silicic acid, talc, vegetable oil, benzyl alcohol, gum arabic, propylene glycol, polyalkylene glycol, cyclodextrin and hydroxy-propylcyclodextrin.

The dosage forms of pharmaceutical preparations formulated using these adjuvants include solid preparations such as tablets, capsules, granules, powders and suppositories; and liquid preparations such as syrups, elixirs and injections. These preparations may be formulated according to conventional techniques well-known in the field of pharmaceutics. Liquid preparations may be in a form which is dissolved or suspended in water or other suitable medium prior to use. In particular, injections may be in the form of a solution or suspension in physiological saline solution or a glucose solution, or in powder form to be dissolved or suspended in physiological saline or a glucose solution prior to use. If desired, such injections may contain buffer agents and/or preservatives.

As preparations for oral administration, such formulation forms, besides ordinary tablets, capsules, granules, powders and the like, aerosols or dry powders for inhalation, elixiers or suspensions containing spices or coloring agents may be employed.

In these pharmaceutical preparations, a compound in accordance with the present invention may be present at a ratio of from 1.0 to 100% by weight, preferably 1.0 to 60% by weight, based on the total weight of individual preparation. These pharmaceutical preparations may additionally contain other therapeutically effective compounds.

When the compounds of the present invention are used as drugs, their dosage level and dosage schedule may vary according to the sex, age, body weight, severity of symptoms of individual patient, type and range of the desired therapeutic effect, and the like. Generally for oral administration, they are preferably administered in a daily dose of 0.1 to 100 mg/kg for adults and this daily dose may be given at a time or in several divided doses. For parenteral administration, they are preferably administered in a daily dose of 0.001 to 10 mg/kg which may be given at a time or in several divided doses.

Optimum Embodiments for Practicing the Invention

Hereinafterthe present invention is more specifically explained with reference to working examples, it being understood that the examples are in no way limitative of the scope of the invention.

EXAMPLE 1

N-(2-{3-({(3R)-1-(2-methylbutyl)-3-piperidyl}methyl)amino-3-oxopropyl}amino-2-oxo-ethyl)-3,3,3-triphenylpropanamide (Step 1)

Synthesis of ethyl 3-(2-{(tert-butoxycarbonyl)amino}-acetylamino)propionate

To a solution of 1.5 g of ethyl 3-aminopropionate monohydrochloride and 1.7 g of 2-{(tert-butoxycarbonyl) amino}acetic acid in 50 ml of chloroform, 1.6 g of 1-hydroxybenzotriazole monohydrate, 2.3 g of 1-ethyl-3-(3-dimethylaminopropyl)carbodiimide monohydrochloride and 1.4 ml of triethylamine were added at room temperature by the order stated, and stirred for 2 hours at the same temperature. The reaction liquid was diluted with chloroform, and washed successively with saturated aqueous sodium bicarbonate solution, 10% aqueous citric acid solution and saturated saline solution, by the order stated, and dried on anhydrous magnesium sulfate. The solvent was distlled off under reduced pressure, and the resultant residue was purified by means of silica gel column chromatography (eluting solvent: hexane/ethyl acetate=1/4) to provide 2.0 g of the title compound.

(Step 2)

Synthesis of ethyl 3-{(2-aminoacetyl)amino}propionate monohydrochloride 2.0 Grams of ethyl 3-(2-{(tert-butoxycarbonyl)amino}-acetylamino)propionate were dissolved in 30 ml of 10% hydrochloric acid-methanol and stirred for 15 hours at room temperature. Upon distilling the reaction liquid off under reduced pressure, 1.52 g of the title compound was obtained.

(Step 3)

Synthesis of ethyl 3-(2-{(3,3,3-triphenylpropanoyl)amino}-acetylamino)propionate To a solution of 1.52 g of ethyl 3-{(2-aminoacetyl)amino}-propionate monohydrochloride and 2.18 g of 3,3,3-triphenylpropionic acid in 20 ml of chloroform, 1.46 g of 1-hydroxybenzotriazole monohydrate, 2.07 g of 1-ethyl-3-(3-dimethylaminopropyl)carbodiimide monohydrochloride and 2.0 ml of triethylamine were successively added at room temperature by the order stated, followed by 2 hours' stirring at the same temperature. The reaction liquid was diluted with ethyl acetate and washed successively with aqueous saturated sodium bicarbonate solution, 1N-hydrochloric acid and water, and filtered through cerite. The filtrate was dried on anhydrous magnesium sulfate. The solvent was distilled off under reduced pressure, and the resultant residue was purified by means of silica gel column chromatography (eluting solvent: hexane/ethyl acetate=4/1-chloroform/methanol=10/1) to provide 1.7 g of the title compound.

(Step 4)

Synthesis of 3-(2-{(3,3,3-triphenylpropanoyl)amino}acetylamino)propionic acid 1.7 Grams of ethyl 3-(2-{(3,3,3-triphenylpropanoyl)amino}-acetylamino)propionate was dissolved in a mixed liquid consisting of 70 ml of tetrahydrofuran and 20 ml of methanol. To the solution 5.0 ml of 4N aqueous sodium hydroxide solution was added at room temperature, followed by an hour's stirring at the same temperature. The reaction liquid was distilled off under reduced pressure, and the residue was rendered acidic by addition of 1N hydrochloric acid, extracted with ethyl acetate, washed with saturated saline solution and dried over anhydrous magnesium sulfate. Upon distilling the solvent off under reduced pressure, 1.10 g of the title compound was obtained.

(Step 5)

Synthesis of N-(2-{3-({(3R)-1-(tert-butoxycarbonyl)-3-pyperidyl}methyl)amino-3-oxopropyl}amino-2-oxoethyl)-3,3,3-triphenylpropanamide To a solution of 0.55 g of (3R)-3-aminomethyl-1-(tert-butoxycarbonyl)piperidine and 1.1 g of 3-(2-{(3,3,3-triphenylpropanoyl)amino}acetylamino)propionic acid in 10 ml of N,N-dimethylformamide, 0.52 g of 1-hydroxybenzotriazole monohydrate and 0.75 g of 1-ethyl-3-(3-dimethylaminopropyl) carbodiimide monohydrochloride were successively added at room temperature, and stirred for 2 hours at the same temperature. Then 2.0 ml of triethylamine and 10 ml of chloroform were added at room temperature, followed by an hour's stirring. The reaction liquid was distilled off under reduced pressure, diluted with ethyl acetate, washed successively with saturated aqueous sodium bicarbonate solution, 10% aqueous citric acid solution and saturated saline solution, and dried over anhydrous magnesium sulfate. The solvent was distilled off under reduced pressure and the residue was purified by means of silica gel column chromatography (eluting solvent: chloroform/methanol=19/1) to provide 1.41 g of the title compound.

(Step 6)

Synthesis of N-(2-{3-((3S)-3-piperidylmethyl)amino-3-oxopropyl}amino-2-oxoethyl)-3,3,3-triphenylpropanamide monohydrochloride Using N-(2-{3-({(3R)-1-(tert-butoxycarbonyl)-3-piperidyl}methyl)amino-3-oxopropyl}amino-2-oxoethyl)-3,3,3-triphenylpropanamide, the title compound was prepared by a method similar to Step 2 of Example 1.

(Step 7)

Synthesis of N-(2-{3-({(3R)-1-(2-methylbutyl)-3-piperidyl}-methyl)amino-3-oxopropyl}amino-2-oxoethyl)-3,3,3-triphenylpropanamide To a solution of 200 mg of N-(2-{3-((3S)-3-piperidylmethyl)amino-3-oxopropyl}amino-2-oxoethyl)-3,3,3-triphenylpropanamide monohydrochloride in 10 ml of tetrahydrofuran, 0.10 ml of 2-methylbutanal and 230 mg of sodium triacetoxyborohydrate were successively added at room temperature, followed by 2 hours' stirring at the same temperature. The reaction liquid was diluted with ethyl acetate, washed successively with saturated aqueous sodium bicarbonate solution and saturated saline solution, and dried over anhydrous magnesium sulfate. The solvent was distilled off under reduced pressure and the resultant residue was purified by means of silica gel column chromatography (eluting solvent: chloroform/methanol=19/1-4/1), to provide 158 mg of the title compound as a colorless solid.

$^1$H-NMR(CDCl$_3$, δppm): 0.89(3H, d, J=6.6 Hz), 0.90 (3H, d, J=6.6 Hz), 0.95-1.20(2H, m), 1.32-1.50(1H, m), 1.50-2.42 (11H, m), 2.60-2.95(2H, m), 3.05-3.25(2H, m), 3.34-3.50 (2H, m), 3.55(2H, d, J=6.6 Hz), 3.56-3.72(2H, m), 5.75-5.98 (1H, m), 6.29-6.65(2H, m), 7.10-7.38(15H, m)

FAB-MS(m/e, as (C$_{37}$H$_{48}$N$_4$O$_3$+H)$^+$): 597

EXAMPLE 2

N-(2-{3-({(3R)-1-(2-ethylbutyl)-3-piperidyl}methyl)amino-3-oxopropyl}amino-2-oxoethyl)-3,3,3-triphenylpropanamide The title compound was prepared by a method similar to Step 7 of Example 1, using 2-ethylbutanal. The product was obtained in the form of a colorless solid.

$^1$H-NMR(CDCl$_3$, δppm): 0.85(6H, t, J=7.4 Hz), 0.94-2.46 (16H, m), 2.75-3.01(2H, m), 3.01-3.22(2H, m), 3.32-3.43 (2H, m), 3.56(2H, d, J=5.6 Hz), 3.58-3.71(2H, m), 5.80-6.05 (1H, m), 6.33-6.75(2H, m), 7.13-7.40(15H, m)

FAB-MS(m/e, as (C$_{38}$H$_{50}$N$_4$O$_3$+H)$^+$): 611

EXAMPLE 3

N-(2-{3-({(3R)-1-(2-methylpentyl)-3-piperidyl}methyl)amino-3-oxopropyl}amino-2-oxoethyl)-3,3,3-triphenylprepanamide The title compound was prepared by a method similar to Step 7 of Example 1, using 2-methylpentanal. The product was obtained in the form of a colorless solid.

$^1$H-NMR(CDCl$_3$, δppm): 0.80-0.98(6H, m), 0.98-1.18 (2H, m), 1.18-1.50(4H, m), 1.51-1.99(10H, m), 2.65-3.26 (4H, m), 3.30-3.49(2H, m), 3.56(2H, d, J=5.4 Hz), 3.65 (1H, d, J=15.8 Hz), 3.66(1H, d, J=15.8 Hz), 5.80-6.15(1H, m), 6.32-6.75(2H, m), 7.12-7.40(15H, m)

FAB-MS(m/e, as (C$_{38}$H$_{50}$N$_4$O$_3$+H)$^+$): 611

EXAMPLE 4

N-{2-(3-{((3R)-1-propyl-3-piperidyl)methyl}amino-3-oxopropyl)amino-2-oxoethyl}-3,3,3-triphenylpropanamide The title compound was prepared by a method similar to Step 7 of Example 1, using propionaldehyde. The product was obtained in the form of a colorless solid.

$^1$H-NMR(CDCl$_3$, δppm): 0.88(3H, t, J=7.4 Hz), 0.82-1.05 (1H, m), 1.21-2.05(8H, m), 2.20-2.45(4H, m), 2.69-2.91(2H, m), 2.98-3.25(2H, m), 3.32-3.45(2H, m), 3.49 (1H, dd, J=5.5, 16.7 Hz), 3.60(1H, dd, J=5.5, 16.7 Hz), 3.63 (1H, d, J=14.9 Hz), 3.65(1H, d, J=14.9 Hz), 5.75-5.90(1H, m), 5.90-6.10 (1H, m), 6.20-6.32(1H, m), 7.15-7.37(15H, m)

FAB-MS(m/e, as $(C_{35}H_{44}N_4O_3+H)^+$): 569

EXAMPLE 5

N-{2-(3-{((3R)-1-butyl-3-piperidyl)methyl}amino-3-oxopropyl)amino-2-oxoethyl}-3,3,3-triphenylpropanamide The title compound was prepared by a method similar to Step 7 of Example 1, using n-butylaldehyde. The product was obtained in the form of a colorless solid.

$^1$H-NMR(CDCl$_3$, δppm): 0.91(3H, t, J=7.3 Hz), 0.80-2.06 (10H, m), 2.10-2.64(5H, m), 2.90-3.30(4H, m), 3.37(2H, q, J=5.9 Hz), 3.45-3.65(2H, m), 3.64 (1H, d, J=15.1 Hz), 3.67 (1H, d, J=15.1 Hz), 6.31-6.49(1H, m), 6.58-6.83(2H, m), 7.10-7.40(15H, m)

FAB-MS(m/e, as $(C_{36}H_{46}N_4O_3+H)^+$): 583

EXAMPLE 6

N-{2-(3-{((3R)-1-pentyl-3-piperidyl)methyl}amino-3-oxopropyl)amino-2-oxoethyl}-3,3,3-triphenylpropanamide The title compound was prepared by a method similar to Step 7 of Example 1, using valeraldehyde. The product was obtained in the form of a colorless solid.

$^1$H-NMR(CDCl$_3$, δppm): 0.89(3H, t, J=6.9 Hz), 0.91-2.70 (17H, m), 2.96-3.25(4H, m), 3.37(2H, q, J=6.0 Hz), 3.57(2H, d, J=5.4 Hz), 3.65(1H, d, J=15.1 Hz), 3.66 (1H, d, J=15.1 Hz), 6.53(1H, t, J=5.4 Hz), 6.84(1H, t, J=5.8 Hz), 6.92(1H, t, J=5.3 Hz), 7.09-7.36(15H, m)

FAB-MS(m/e, as $(C_{37}H_{48}N_4O_3+H)^+$): 597

EXAMPLE 7

N-{2-(3-{((3R)-1-hexyl-3-piperidyl)methyl}amino-3-oxopropyl)amino-2-oxoethyl}-3,3,3-triphenylpropanamide The title compound was prepared by a method similar to Step 7 of Example 1, using n-hexanal. The product was obtained in the form of a colorless solid.

$^1$H-NMR(CDCl$_3$, δppm): 0.88(3H, t, J=6.7 Hz), 0.91-1.82 (11H, m), 1.95-2.70(8H, m), 2.95-3.20(4H, m), 3.37(2H, q, J=6.0 Hz), 3.57(2H, d, J=5.7 Hz), 3.65 (1H, d, J=15.0 Hz), 3.67(1H, d, J=15.0 Hz), 6.38-6.50(1H, m), 6.67-6.88(2H, m), 7.10-7.37(15H, m)

FAB-MS(m/e, as $(C_{38}H_{50}N_4O_3+H)^+$): 611

EXAMPLE 8

N-{2-(3-{((3R)-1-heptyl-3-piperidyl)methyl}amino-3-oxopropyl)amino-2-oxoethyl}-3,3,3-triphenylpropanamide The title compound was prepared by a method similar to Step 7 of Example 1, using n-heptanal. The product was obtained in the form of a colorless solid.

$^1$H-NMR(CDCl$_3$, δppm): 0.88(3H, t, J=6.7 Hz), 0.90-2.70 (21H, m), 2.95-3.18(4H, m), 3.38(2H, q, J=6.1 Hz), 3.55(1H, dd, J=5.6, 16.5 Hz), 3.59(1H, dd, J=5.6, 16.5 Hz), 3.65(1H, d, J=15.1 Hz), 3.67(1H, d, J=15.1 Hz), 6.39 (1H, t, J=5.3 Hz), 6.59-6.85(2H, m), 7.10-7.38(15H, m)

FAB-MS(m/e, as $(C_{39}H_{52}N_4O_3+H)^+$): 625

EXAMPLE 9

N-{2-(3-{((3R)-1-octyl-3-piperidyl)methyl}amino-3-oxopropyl)amino-2-oxoethyl}-3,3,3-triphenylproyanamide The title compound was prepared by a method similar to Step 7 of Example 1, using n-octanal. The product was obtained in the form of a colorless solid.

$^1$H-NMR(CDCl$_3$, δppm): 0.80-2.73(23H, m), 0.88 (3H, t, J=6.7 Hz), 2.90-3.25(4H, m), 3.29-3.48(2H, m), 3.59 (2H, d, J=5.6H), 3.65(1H, d, J=15.1 Hz), 3.68 (1H, d, J=15.1 Hz), 6.25-6.42(1H, m), 6.51-6.5(2H, m), 7.10-7.38(15H, m)

FAB-MS(m/e, as $(C_{40}H_{54}N_4O_3+H)^+$): 639

EXAMPLE 10

N-{2-(3-{((3R)-1-nonyl-3-piperidyl)methyl}amino-3-oxopropyl)amino-2-oxoethyl}-3,3,3-triphenylpropanamide The title compound was prepared by a method similar to Step 7 of Example 1, using n-nonanal. The product was obtained in the form of a colorless solid.

$^1$H-NMR(CDCl$_3$, δppm): 0.88(3H, t, J=6.6 Hz), 0.80-2.73 (25H, m), 2.90-3.25(4H, m), 3.28-3.50(2H, m), 3.59(2H, d, J=5.6 Hz), 3.65(1H, d, J=15.2 Hz), 3.68 (1H, d, J=15.2 Hz), 6.18-6.40(1H, m), 6.48-6.85(2H, m), 7.07-7.56(15H, m)

FAB-MS(m/e, as $(C_{41}H_{56}N_4O_3+H)^+$): 653

EXAMPLE 11

N-{2-(3-{((3R)-1-decyl-3-piperidyl)methyl}amino-3-oxopropyl)amino-2-oxoethyy}-3,3,3-triphenylpropanamide The title compound was prepared by a method similar to Step 7 of Example 1, using n-decanal. The product was obtained in the form of a colorless solid.

$^1$H-NMR(CDCl$_3$, δppm): 0.78-2.71(30H, m), 2.88-3.25 (4H, m), 3.37(2H, q, J=5.9 Hz), 3.57(2H, d, J=5.6 Hz), 3.65 (1H, d, J=5.0 Hz), 3.67(1H, d, J=5.0 Hz), 6.49(1H, t, J=5.3 Hz), 6.75-6.95(2H, m), 7.11-7.40(15H,m)

FAB-MS(m/e, as $(C_{42}H_{58}N_4O_3+H)^+$): 667

EXAMPLE 12

N-{2-(3-{((3R)-1-cyclohexylmethyl-3-piperidyl) methyl}amino-3-oxopropyl)amino-2-oxoethyl}-3,3, 3-triphenyloropanamide The title compound was prepared by a method similar to Step 7 of Example 1, using cyclohexanecarbaldehyde. The product was obtained in the form of a white solid.

$^1$H-NMR(CDCl$_3$, δppm): 0.81-1.80(17H, m), 1.97-2.08 (3H, m), 2.28-2.32(2H, m), 2.59-2.65(2H, m), 3.12-3.17(2H, m), 3.37-3.46(2H, m), 3.51-3.55(2H, m), 3.64(2H, s), 5.60-5.64 (1H, m), 6.10-6.20(1H, m), 6.26-6.30(1H, m), 7.19-7.33 (15H, m)

FAB-MS(m/e, as $(C_{39}H_{50}N_4O_3+H)^+$): 623

EXAMPLE 13

N-(2-{3-({(3R)-1-(1-cyclohepten-1-ylmethyl)-3-piperidyl}-methyl)amino-3-oxopropyl}amino-2-oxoethyl)-3,3,3-triphenylpropanamide The title compound was prepared by a method similar to Step 7 of Example 1, using 1-cycloheptenecarbaldehyde (cf. WO 9633973). The product was obtained in the form of a colorless solid.

$^1$H-NMR(CDCl$_3$, δppm): 0.95-2.40(21H, m), 2.70-3.25 (4H, m), 3.40(2H, q, J=5.9 Hz), 3.56(2H, d, J=5.6 Hz), 3.64 (1H, d, J=15.7 Hz), 3.66(1H, d, J=15.7 Hz), 5.71-6.81(4H, m), 7.09-7.40(15H, m)

FAB-MS(m/e, as (C$_{40}$H$_{50}$N$_4$O$_3$+H)$^+$): 635

EXAMPLE 14

N-(2-{3-({(3R)-1-(1-cyclononen-1-ylmethyl)-3-piperidyl}-methyl)amino-3-oxopropyl}amino-2-oxoethyl)-3,3,3-triphenylpropanamide The title compound was prepared by a method similar to Step 7 of Example 1, using 1-cyclononenecarbaldehyde (cf. WO 9804554). The product was obtained in the form of a colorless solid.

$^1$H-NMR(CDCl$_3$, δppm): 0.78-2.41(25H, m), 2.51-3.47 (6H, m), 3.56(2H, d, J=5.4 Hz), 3.65(1H, d, J=15.9 Hz), 3.66(1H, d, J=15.9 Hz), 5.38-6.83(4H, m), 7.05-7.38(15H, m)

FAB-MS(m/e, as (C$_{42}$H$_{54}$N$_4$O$_3$+H)$^+$): 663

EXAMPLE 15

N-{2-(3-{((3S)-1-heptyl-3-piperidyl)methyl}amino-3-oxopropyl)amino-2-oxoethyl}-3,3,3-triphenylpropanamide The title compound was prepared by successively conducting procedures similar to Steps 5 and 6 of Example 1 and Example 8, using (3S)-3-amimomethyl-1-(tert-butoxycarbonyl)piperidine. The product was obtained as a colorless solid.

$^1$H-NMR(CDCl$_3$, δppm): 0.88(3H, t, J=6.8 Hz), 0.80-2.02 (17H, m), 2.20-2.41(4H, m), 2.70-2.90(2H, m), 2.90-3.20 (2H, m), 3.35-3.45(2H, m), 3.47(1H, dd, J=5.5, 16.6 Hz), 3.57(1H, dd, J=5.5, 16.6 Hz), 3.62(1H, d, J=15.0 Hz), 3.65 (1H, d, J=15.0 Hz), 6.09(1H, t, J=5.3 Hz), 6.18-6.35(1H, m), 6.48(1H, t, J=5.6 Hz), 7.10-7.39(15H, m)

FAB-MS(m/e, as (C$_{39}$H$_{52}$N$_4$O$_3$+H)$^+$): 625

EXAMPLE 16

N-{2-(3-{((3S)-1-cyclohexylmethyl-3-piperidyl)methyl}amino-3-oxopropyl)amino-2-oxoethyl}-3,3,3-triphenylpropanamide The title compound was prepared by successively conducting procedures similar to Steps 5 and 6 of Example 1 and Example 12, using (3S)-3-aminomethyl-1-(tert-butoxycarbonyl)piperidine. The product was obtained as a pale yellow solid.

$^1$H-NMR(CDCl$_3$, δppm): 0.81-1.80(17H, m), 1.97-2.08 (3H, m), 2.28-2.32(2H, m), 2.59-2.65(2H, m), 3.12-3.17(2H, m), 3.37-3.46(2H, m), 3.51-3.55(2H, m), 3.64(2H, s), 5.60-5.64 (1H, m), 6.10(1H, brs), 6.26-6.30(1H, m), 7.19-7.33 (15H,m)

FAB-MS(m/e,as (C$_{39}$H$_{50}$N$_4$O$_3$+H)$^+$): 623

EXAMPLE 17

N-{(1S)-2-(3-{((3R)-1-cyclohexylmethyl-3-piperidyl)methyl}-amino-3-oxopropyl)amino-1-(2-carbamoylethyl)-2-oxoethyl}-3,3,3-triphenylpropanamide (Step 1)

Synthesis of 3-(benzyloxycarbonyl)amino-N-({(3R)-1-(tert-butoxycarbonyl)-3-piperidyl}mehyl)propanamide The title compound was prepared by a method similar to Step 5 of Example 1, using N-benzyloxycarbonyl-β-alanine.

(Step 2)

Synthesis of 3-(benzyloxycarbonyl)amino-N-{((3S)-3-piperidyl)methyl}propanamide

To a solution of 1.84 g of 3-(benzyloxycarbonyl)amino-N-({(3R)-1-(tert-butoxycarbonyl)-3-piperidyl}methyl)propanamide in 2 ml of chloroform, 2 ml of trifluoroacetic acid was added at room temperature, followed by an hour's stirring at the same temperature. The reaction liquid was distilled off under reduced pressure, and the residue was rendered basic with 4N aqueous sodium hydroxide solution. Extracting the product with chloroform, the product was dried over anhydrous sodium sulfate. Upon distilling the solvent off under reduced pressure, 1.26 g of the title compound was obtained.

(Step 3)

Synthesis of 3-(benzyloxycarbonyl)amino-N-{((3R)-1-cyclohexylmethyl-3-piperidyl)methyl}propanamide To a solution of 600 mg of 3-(benzyloxycarbonyl)amino-N-{((3S)-3-piperidyl)methyl}propanamide in 3 ml of methanol, a solution of 150 mg of sodium cyanoborohydrate and 160 mg of zinc chloride in 8.1 ml of methanol, and 0.30 ml of cyclohexanecarbaldehyde were added at room temperature, followed by an hour's stirring at the same temperature. The reaction liquid was diluted with ethyl acetate and successively washed with saturated aqueous sodium bicarbonate solution and saturated saline, followed by drying over anhydrous sodium sulfate. Upon distilling the solvent off under reduced pressure, 775 mg of the title compound was obtained.

(Step 4)

Synthesis of 3-amino-N-{((3R)-1-cyclohexylmethyl-3-piperidyl)methyl}propanamide

To a solution of 770 mg of 3-(benzyloxycarbonyl)amino-N-{((3R)-1-cyclohexylmethyl-3-piperidyl) methyl}propanamide in 12 ml of methanol, 0.5 ml of 10% hydrochloric acid-methanol and 15 mg of 20% palladium hydroxide-carbon catalyst were added, followed by 44 hours' stirring under 3 atmospheres of hydrogen. Filtering the catalyst off, the solvent was distilled off under reduced pressure, and the residue was rendered weakly basic with saturated aqueous sodium bicarbonate solution. The product was extracted with chloroform and dried over anhydrous sodium sulfate. The solvent was distilled off under reduced pressure, and the resulting residue was purified by means of silica gel column chromatography (eluting solvent: chloroform-chloroform/methanol/28% aqueous ammonia=100/10/1) to provide 391 mg of the title compound.

(Step 5)

Synthesis of (2S)-2-amino-N$^5$-triphenylmethyl-N$^1$-(3-{((3R)-1-cyclohexylmethyl-3-piperidyl)methyl}amino-3-oxopropyl)-pentanediamide monohydrochloride The title compound was prepared by procedures similar to Steps 5-6 of Example 1, using 3-amino-N-{((3R)-1-cyclohexyl-methyl-3-piperidyl)methyl}propanamide and N-α-(tert-butoxycarbonyl)-γ-triphenylmethyl-L-glutamine.

(Step 6)

Synthesis of N-{(1S)-2-(3-{((3R)-1-cyclohexylmethyl-3-piperidyl)methyl}amino-3-oxopropyl)amino-1-(2-carbamoylethyl)-2-oxoethyl}-3,3,3-triphenylpropanamide To a solution of 84 mg of (2S)-2-amino-$N^5$-triphenylmethyl-$N^1$-(3-{((3R)-1-cyclohexylmethyl-3-piperidyl)methyl}amino-3-oxopropyl)pentanediamide monohydrochloride in 1.5 ml of chloroform, 0.052 ml of N,N-diisopropylethylamine was added at room temperature, followed by an hour's stirring at the same temperature. Then 39 mg of 3,3,3-triphenylpropionic acid, 24 mg of 1-hydroxybenzotriazole monohydrate and 31 mg of 1-ethyl-3-(3-dimethylaminopropyl)carbodiimide monohydrochloride were added at room temperature by the order stated, followed by 17 hours' stirring at the same temperature. The reaction liquid was rendered weakly basic with saturated aqueous sodium bicarbonate solution, extracted with chloroform and dried over anhydrous sodium sulfate. Distilling the solvent off, the resultant residue was dissolved in 1 ml of chloroform, and to the solution 1 ml of trifluoroacetic acid was added at room temperature, followed by 20 minutes' stirring at the same temperature. The reaction liquid was rendered weakly basic with saturated aqueous sodium bicarbonate solution, extracted with chloroform and dried over anhydrous sodium sulfate. The solvent was distilled off under reduced pressure, and the resultant residue was purified with preparative thin layer chromatography (Kieselgel™60F$_{254}$, Art 5744 (Merck), chloroform/methanol/28% aqueous ammonia=90/10/1) to provide 43 mg of the title compound as a white solid.

$^1$H-NMR(CD$_3$OD, δppm): 0.80-2.00(22H, m), 2.06-2.18 (2H, m), 2.23-2.33(2H, m), 2.73-2.87(2H, m), 2.90-3.08 (2H, m), 3.20-3.38(2H, m), 3.58(1H, d, J=15.0 Hz), 3.86 (1H, d, J=15.0 Hz), 3.84-3.91(1H, m), 7.10-7.28(15H, m)

FAB-MS(m/e, as (C$_{42}$H$_{55}$N$_5$O$_4$+H)$^+$): 694

EXAMPLE 18

N-{(1R)-2-(3-{(1-cyclohexylmethyl-3-piperidyl)methyl}amino-3-oxopropyl)amino-1-(2-carbamoylethyl)-2-oxoethyl})-3,3,3-triphenylpropanamide (Step 1)

Synthesis of 3-amino-N-{(1-cyclohexylmethyl-3-piperidyl)methyl}propanamide

The title compound was prepared by procedures similar to Steps 1-4 of Example 17, using 3-aminomethyl-1-(tert-butoxycarbonyl)piperidine.

(Step 2)

Synthesis of N-{(1R)-2-(3-{(1-cyclohexylmethyl-3-piperidyl)methyl}amino-3-oxopropyl)amino-1-(2-carbamoylethyl)-2-oxoethyl}-3,3,3-triphenylpropanamide The title compound was prepared by procedures similar to Steps 5-6 of Example 17 using 3-amino-N-{(1-cyclohexylmethyl-3-piperidyl)methyl}propanamide and N-α-(tert-butoxycarbonyl)-γ-triphenylmethyl-D-glutamine. The compound was obtained as a white solid.

$^1$H-NMR(CD$_3$OD, δppm): 0.80-0.98(3H, m), 1.15-1.32 (3H, m), 1.47-2.00(16H, m), 2.13(2H, d, J=6.9 Hz), 2.31 (2H, t, J=6.4 Hz), 2.86-2.87(2H, m), 2.98-3.04(2H, m), 3.30-3.37 (2H, m), 3.58(1H, d, J=15.0 Hz), 3.86 (1H, d, J=15.0 Hz), 3.87-3.91(1H, m), 7.13-7.30(15H, m)

FAB-MS(m/e, as (C$_{42}$H$_{55}$N$_5$O$_4$+H)$^+$): 694

EXAMPLE 19

N-{(1S)-2-(3-{((3R)-1-cyclohexylmethyl-3-piperidyl)methyl}-amino-3-oxopropyl)amino-1-(1H-imidazol-4-ylmethyl)-2-oxoethyl}-3,3,3-triphenylpropanamide The title compound was prepared by successively conducting procedures similar to Step 5 of Example 17 and Step 3 of Example 1, using (tert-butoxycarbonyl)-N-imidazole-benzyloxycarbonyl-L-histidine. The compound was obtained as a white foamy substance.

$^1$H-NMR(CDCl$_3$, δppm): 0.73-2.00(20H, m), 2.02-2.28 (4H, m), 2.55-2.64(1H, m), 2.67-2.98(3H, m), 3.15-3.33 (2H, m), 3.60-3.77(2H, m), 4.25-4.34(1H, m), 6.18-6.40 (2H, m), 6.69(1H, s), 7.15-7.50(16H, m), 7.44(1H, s)

FAB-MS(m/e, as (C$_{43}$H$_{54}$N$_6$O$_3$+H)$^+$): 703

EXAMPLE 20

N-{(1R)-2-(3-{(1-cyclohexylmethyl-3-piperidyl)methyl}amino-3-oxopropyl)amino-1-(1H-imidazol-4-ylmethyl)-2-oxoethyl}-3,3,3-triphenylpropanamide The title compound was prepared by a method similar to Example 19, using 3-amino-N-{(1-cyclohexylmethyl-3-piperidyl)methyl}propanamide and N-α, imidazole-di-(tert-butoxycarbonyl)-D-histidine. The compound was obtained as a white solid.

$^1$H-NMR(CDCl$_3$, δppm): 0.75-1.80(19H, m), 1.80-1.98 (1H, m), 2.03-2.22(4H, m), 2.56-2.64(1H, m), 2.66-2.92(3H, m), 3.13-3.32(2H, m), 3.62-3.75(2H, m), 4.25-4.34(1H, m), 6.36-6.52(1H, m), 6.57(1H, s), 6.55-6.70(1H, m), 7.14-7.32 (16H, m), 7.41(1H, s)

FAB-MS(m/e, as (C$_{43}$H$_{54}$N$_6$O$_3$+H)$^+$): 703

EXAMPLE 21

N-{(1S)-2-(3-{(1-cyclohexylmethyl-3-piperidyl)methyl}amino-3-oxopropyl)amino-1-(2-hydroxyethyl)-2-oxoethyl}-3,3,3-triphenylpropanamide The title compound was prepared by a method similar to Example 19, using 3-amino-N-{(1-cyclohexylmethyl-3-piperidyl)methyl}propanamide and N-(tert-butoxycarbonyl)-L-homoserine. The compound was obtained as a white solid.

$^1$H-NMR(CDCl$_3$, δppm): 0.75-0.90(2H, m), 0.92-1.07 (1H,m), 1.10-1.98(17H, m), 2.03-2.10(2H, m), 2.25-2.34 (2H, m), 2.60-2.70(2H, m), 3.02-3.21(3H, m), 3.33-3.44(3H, m), 3.51-3.58(1H, m), 3.67-3.79(2H, m), 4.18-4.27(1H, m), 6.16-6.22(1H, m), 6.22-6.34(1H, m), 6.67-6.75(1H, m), 7.15-7.32(15H, m)

FAB-MS(m/e, as (C$_{41}$H$_{54}$N$_4$O$_4$+H)$^+$): 667

EXAMPLE 22

N-{2-(3-{((3R)-1-heptyl-3-piperidyl)methyl}amino-3-oxopropyl)amino-2-oxoethyl}-N-methyl-3,3,3-triphenylpropanamide The title compound was prepared by successively conducting procedures similar to Steps 1-6 of Example 1 and Example 8, using N-(tert-butoxycarbonyl)-N-methyl-glycine. The compound was obtained as a colorless solid.

¹H-NMR(CDCl₃, δppm): 0.79-2.00(20H, m), 2.17-3.81 (17H, m), 5.80-6.75(2H, m), 7.10-7.35(15H, m)
FAB-MS(m/e, as (C₄₀H₅₄N₄O₃+H)⁺): 639

EXAMPLE 23

N-{2-(3-{(1-heptyl-3-piperidyl)methyl}amino-3-oxopropyl)amino-2-oxoethyl}-N-methyl-3,3,3-triphenylpropanamide The title compound was prepared by a method similar to Example 22, using 3-aminomethyl-1-(tert-butoxycarbonyl)piperidine. The compound was obtained as a colorless solid.
¹H-NMR(CDCl₃, δppm): 0.79-2.00(20H, m), 2.17-3.81 (17H, m), 5.80-6.75(2H, m),7.10-7.35(15H, m)
FAB-MS(m/e, as (C₄₀H₅₄N₄O₃+H)⁺): 639

EXAMPLE 24

N-{6-{((3S)-3-piperidyl)methyl}amino-6-oxo-hexyl}-3,3,3-triphenylpropanamide (Step 1)
Synthesis of methyl 6-{(tert-butoxycarbonyl)amino}-hexanoate
1.28 Grams of 6-{(tert-butoxycarbonyl)amino}hexanoic acid was dissolved in a liquid mixture of 9 ml of chloroform and 3 ml of methanol. To the solution 1.27 g of 1-ethyl-3-(3-dimethylaminopropyl)carbodiimide monohydrochloride and 7 mg of 4-dimethylaminopyridine were successively added at room temperature, followed by 2 hours' stirring at the same temperature. The reaction liquid was diluted with chloroform, washed successively with saturated aqueous sodium bicarbonate solution and saturated aqueous ammonium chloride solution, and dried over anhydrous sodium sulfate. Distilling the solvent off under reduced pressure, 1.03 g of the title compound was obtained.

(Step 2)
Synthesis of N-{6-{((3S)-3-piperidyl)methyl}amino-6-oxohexyl}-3,3,3-triphenylpropanamide
The title compound was prepared by successively conducting procedures similar to Steps 2-5 of Example 1 and Step 2 of Example 17, using methyl 6-{(tert-butoxycarbonyl)amino}hexanoate. The compound was obtained as a white foamy substance.
¹H-NMR(CDCl₃, δppm): 0.98-1.82(12H, m), 2.06 (2H, t, J=7.5 Hz), 2.31(1H, t, J=11.0 Hz), 2.52-2.62(1H, m), 2.87-3.06(4H, m), 3.10(2H, q, J=6.6 Hz), 3.55(2H, s), 4.87-4.96 (1H, m), 5.65-5.72(1H, m), 7.15-7.38(15H, m)
FAB-MS(m/e, as (C₃₃H₄₁N₃O₂+H)⁺): 512

EXAMPLE 25

N-{6-({(3R)-1-(2-methylbutyl)-3-piperidyl}methyl)amino-6-oxohexyl)-3,3,3-triphenylpropanamide The title compound was prepared by a method similar to Step 3 of Example 17, using N-{6-{((3S)-3-piperidyl)methyl}amino-6-oxohexyl}-3,3,3-triphenylpropanamide and 2-methylbutanal. The compound was obtained as a white foamy substance.
¹H-NMR(CDCl₃, δppm): 0.84-0.91(6H, m), 0.95-1.16 (6H, m), 1.36-2.19(14H, m), 2.59-2.72(2H, m), 2.87-2.95 (2H, m), 3.09-3.27(2H, m), 3.56(2H,s), 4.82-4.90(1H, m), 5.80-5.92(1H, m), 7.18-7.32(15H, m)
FAB-MS(m/e, as (C₃₈H₅₁N₃O₂+H)⁺): 582

EXAMPLE 26

N-{6-({(3R)-1-(2-methylpentyl)-3-piperidyl}methyl)amino-6-oxohexyl}-3,3,3-triphenylpropanamide The title compound was prepared by a method similar to Example 25, using 2-methylpentanal. The compound was obtained as a white solid.
¹H-NMR(CDCl₃, δppm): 0.85-0.95(6H, m), 0.97-1.16 (6H, m), 1.18-2.22(16H, m), 2.62-2.78(2H, m), 2.87-2.94 (2H, m), 3.08-3.25(2H, m), 3.56(2H, s), 4.80-4.88(1H, m), 5.80-5.92(1H, m), 7.18-7.37(15H, m)
FAB-MS(m/e, as (C₃₉H₅₃N₃O₂+H)⁺): 596

EXAMPLE 27

N-(6-{((3R)-1-ethyl-3-piperidyl)methyl}amino-6-oxohexyl)-3,3,3-triphenylpropanamide The title compound was prepared by a method similar to Example 25, using acetaldehyde. The compound was obtained as a white solid.
¹H-NMR(CDCl₃, δppm): 0.90-1.03(2H, m), 1.07 (6H, t, J=7.1 Hz), 1.43-1.80(7H, m), 1.85-2.96(1H, m), 2.07 (2H, t, J=7.6 Hz), 2.38(2H, q, J=7.2 Hz), 2.78-2.85(2H, m), 2.85-2.96(2H, m), 3.10-3.20(2H, m), 3.56(2H, s), 2.78-4.88 (1H, m), 5.77-5.67(1H, m), 7.17-7.38(15H, m)
FAB-MS(m/e, as (C₃₅H₄₅N₃O₂+H)⁺): 540

EXAMPLE 28

N-(6-{((3R)-1-cyclohexylmethyl-3-piperidyl)methyl}amino-6-oxohexyl)-3,3,3-triphenylpropanamide The title compound was prepared by a method similar to Example 25, using cyclohexanecarbaldehyde. The compound was obtained as a white foamy substance
¹H-NMR(CDCl₃, δppm): 0.80-1.80(23H, m), 1.95-2.08 (5H,m), 2.57-2.65(2H, m), 2.87-2.94(2H, m), 3.13-3.20(2H, m), 3.56(2H, s), 4.78-4.81(1H, m), 5.78-5.80(1H, m), 7.20-7.32(15H, m)
FAB-MS(m/e, as (C₄₀H₅₃N₃O₂+H)⁺): 608

EXAMPLE 29

N-{6-(3-piperidylmethyl)amino-6-oxohexyl}-3,3,3-triphenylpropanamide

The title compound was prepared by a method similar to Example 24, using 3-aminomethyl-1-(tert-butoxycarbonyl)piperidine. The compound was obtained as a white foamy substance.
¹H-NMR(CDCl₃, δppm): 0.98-1.82(12H, m), 2.06 (2H, t, J=7.5 Hz), 2.31(1H, t, J=11.0 Hz), 2.52-2.62(1H, m), 2.87-3.06(4H, m), 3.10(2H, q, J=6.6 Hz), 3.55(2H, s), 4.87-4.96 (1H, m), 5.65-5.72(1H, m),7.15-7.38(15H, m)
FAB-MS(m/e, as (C₃₃H₄₁N₃O₂+H)⁺): 512

EXAMPLE 30

N-(6-{(1-butyl-3-piperidyl)methyl}amino-6-oxohexyl)-3,3,3-triphenylpropanamide

The title compound was prepared by a method similar to Step 3 of Example 17, using N-{6-(3-piperidylmethyl)

amino-6-oxohexyl}-3,3,3-triphenylpropanamide and n-butylaldehyde. The compound was obtained as a white solid.

$^1$H-NMR(CDCl$_3$, δppm): 0.88-1.13(8H, m), 1.24-1.40 (2H, m), 1.43-1.78(7H, m), 1.83-1.98(2H, m), 2.04-2.16(3H, m), 2.38-2.48(2H, m), 2.85-2.97(4H, m), 3.08-3.23(2H, m), 3.56(2H, s), 4.83-4.92(1H, m), 5.78-5.88(1H, m), 7.15-7.32 (15H, m)

FAB-MS(m/e, as (C$_{37}$H$_{49}$N$_3$O$_2$+H)$^+$): 568

EXAMPLE 31

N-(6-{(1-isobutyl-3-piperidyl)methyl}amino-6-oxohexyl)-3,3,3-triphenylpropanamide The title compound was prepared by a method similar to Example 30, using isobutylaldehyde. The compound was obtained as a colorless oily substance.

$^1$H-NMR(CDCl$_3$, δppm): 0.80-2.33(24H, m), 2.60-3.05 (4H, m), 3.05-3.33(2H, m), 3.56(2H, s), 4.77-5.02(1H, m), 5.80-6.10(1H, m), 7.10-7.55(15H, m)

FAB-MS(m/e, as (C$_{37}$H$_{49}$N$_3$O$_2$+H)$^+$): 568

EXAMPLE 32

N-{6-({1-(2-ethylbutyl)-3-piperidyl}methyl)amino-6-oxohexyl}-3,3,3-triphenylpropanamide The title compound was prepared by a method similar to Example 30, using 2-ethylbutanal. The compound was obtained as a white solid.

$^1$H-NMR(CDCl$_3$, δppm): 0.85(6H, t, J=7.4 Hz), 0.93-1.19 (5H, m), 1.19-1.78(10H, m), 1.78-2.30(7H, m), 2.60-3.00 (4H, m), 3.03-3.31(2H, m), 3.56(2H, s), 4.77-4.96(1H, m), 5.82-6.03(1H, m), 7.10-7.38(15H, m)

FAB-MS(m/e, as (C$_{39}$H$_{53}$N$_3$O$_2$+H)$^+$): 596

EXAMPLE 33

N-(6-{(1-cyclohexyl-3-piperidyl)methyl}amino-6-oxohexyl)-3,3,3-triphenylpropanamide The title compound was prepared by a method similar to Example 30, using cyclohexanone. The compound was obtained as a white solid.

$^1$H-NMR(CDCl$_3$, δppm): 0.83-1.38(10H, m), 1.40-1.94 (11H, m), 2.00-2.17(3H, m), 2.20-2.48(2H, m), 2.50-3.03 (4H, m), 3.03-3.28(2H, m), 3.56(2H, s), 4.79-4.97(1H, m), 5.82-6.03(1H, m),7.15-7.40(15H,m)

FAB-MS(m/e, as (C$_{39}$H$_{51}$N$_3$O$_2$+H)$^+$): 594

EXAMPLE 34

N-(6-{(1-benzyl-3-piperidyl)methyl}amino-6-oxohexyl)-3,3,3-triphenylpropanamide

The title compound was prepared by a method similar to Example 30, using benzaldehyde. The compound was obtained as a colorless oily substance.

$^1$H-NMR(CDCl$_3$, δppm): 0.80-1.88(11H, m), 1.90-2.45 (4H, m), 2.75-3.28(6H, m), 3.55(2H, s), 3.65-3.92(2H, m), 4.78-5.00(1H, m), 6.05-6.30(1H, m), 7.06-7.60(20H, m)

FAB-MS(m/e, as (C$_{40}$H$_{47}$N$_3$O$_2$+H)$^+$): 602

EXAMPLE 35

N-(6-{(1-cyclooctylmethyl-3-piperidyl)methyl}amino-6-oxohexyl)-3,3,3-triphenylpropanamide The title compound was prepared by a method similar to Example 30, using cyclooctanecarbaldehyde. The compound was obtained as a white solid.

$^1$H-NMR(CDCl$_3$, δppm): 0.98-2.10(32H, m), 2.60-2.70 (2H, m), 2.87-2.93(2H, m), 3.08-3.28(2H,m), 3.56(2H,m), 4.79-4.87(1H, m), 5.82-5.92(1H, m), 7.18-7.30(15H, m)

FAB-MS(m/e, as (C$_{42}$H$_{57}$N$_3$O$_2$+H)$^+$): 636

EXAMPLE 36

N-{6-({1-(1-cyclononen-1-ylmethyl)-3-piperidyl}methyl)amino-6-oxohexyl}-3,3,3-triphenylproyanamide The title compound was prepared by a method similar to Example 30, using 1-cyclononenecarbaldehyde (WO9804554). The compound was obtained as a white solid.

$^1$H-NMR(CDCl$_3$, δppm): 0.95-1.80(22H, m), 1.90-1.98 (7H,m), 2.58-2.70(2H, m), 2.77(2H, s), 2.87-2.93(2H, m), 3.12-3.18(2H, m), 3.56(2H, s), 4.78-4.85(1H, m), 5.36-5.43 (1H,m), 5.65-5.75(1H, m), 7.18-7.30(15H, m)

FAB-MS(m/e, as (C$_{43}$H$_{57}$N$_3$O$_2$+H)$^+$): 648

EXAMPLE 37

N-(6-{(1-allyl-3-piperidyl)methyl}amino-6-oxohexyl)-3,3,3-triphenylpropanamide

The title compound was prepared by a method similar to Example 30, using acrylaldehyde. The compound was obtained as a pale yellow solid.

$^1$H-NMR(CDCl$_3$, δppm): 0.78-2.24(15H, m), 2.68-3.27 (8H,m), 3.56(2H, s), 4.70-4.93(1H, m), 5.05-5.28(2H, m), 5.50-5.72(1H,m), 5.75-5.98(1H, m), 7.10-7.50(15H, m)

FAB-MS(m/e, as (C$_{36}$H$_{45}$N$_3$O$_2$+H)$^+$): 552

EXAMPLE 38

N-{6-({(3S)-1-(2-methylbutyl)-3-piperidyl}methyl)amino-6-oxohexyl}-3,3,3-triphenylpropanamide The title compound was prepared by successively conducting methods which are similar to Examples 24 and 25, using (3S)-3-aminomethyl-1-(tert-butoxycarbonyl)piperidine. The compound was obtained as a white foamy substance.

$^1$H-NMR(CDCl$_3$, δppm): 0.83-0.92(6H, m), 0.97-1.16 (6H, m), 1.36-1.95(9H, m), 2.02-2.21(5H, m), 2.60-2.73(2H, m), 2.87-2.95 (2H, m), 3.08-3.27(2H, m), 3.56(2H, s), 4.79-4.88 (1H, m), 5.78-5.90(1H, m), 7.17-7.33(15H, m)

FAB-MS(m/e, as (C$_{38}$H$_{51}$N$_3$O$_2$+H)$^+$): 582

EXAMPLE 39

(2R)-N-((3S)-3-piperidylmethyl)-1-{(2S)-1-(3,3,3-triphenylpropanoyl)pyrrolidin-2-yl}carbonylpyrrolidine-2-carboxamide (Step 1)

Synthesis of methyl (2R)-pyrrolidine-2-carboxylate monohyrochloride

The title compound was prepared by successively conducting methods which are similar to Step 1 of Example 24 and Step 2 of Example 1, using N-(tert-butoxycarbonyl)-D-proline.

(Step 2)

Synthesis of (2R)-N-((3S)-3-piperidylmethyl)-1-{(2S)-1-(3,3,3-triphenylpropanoyl)pyrrolidin-2-yl}carbonylpyrrolidine-2-carboxamide The title compound was prepared by successively conducting methods which are similar to Steps 1-5 of Example 1 and Step 2 of Example 17, using methyl (2R)-pyrrolidine-2-carboxylate monohydrochloride and N-(tert-butoxycarbonyl)-L-proline. The compound was obtained as a colorless oily substance.

$^1$H-NMR(CDCl$_3$, δppm): 0.93-1.52(3H, m), 1.55-2.03 (10H,m), 2.11(1H, t, J=10.1 Hz), 2.25-2.33(1H, m), 2.48-2.57 (1H,m), 2.66-2.80(2H, m), 2.88-3.02(3H, m), 3.28-3.42 (2H, m), 3.43(1H, d, J=14.6 Hz), 3.78-3.86(1H, m), 3.91 (1H, d, J=14.6 Hz), 4.10 (1H, t, J=7.1 Hz), 4.57(1H, d, J=8.2 Hz), 7.15-7.30(16H,m)

FAB-MS(m/e, as (C$_{37}$H$_{44}$N$_4$O$_3$+H)$^+$): 593

EXAMPLE 40

(2R)-N-{((3R)-1-cyclohexylmethyl-3-piperidyl)methyl})-1-{(2S)-1-(3,3,3-triphenylpropanoyl)pyrrolidin-2-yl}carbonylpyrrolidine-2-carboxamide The title compound was prepared by a method similar to Step 3 of Example 17, using (2R)-N-((3S)-3-piperidylmethyl)-1-{(2S)-1-(3,3,3-triphenylpropanoyl)pyrrolidin-2-yl}carbonylpyrrolidine-2-carboxamide. The compound was obtained as a white foamy substance.

$^1$H-NMR(CDCl$_3$, δppm): 0.78-0.91(4H, m), 1.10-1.30 (5H,m), 1.32-1.97(16H, m), 2.00-2.09(2H, m), 2.25-2.33 (1H, m), 2.50-2.83(4H, m), 3.04-3.13(1H, m), 3.27-3.38(2H, m), 3.41(1H, d, J=14.6 Hz), 3.77-3.86(1H, m), 3.90 (1H, d, J=14.6 Hz), 4.06-4.12(1H, m), 4.55-4.62(1H, m), 7.13-7.32 (16H,m)

FAB-MS(m/e, as (C$_{44}$H$_{56}$N$_4$O$_3$+H)$^+$): 689

EXAMPLE 41

(2R)-N-(3-piperidylmethyl)-1-{(2S)-1-(3,3,3-triphenylpropanoyl)pyrrolidin-2-yl}carbonylpyrrolidine-2-carboxamide monohydrochloride (Step 1)

Synthesis of (2R)-1-{(2S)-1-(3,3,3-triphenylpropanoyl)pyrrolidin-2-yl}carbonylpyrrolidine-2-carboxylic acid The title compound was prepared by conducting procedures similar to Steps 1-4 of Example 1, using methyl (2R)-pyrrolidine-2-carboxylate monohydrochloride and N-(tert-butoxycarbonyl)-L-proline.

(Step 2)

Synthesis of (2R)-N-(3-piperidylmethyl)-1-{(2S)-1-(3,3,3-triphenylpropanoyl)pyrrolidin-2-yl}carbonylpyrrolidine-2-carboxamide monohydrochloride The title compound was prepared by conducting procedures similar to Steps 5-6 of Example 1, using (2R)-1-{(2S)-1-(3,3,3-triphenylpropanoyl)pyrrolidin-2-yl}carbonylpyrrolidine-2-carboxylic acid and 3-aminomethyl-1-(tert-butoxycarbonyl)piperidine. The compound was obtained as a white solid.

$^1$H-NMR(CD$_3$OD, δppm): 1.10-2.16(15H, m), 2.34-2.53 (1H, m), 2.60-3.16(5H, m), 3.34-3.54(3H, m), 3.70-3.90(2H, m), 4.12-4.19(1H, m), 4.35-4.40(1H, m), 7.10-7.30(15H, m)

FAB-MS(m/e, as (C$_{37}$H$_{44}$N$_4$O$_3$+H)$^+$): 593

EXAMPLE 42

(2R)-N-{(1-methyl-3-piperidyl)methyl})-1-{(2S)-1-(3,3,3-triphenylpropanoyl)pyrrolidin-2-yl}carbonylpyrrolidine-2-carboxamide The title compound was prepared by a method similar to Step 7 of Example 1 using (2R)-N-(3-piperidylmethyl)-1-{(2S)-1-(3,3,3-triphenylpropanoyl)pyrrolidin-2-yl}carbonylpyrrolidine-2-carboxamide monohydrochloride and 37% queous formaldehyde solution. The compound was obtained as s white solid.

$^1$H-NMR(CDCl$_3$, δppm): 0.85-2.05(13H, m), 2.23-2.35 (4H, m), 2.46-2.58(1H, m), 2.65-3.90(3H, m), 2.99-3.17 (1H, m), 3.28-3.47 (3H, m), 3.78-3.90(2H, m), 3.99-4.15 (2H, m), 4.53-4.62(1H, m), 7.13-7.38(16H, m)

FAB-MS(m/e, as (C$_{38}$H$_{46}$N$_4$O$_3$+H)$^+$): 607

EXAMPLE 43

(2R)-N-{(1-benzyl-3-piperidyl)methyl}-1-{(2S)-1-(3,3,3-triphenylpropanoyl)pyrrolidin-2-yl}carbonylpyrrolidine-2-carboxamide The title compound was prepared by a method similar to Example 42, using benzaldehyde. The compound was obtained as a white solid.

$^1$H-NMR(CDCl$_3$, δppm): 0.75-2.00(14H, m), 2.11-2.28 (1H,m), 2.37-2.58(1H, m), 2.60-2.70(1H, m), 2.74-2.90 (2H, m), 3.02-3.29(2H, m), 3.32-3.56(4H, m), 3.56-3.67 (1H, m), 3.82-3.97(1H, m), 4.00-4.13(1H, m), 4.52-4.60 (1H, m), 7.10-7.40(21H, m)

FAB-MS(m/e, as (C$_{44}$H$_{50}$N$_4$O$_3$+H)$^+$): 683

EXAMPLE 44

(2R)-N-{(1-cyclohexylmethyl-3-piperidyl)methyl}-1-{(2S)-1-(3,3,3-triphenylproyanoyl)pyrrolidin-2-yl}carbonylpyrrolidine-2-carboxamide The title compound was prepared by a method similar to Example 42, using cyclohexanecarbaldehyde. The compound was obtained as a white solid.

$^1$H-NMR(CDCl$_3$, δppm): 0.75-0.92(4H, m), 1.11-1.22 (4H, m), 1.23-2.10(19H, m), 2.24-2.33(1H, m), 2.50-2.86 (4H, m), 2.98-3.14(1H, m), 3.26-3.38(2H, m), 3.41 (1H, d, J=14.5 Hz), 3.77-3.85(1H,m), 3.87(1H, d, J=14.5 Hz), 4.06-4.16(1H, m), 4.57-4.61(1H, m), 7.14-7.35(16H, m)

FAB-MS(m/e, as (C$_{44}$H$_{56}$N$_4$O$_3$+H)$^+$): 689

EXAMPLE 45

(2R)-1-{(2S,4R)-4-tert-butoxy-1-(3,3,3-triphenylpropanoyl)pyrrolidin-2-yl}carbonyl-N-((3S)-3-piperidylmethyl)pyrrolidine-2-carboxamide (Step 1)

Synthesis of (2R)-1-benzyloxycarbonyl-N-({(3R)-1-(tert-butoxycarbonyl)-3-piperidyl}methyl)pyrrolidine-2-carboxamide The title compound was prepared by a method similar to Step 5 of Example 1, using N-benzyloxycarbonyl-D-proline.

(Step 2)

Synthesis of (2R)-N-({(3R)-1-(tert-butoxycarbonyl)-3-piperidyl}methyl)-pyrrolidine-2-carboxamide To a solution of 2.49 g of (2R)-1-benzyloxycarbonyl-N-({(3R)-1-(tert-butoxycarbonyl)-3-piperidyl}methyl)pyrrolidine-2-carboxamide in 20 ml of methanol, 15 mg of 20% palladium hydroxide-carbon catalyst was added, followed by 5 hours' stirring in hydrogen atmosphere. After filtering the catalyst off, the solvent was distilled off under reduced pressure to provide 1.78 g of the title compound.

(Step 3)

Synthesis of (2R)-N-({(3R)-1-(tert-butoxycarbonyl)-3-piperidyl}methyl-1-{(2S,4R)-4-(tert-butoxy)pyrrolidin-2-yl}carbonylpyrrolidine-2-carboxamide The title compound was prepared by methods similar to Steps 1 and 2 of Example 45, using (2R)-N-({(3R)-1-(tert-butoxycarbonyl)-3-piperidyl}methyl)pyrrolidine-2-carboxamide and N-benzyloxycarbonyl-O-(tert-butyl)-trans-4-hydroxy-L-proline.

(Step 4)

Synthesis of (2R)-N-({(3R)-1-(tert-butoxycarbonyl)-3piperidyl}methyl)-1-{(2S,4R)-4-(tert-butoxy)-1-(3,3,3-triphenylpropanoyl)pyrrolidin-2-yl}-carbonylpyrrolidine-2-carboxamide To a solution of 2.12 g of (2R)-N-({(3R)-1-(tert-butoxycarbonyl)-3-piperidyl}methyl)-1-{(2S,4R)-4-(tert-butoxy)pyrrolidin-2-yl}carbonylpyrrolidine-2-carboxamide and 1.67 g of 3,3,3-triphenylpropionic acid in 25 ml of chloroform, 944 mg of 1-hydroxybenzotriazole monohydrate and 1.18 g of 1-ethyl-3-(3-dimethylaminopropyl)carbodiimide monohydrochloride were successively added at room temperature, followed by 40 hours' stirring at the same temperature. The reaction liquid was diluted with chloroform, washed with saturated aqueous sodium bicarbonate solution and dried over anhydrous sodium sulfate. Distilling the solvent off under reduced pressure, the residue was purified by means of silica gel column chromatography (eluting solvent: from hexane/ethyl acetate=2/1 to ethyl acetate) to provide 2.98 g of the title compound.

(Step 5)

Synthesis of (2R)-1-{(2S,4R)-4-tert-butoxy-1-(3,3,3-triphenylpropanoyl)pyrrolidin-2-yl}carbonyl-N-((3S)-3-piperidylmethyl)pyrrolidine-2-carboxamide The title compound was prepared by a method similar to Step 2 of Example 17, using (2R)-N-({(3R)-1-(tert-butoxycarbonyl)-3-piperidyl}methyl)-1-{(2S,4R)-4-(tert-butoxy)-1-(3,3,3-triphenylpropanoyl)pyrrolidin-2-yl}carbonylpyrrolidine-2-carboxamide. The compound was obtained as a white foamy substance.

$^1$H-NMR(CDCl$_3$, δppm): 0.88-1.05(1H, m), 1.12(9H, s), 1.29-2.00(10H, m), 2.04(1H, t, J=11.3 Hz), 2.25-2.38(2H, m), 2.42-2.53(1H, m), 2.78-2.88(2H, m), 2.92-3.05(2H, m), 3.30-3.40(1H,m), 3.50(1H, d, J=14.7 Hz), 3.52-3.58(1H, m), 3.76-3.83(1H, m), 3.81(1H, d, J=14.7 Hz), 4.27-4.37(2H, m), 4.57(1H, d, J=6.9 Hz), 7.13-7.33(16H, m)

FAB-MS(m/e, as $(C_{41}H_{52}N_4O_4+H)^+$): 665

EXAMPLE 46

(2R)-1-{(2S,4R)-4-hydroxy-1-(3,3,3-triphenylproyanoyl)pyrrolidin-2-yl}carbonyl-N-((3S)-3-piperidylmethyl)pyrrolidine-2carboxamide To 1.65 g of (2R)-1-{(2S,4R)-4-tert-butoxy-1-(3,3,3-triphenylpropanoyl)pyrrolidin-2-yl}carbonyl-N-((3S)-3-piperidylmethyl)pyrrolidine-2-carboxamide, 5 ml of trifluoroacetic acid was added at room temperature, followed by 1 hour's stirring at the same temperature. The reaction liquid was distilled off under reduced pressure, diluted with chloroform, rendered basic with 4N aqueous sodium hydroxide solution, extracted with chloroform and dried over anhydrous sodium sulfate. Distilling the solvent off under reduced pressure, 1.56 g of the title compound was obtained as a white foamy substance.

$^1$H-NMR(CDCl$_3$, δppm): 0.93-1.08(1H, m), 1.32-1.50 (1H,m),1.50-2.05(10H, m), 2.09(1H, t, J=11.1 Hz), 2.23-2.32 (1H, m), 2.51(1H, dt, J=2.3, 9.6 Hz), 2.57-2.68 (1H, m), 2.74(1H, d, J=10.9 Hz), 2.85-3.02(3H,m), 3.30-3.33 (1H, m), 3.42(1H, d, J=14.6 Hz), 3.58(1H, dd, J=4.1, 11.0 Hz), 3.80-3.87(1H, m), 3.90(1H, d, J=14.6 Hz), 4.30-4.38(2H, m), 4.56 (1H, d, J=6.9 Hz), 7.17-7.32(16H, m)

FAB-MS(m/e, as $(C_{37}H_{44}N_4O_4+H)^+$): 609

EXAMPLE 47

(2R)-1-{(2S,4R)-4-hydroxy-1-(3,3,3-triphenylpropanoyl)pyrrolidin-2-yl}carbonyl-N-{((3R)-1-(2-methylbutyl)-3-piperidyl)methyl}-pyrrolidine-2-carboxamide The title compound was prepared by a method similar to Step 3 of Example 17, using (2R)-1-{(2S,4R)-4-hydroxy-1-(3,3,3-triphenylpropanoyl)pyrrolidin-2-yl}carbonyl-N-((3S)-3piperidylmethyl)pyrrolidine-2-carboxamide and 2-methylbutanal. The compound was obtained as a white solid.

$^1$H-NMR(CDCl$_3$, δppm): 0.80-2.15(24H, m), 2.23-2.35 (1H, m), 2.57-2.82(4H, m), 3.03-3.18(1H, m), 3.30-3.44(2H, m), 3.55-3.70(1H, m), 3.80-4.00(2H, m), 4.29-4.40(2H, m), 4.54-4.63(1H, m), 7.18-7.43(16H, m)

FAB-MS(m/e, as $(C_{42}H_{54}N_4O_4+H)^+$): 679

EXAMPLE 48

(2R)-1-{(2S,4R)-4-hydroxy-1-(3,3,3-triphenylpropanoyl)pyrrolidin-2-yl}carbonyl-N-{((3R)-1-methyl-3-piperidyl)methyl}-pyrrolidine-2-carboxamide The title compound was prepared by a method similar to Example 47, using 37% aqueous formaldehyde solution. The compound was obtained as a white solid.

$^1$H-NMR(CDCl$_3$, δppm): 0.72-0.95(3H, m), 1.23-1.32 (3H, m), 1.43(1H,t, J=11.0 Hz), 1.51-2.08(6H, m), 2.25(3H, s), 2.20-2.34(1H, m), 2.60-2.86(4H, m), 2.96-3.10(1H, m), 3.28-3.37(1H, m), 3.39(1H, d, J=14.3 Hz), 3.59 (1H, dd, J=3.7, 11.1 Hz), 3.80-3.91(1H, m), 3.98 (1H, d, J=14.3 Hz), 4.26-4.38(2H, m), 4.55(1H, d, J=7.0 Hz), 7.15-7.40(16H, m)

FAB-MS(m/e, as $(C_{38}H_{46}N_4O_4+H)^+$): 623

EXAMPLE 49

(2R)-N-{((3R)-1-ethyl-3-piperidyl)methyl}-1-{(2S,4R)-4-hydroxy-1-(3,3,3-triphenylproyanoyl)pyrrolidin-2-yl}carbonylpyrrolidine-2-carboxamide The title compound was prepared by a method similar to Example 47, using acetaldehyde. The compound was obtained as a white solid.

$^1$H-NMR(CDCl$_3$, δppm): 0.88(3H, t, J=6.7 Hz), 1.03 (2H, t, J=7.3 Hz), 1.23-1.30(1H, m), 1.38(1H, t, J=11.0 Hz), 1.52-

2.03(11H, m), 2.25-2.41(2H, m), 2.14-2.92(3H, m), 2.99-3.09(1H, m), 3.31-3.36(1H, m), 3.38(1H, d, J=14.3 Hz), 3.57-3.62(1H, m), 3.82-3.91(1H, m), 3.97(1H, d, J=14.3 Hz), 4.28-4.36(2H, m), 4.56(1H, d, J=6.6 Hz), 7.17-7.38(16H, m)
FAB-MS(m/e, as $(C_{39}H_{48}N_4O_4+H)^+$): 637

EXAMPLE 50

(2R)-N-{((3R)-1-butyl-3-piperidyl)methyl}-1-{(2S,4R)-4-hydroxy-1-(3,3,3-triphenylpropanoyl)pyrrolidin-2-yl}carbonylpyrrolidine-2-carboxamide The title compound was prepared by a method similar to Example 47, using n-butylaldehyde. The compound was obtained as a white solid.
$^1$H-NMR(CDCl$_3$, δppm): 0.91(6H, t, J=7.3 Hz), 1.25-2.05 (14H, m), 2.23-2.35(3H, m), 2.63-2.90(4H, m), 3.00-3.10 (1H, m), 3.31-3.36 (1H, m), 3.38(1H, d, J=14.3 Hz), 3.59 (1H, dd, J=4.2, 11.0 Hz), 3.81-3.90(1H, m), 3.95 (1H, d, J=14.3 Hz), 4.29-4.38(2H, m), 4.56 (1H, dd, J=1.3, 6.4 Hz), 7.17-7.35(16H, m)
FAB-MS(m/e, as $(C_{41}H_{52}N_4O_4+H)^+$): 665

EXAMPLE 51

(2R)-1-{(2S,4R)-4-hydroxy-1-(3,3,3-triphenylpropanoyl)pyrrolidin-2-yl}carbonyl-N-{((3R)-1-pentyl-3-piperidyl)methyl}-pyrrolidine-2-carboxamide The title compound was prepared by a method similar to Example 47, using valeraldehyde. The compound was obtained as a white solid.
$^1$H-NMR(CDCl$_3$, δppm): 0.83-2.05(22H, m), 2.22-2.33 (3H, m), 2.66-2.81(3H, m), 2.83-2.90(1H, m), 2.99-3.10 (1H, m), 3.30-3.36(1H, m), 3.39(1H, d, J=14.2 Hz), 3.60 (1H, dd, J=3.6, 10.9 Hz), 3.83-3.89(1H, m), 3.95 (1H, d, J=14.2 Hz), 4.28-4.36(2H, m), 4.56 (1H, d, J=6.3 Hz), 7.17-7.34(16H, m)
FAB-MS(m/e, as $(C_{42}H_{54}N_4O_4+H)^+$): 679

EXAMPLE 52

(2R)-N-{((3R)-1-hexyl-3-piperidyl)methyl}-1-{(2S,4R)-4-hydroxy-1-(3,3,3-triphenylpropanoyl)pyrrolidin-2-yl}carbonylpyrrolidine-2-carboxamide The title compound was prepared by a method similar to Example 47, using n-hexanal. The compound was obtained as a white solid.
$^1$H-NMR(CDCl$_3$, δppm): 0.78-0.93(6H, m), 1.15-2.10 (18H, m), 2.20-2.35(3H, m), 2.54-2.65(1H, m), 2.70-2.80 (2H, m), 2.80-2.91(1H, m), 3.02-3.12(1H, m), 3.30-3.40(1H, m), 3.40(1H, d, J=14.5 Hz), 3.59(1H, dd, J=3.8, 11.1 Hz), 3.85 (1H, dt, J=2.6, 10.4 Hz), 3.94(1H, d, J=14.5 Hz), 4.29-4.38 (2H, m), 4.53-4.60(1H, m), 7.17-7.38(16H, m)
FAB-MS(m/e, as $(C_{43}H_{56}N_4O_4+H)^+$): 693

EXAMPLE 53

(2R)-N-{((3R)-1-cycloheptylmethyl-3-piperidyl)methyl}-1-{(2S,4R)-4-hydroxyl-1-(3,3,3-triphenylpropanoyl)pyrrolidin-2-yl}carbonylpyrrolidine-2-carboxamide The title compound was prepared by a method similar to Example 47, using cycloheptanecarbaldehyde. The compound was obtained as a white foamy substance.

$^1$H-NMR(CDCl$_3$, δppm): 0.75-0.90(1H, m), 1.02-2.07 (27H, m), 2.25-2.33(1H, m), 2.49-2.68(2H, m), 2.70-2.80 (2H, m), 3.03-3.14(1H, m), 3.30-3.40(1H, m), 3.40 (1H, d, J=14.5 Hz), 3.60(1H, dd, J=3.9, 11.2 Hz), 3.80-3.87 (1H, m), 3.90(1H, d, J=14.5 Hz), 4.29-4.40(2H, m), 4.57 (1H, d, J=6.6 Hz), 7.14-7.37(16H, m)
FAB-MS(m/e, as $(C_{45}H_{58}N_4O_4+H)^+$): 719

EXAMPLE 54

(2R)-N-{((3R)-1-ethyl-3-piperidyl)methyl}-1-((2S,4R)-4-hydroxy-1-({3,3,3-tris(4-chlorophenyl)propanoyl}pyrrolidin-2-yl)-carbonylpyrrolidine-2-carboxamide (Step 1)
Synthesis of (2R)-1-((2S,4R)-4-hydroxy-1-{3,3,3-tris(4-chlorophenyl)propanoyl}pyrrolidin-2-yl)carbonyl-N-((3S)-3-piperidylmethyl)pyrrolidine-2-carboxamide
The title compound was prepared by successively conducting Step 4 of Example 45 and Example 46, using 3,3,3-tris(4-chlorophenyl)propionic acid.

(Step 2)
Synthesis of (2R)-N-{((3R)-1-ethyl-3-piperidyl)methyl}-1-((2S,4R)-4-hydroxy-1-{3,3,3-tris(4-chlorophenyl)propanoyl}pyrrolidin-2-yl)-carbonylpyrrolidine-2-carboxamide
The title compound was prepared by a method similar to Step 3 of Example 17, using (2R)-1-((2S,4R)-4-hydroxy-1-{3,3,3-tris-(4-chlorophenyl)propanoyl}pyrrolidin-2-yl)carbonyl-N-((3S)-3-piperidylmethyl)pyrrolidine-2-carboxamide and acetaldehyde. The compound was obtained as a white foamy substance.
$^1$H-NMR(CDCl$_3$, δppm): 0.80-1.78(12H, m), 1.90-2.08 (5H, m), 2.26-2.40(3H, m), 2.52-2.63(1H, m), 2.73-2.96 (3H, m), 3.00-3.11(1H, m), 3.34(1H, d, J=15.1 Hz), 3.35-3.42 (1H, m), 3.60-3.68 (1H, m), 3.84(1H, d, J=15.1 Hz), 3.83-3.90 (1H, m), 4.35-4.48 (2H, m), 4.56(1H, dd, J=1.4, 7.4 Hz), 7.12-7.30(12H,m)
FAB-MS(m/e, as $(C_{39}H_{45}Cl_3N_4O_4+H)^+$): 739

EXAMPLE 55

(2R)-N-{((3R)-1-cyclohexylmethyl-3-piperidyl)methyl}-1-{(2S,4R)-4-hydroxy-1-(3,3,3-triphenylpropanoyl)pyrrolidin-2-yl}carbonylpyrrolidine-2-carboxamide (Step 1)
Synthesis of (2R)-N-{((3R)-1-cyclohexylmethyl-3-piperidyl)-methyl}pyrrolidine-2-carboxamide
The title compound was prepared by a method similar to Steps 2-4 of Example 17, using (2R)-1-benzyloxycarbonyl-N-({(3R)-1-(tert-butoxycarbonyl)-3-piperidyl}methyl)pyrrolidine-2-carboxamide.

(Step 2)
Synthesis of (2R)-N-{((3R)-1-cyclohexylmethyl-3-piperidyl)methyl}-1-{(2S,4R)-4-hydroxy-1-(3,3,3-triphenylpropanoyl)pyrrolidin-2-yl}carbonylpyrrolidine-2-carboxamide
The title compound was prepared by successively conducting methods similar to Steps 1-2 of Example 17, Step 3 of Example 1 and Step 4 of Example 17, using (2R)-N-{((3R)-1-cyclohexylmethyl-3-piperidyl)methyl}pyrrolidine-2-carboxamide and N-(tert-butoxycarbonyl)-O-benzyl-trans-4-hydroxy-L-proline. The compound was obtained as a white solid.

$^1$H-NMR(CDCl$_3$, δppm): 0.80-2.02(24H, m), 2.05 (2H, d, J=7.0 Hz), 2.25-2.35(1H, m), 2.52-2.80(4H, m), 3.04-3.13 (1H, m), 3.30-3.38(1H,m), 3.39(1H, d, J=14.5 Hz), 3.60(1H, dd, J=3.8, 11.0 Hz), 3.81-3.89(1H, m), 3.91 (1H, d, J=14.5 Hz), 4.30-4.38(2H, m), 4.57 (1H, d, J=6.6 Hz), 7.17-7.33 (16H, m)

FAB-MS(m/e, as (C$_{44}$H$_{56}$N$_4$O$_4$+H)$^+$): 705

EXAMPLE 56

(2R)-N-{(1-cyclohexylmethyl-3-piperidyl)methyl}-1-{(2S,4R)-4-hydroxy-1-(3,3,3-triphenylpropanoyl)pyrrolidin-2-yl}carbonylpyrrolidine-2-carboxamide The title compound was prepared by successively conducting a method similar to Exampe 55, using 3-aminomethyl-1-(tert-butoxycarbonyl)piperidine. The compound was obtained as a white solid.

$^1$H-NMR(CDCl$_3$, δppm): 0.73-2.20(26H, m), 2.23-2.34 (1H, m), 2.53-2.90(4H, m), 2.97-3.13(1H, m), 3.29-3.43(2H, m), 3.53-3.70(1H, m), 3.80-3.95(2H, m), 4.27-4.40(2H, m), 4.52-4.60(1H, m), 7.15-7.40(16H, m)

FAB-MS(m/e, as (C$_{44}$H$_{56}$N$_4$O$_4$+H)$^+$): 705

EXAMPLE 57

(2R)-1-{(2S,4S)-4-amino-1-(3,3,3-triphenylpropanoyl)pyrrolidin-2 -yl}carbonyl-N-{((3R)-1-cyclohexylmethyl-3-piperidyl)methyl}pyrrolidine-2-carboxamide (Step 1)

Synthesis of (2R)-N-{((3R)-1-cyclohexylmehyl-3-piperidyl)methyl}-1-{(2S,4R)-4-(methylsulfonyloxy)-1-(3,3,3-triphenylpropanoyl)pyrrolidin-2-yl}carbonylpyrrolidine-2-carboxamide To a solution of 30 mg of (2R)-N-{((3R)-1-cyclohexylmehyl-3-piperidyl)methyl}-1-{(2S,4R)-4-hydroxy-1-(3,3,3-triphenylpropanoyl)pyrrolidin-2-yl}carbonylpyrrolidine-2-carboxamide in 0.6 ml of chloroform, 0.018 ml of triethylamine and 0.004 ml of methanesulfonyl chloride were added under cooling with ice, followed by 50 minutes' stirring at room temperature. The reaction liquid was diluted with chloroform, washed with saturated aqueous sodium bicarbonate solution and dried over anhydrous sodium sulfate. Distilling the solvent off under reduced pressure, the resultant residue was purified by means of a preparative thin-layer chromatography (Kieselgel™ 60F$_{254}$, Art 5744 (Merck), chloroform/methanol/28% aqueous ammonia=100/10/1) to provide 33 mg of the title compound.

(Step 2)

Synthesis of (2R)-1-{(2S,4S)-4-azido-1-(3,3,3-triphenyl-propanoyl)pyrrolidin-2-y1}carbonyl-N-{((3R)-1-cyclo-hexylmethyl-3-piperidyl)methyl}pyrrolidine-2-carboxamide To a solution of 33 mg of (2R)-N-{((3R)-1-cyclohexylme-hyl-3-piperidyl)methyl}-1-{(2S,4R)-4-(methylsulfony-loxy)-1-(3,3,3-triphenylpropanoyl)pyrrolidin-2-yl}carbonylpyrrolidine-2-carboxamide in 1 ml of N,N-dimethylformamide, 8.3 mg of sodium azide was added at room temperature, followed by 10 hours' stirring at 85° C. under heating. The reaction liquid was diluted with ethyl acetate, washed with water and dried over anhydrous sodium sulfate. Distilling the solvent off under reduced pressure, the resultant residue was purified by means of a preparative thin-layer chromatography (Kieselgel™ 60F$_{254}$, Art 5744 (Merck), chloroform/methanol/28% aqueous ammonia=100/10/1) to provide 25 mg of the title compound.

(Step 3)

Synthesis of (2R)-1-{(2S,4S)-4-amino-1-(3,3,3-triphenyl-propanoyl)pyrrolidin-2-yl}carbonyl-N-{((3R)-1-cyclohexy-lmethyl-3-piperidyl)methyl}pyrrolidine-2-carboxamide To a solution of 24 mg of (2R)-1-{(2S,4S)-4-azido-1-(3,3,3-triphenyl-propanoyl)pyrrolidin-2-yl}carbonyl-N-{((3R)-1-cyclohexylmethyl-3-piperidyl)methyl}pyrrolidine-2-carboxamide in 0.5 ml of 20% hydrous tetrahydrofuran, 13 mg of triphenylphosphine was added at room temperature, followed by 3 hours' refluxing under heating. The reaction liquid was diluted with chloroform, washed with saturated aqueous sodium bicarbonate solution and dried over anhydrous sodium sulfate. Distilling the solvent off under reduced pressure, the resultant residue was purified by means of a preparative thin-layer chromatography (Kieselgel™ 60F$_{254}$, Art 5744 (Merck), chloroform/methanol/28% aqueous ammonia=90/10/1) to provide 16 mg of the title compound in the form of a white solid.

$^1$H-NMR(CDCl$_3$, δppm): 0.75-0.95(4H, m), 1.10-1.32 (4H, m), 1.39(1H, t, J=10.8 Hz), 1.40-2.01(15H, m), 2.06 (2H, d, J=6.9 Hz), 2.07-2.18(1H, m), 2.26-2.33(1H, m), 2.54 (1H, quint, J=6.5 Hz), 2.60-2.70(1H, m), 2.70-2.80(1H, m), 2.89-2.99(1H, m), 3.05-3.17(3H, m), 3.29-3.37(1H, m), 3.39 (1H, d, J=14.3 Hz), 3.76-3.82(1H, m), 3.89 (1H, d, J=14.3 Hz), 4.13(1H, t, J=6.6 Hz), 4.59 (1H, dd, J=1.5, 8.0 Hz), 7.13-7.32(16H, m)

FAB-MS(m/e, as (C$_{44}$H$_{57}$N$_5$O$_3$+H)$^+$): 704

EXAMPLE 58

(2R)-N-{((3R)-1-cyclohexylmethyl-3-piperidyl)me-thyl}-1-{(2S,4S)-4-dimethylamino-1-(3,3,3-triph-enylpropanoyl)pyrrolidin-2-yl}-carbonylpyrrolidine-2-carboxamide The title compound was prepared by a method similar to Step 3 of Example 17, using (2R)-1-{(2S, 4S)-4-amino-1-(3,3,3-triphenylpropanoyl)pyrrolidin-2-yl}carbonyl-N-{((3R)-1-cyclohexylmethyl-3-piperidyl)methyl}pyrrolidine-2-carboxamide and 37% aqueous formaldehyde solution. The compound was obtained as a white solid.

$^1$H-NMR(CDCl$_3$, δppm): 0.78-0.92(4H, m), 1.10-1.27 (4H,m), 1.34-2.00(16H, m), 2.04(2H, d, J=7.2 Hz), 2.08(6H, s), 2.27-2.35(1H, m), 2.60-2.84(4H, m), 3.05-3.17(2H, m), 3.27-3.32(1H, m), 3.33(1H, d, J=14.0 Hz), 3.78-3.86(1H, m), 3.90(1H, d, J=14.0 Hz), 4.05-4.13(1H, m), 4.59 (1H, d, J=6.6 Hz), 7.16-7.34(16H, m)

FAB-MS(m/e, as (C$_{46}$H$_{61}$N$_5$O$_3$+H)$^+$): 732

EXAMPLE 59

(2R)-N-{((3R)-1-cyclohexylmethyl-3-piperidyl)me-thyl}-1-{(2S,4S)-4-hydroxy-1-(3,3,3-triphenylpro-panoyl)pyrrolidin-2-yl}-carbonylpyrrolidine-2-car-boxamide The title compound was prepared by a method similar to Steps 3-4 of Example 45, using (2R)-N-{((3R)-1-cyclohexy-lmethyl-3-piperidyl)methyl}pyrrolidine-2-carboxamide and N-benzyloxycarbonyl-cis-4-hydroxy-L-proline. The compound was obtained as a white foamy substance.

$^1$H-NMR(CDCl$_3$, δppm): 0.78-0.93(5H, m), 1.10-1.33 (5H, m), 1.43(1H, t, J=10.6 Hz), 1.40-2.01(12H, m), 2.06

(2H, d, J=7.2 Hz), 2.27-2.35(1H, m), 2.53-2.70(3H, m), 2.71-2.81 (1H, m), 3.07-3.18(1H,m), 3.40(1H, d, J=14.1 Hz), 3.40-3.49(2H, m), 3.88-3.95(1H, m), 3.94(1H, d, J=14.1 Hz), 4.07-4.16(1H, m), 4.19(1H, d, J=7.5 Hz), 4.59(1H, d, J=6.2 Hz), 5.62(1H, d, J=11.9 Hz), 7.10(1H, t, J=5.9 Hz), 7.14-7.38 (15H, m)

FAB-MS(m/e, as $(C_{44}H_{56}N_4O_4+H)^+$): 705

EXAMPLE 60

(2R)-1-{(2S,4R)-4-amino-1-(3,3,3-triphenylpropanoyl)pyrrolidin-2-yl}carbonyl-N-{((3R)-1-cyclohexylmethyl-3-piperidyl)methyl}pyrrolidine-2-carboxamide The title compound was prepared by a method similar to Example 57 using (2R)-N-{((3R)-1-cyclohexylmethyl-3-piperidyl)methyl}-1-{(2S,4S)-4-hydroxy-1-(3,3,3-triphenylpropanoyl)pyrrolidin-2-yl}carbonylpyrrolidine-2-carboxamide. The compound was obtained as a white solid.

$^1$H-NMR(CDCl$_3$, δppm): 0.73-2.10(27H, m), 2.25-2.34 (1H, m), 2.47-2.69(3H, m), 2.69-2.80(1H, m), 3.10 (1H, quint, J=6.7 Hz), 3.29-3.37(1H, m), 3.42 (1H, d, J=14.6 Hz), 3.59-3.70(2H, m), 3.79-3.85(1H, m), 3.90(1H, d, J=14.6 Hz), 4.30(1H, t, J=7.3 Hz), 4.58 (1H, dd, J=1.6, 7.8 Hz), 7.13-7.37 (16H, m)

FAB-MS(m/e, as $(C_{44}H_{57}N_5O_3+H)^+$): 704

EXAMPLE 61

(2R)-N-{((3R)-1-cyclohexylmethyl-3-piperidyl)methyl}-1-{(2S,4R)-4-dimethylamino-1-(3,3,3-triphenylpropanoyl)pyrrolidin-2-yl}-carbonylpyrrolidine-2-carboxamide The title compound was prepared by a method similar to Example 58, using (2R)-1-{(2S,4R)-4-amino-1-(3,3,3-triphenylpropanoyl)pyrrolidin-2-yl}carbonyl-N-{((3R)-1-cyclohexylmethyl-3-piperidyl)methyl}pyrrolidine-2-carboxamide. The compound was obtained as a white solid.

$^1$H-NMR(CDCl$_3$, δppm): 0.75-0.92(4H, m), 1.10-1.30 (4H, m), 1.30-1.75(13H, m), 1.75-1.97(2H, m), 2.04 (2H, d, J=7.2 Hz), 2.12(6H, s), 2.24-2.36(1H, m), 2.37-2.50 (1H, m), 2.57-2.69(2H, m), 2.70-2.80(1H, m), 3.02-3.15(2H, m), 3.28-3.38(1H, m), 3.44(1H, d, J=14.7 Hz), 3.50-3.60(1H, m), 3.71-3.80(1H, m), 3.88(1H, d, J=14.7 Hz), 4.24(1H, d, J=8.6 Hz), 4.58(1H, d, J=6.5 Hz), 7.05 (1H, t, J=5.3 Hz), 7.15-7.32(15H, m)

FAB-MS(m/e, as $(C_{46}H_{61}N_5O_3+H)^+$): 732

EXAMPLE 62

N-(7-{((3R)-1-cyclohexylmethyl-3-piperidyl)methyl}amino-7-oxoheptyl)-3,3,3-triphenylpropanamide The title compound was prepared by successively conducting methods similar to Examples 24 and 28, using 7-{(tert-butoxycarbonyl)amino}heptanoic acid. The compound was obtained as a white foamy substance.

$^1$H-NMR(CDCl$_3$, δppm): 0.78-1.82(26H, m), 2.10 (2H, d, J=7.5 Hz), 2.17(2H, d, J=6.9 Hz), 2.68-2.80(2H, m), 2.83-2.95(2H, m), 3.08-3.29(2H, m), 3.56(2H, s), 4.74-4.83 (1H, m), 5.85-6.00(1H, m), 7.10-7.40(15H, m)

FAB-MS(m/e, as $(C_{41}H_{55}N_3O_2+H)^+$): 622

EXAMPLE 63

(2R)-N-(1-cyclohexylmethyl-4-piperidyl)-1-{(2S)-1-(3,3,3-triphenylpropanoyl)pyrrolidin-2-yl}carbonylpyrrolidine-2-carboxamide The title compound was prepared by a method similar to Step 5 of Example 1, using 1-cyclohexylmethyl-4-piperidinamine (JP 52122378) and (2R)-1-{(2S)-1-(3,3,3-triphenylpropanoyl)pyrrolidin-2-yl}carbonylpyrrolidine-2-carboxylic acid. The compound was obtained as a white solid.

$^1$H-NMR(CDCl$_3$, δppm): 0.70-0.92(3H, m), 1.00-1.20 (3H, m), 1.22-1.39(3H, m), 1.40-1.93(14H, m), 1.95-2.05 (1H, m), 2.07-2.92(2H, m), 2.20-2.29(1H, m), 2.33-2.42(1H, m), 2.80-2.92(2H,m), 3.28-3.35(2H, m), 3.36(1H, d, J=13.7 Hz), 3.62-3.78(1H, m), 3.85-3.89(1H, m), 3.90(1H, d, J=13.7 Hz), 4.09(1H, t, J=6.7 Hz), 4.53(1H, d, J=7.9 Hz), 6.86 (1H, d, J=8.4 Hz), 7.13-7.38(15H, m)

FAB-MS(m/e, as $(C_{43}H_{54}N_4O_3+H)^+$): 675

EXAMPLE 64

(2R)-N-(4-piperidylmethyl)-1-{(2S)-1-(3,3,3-triphenylpropanoyl)pyrrolidin-2-yl}carbonylpyrrolidine-2-carboxamide The title compound was obtained by successively conducting methods similar to Example 63 and Step 2 of Example 17, using 4-aminomethyl-1-(tert-butoxycarbonyl)piperidine which was synthesized by the method of J. D. Prugh, et al. [*Synth. Commun.*, Vol. 22, 2357-2360 (1992)]. The compound was obtained as a pale yellow oily substance.

$^1$H-NMR(CDCl$_3$, δppm): 0.90-2.05(13H, m), 2.27-2.38 (1H, m), 2.48-2.60(2H, m), 2.62-2.84(2H, m), 2.98-3.10(3H, m), 3.28-3.40(2H, m), 3.43(1H, d, J=14.7 Hz), 3.75-3.83(1H, m), 3.84(1H, d, J=14.7 Hz), 4.09-4.14(1H, m), 4.57-4.62(1H, m), 7.15-7.32(16H, m)

FAB-MS(m/e, as $(C_{37}H_{44}N_4O_3+H)^+$): 593

EXAMPLE 65

(2R)-N-{(1-cyclohexylmethyl-4-piperidyl)methyl}-1-{(2S)-1-(3,3,3-triphenylpropanoyl)pyrrolidin-2-yl}carbonylpyrrolidine-2-carboxamide The title compound was prepared by a method similar to Step 3 of Example 17, using (2R)-N-(4-piperidylmethyl)-1-{(2S)-1-(3,3,3-triphenylpropanoyl)pyrrolidin-2-yl}carbonylpyrrolidine-2-carboxamide. The compound was obtained as a colorless oily substance.

$^1$H-NMR(CD$_3$OD, δppm): 0.85-1.83(20H, m), 1.85-2.00 (4H, m), 2.01-2.12(2H, m), 2.15-2.22(2H, m), 2.63-2.73 (1H, m), 2.81-3.01(4H, m), 3.37-3.53(2H, m), 3.53 (1H, d, J=15.0 Hz), 3.78-3.86(1H, m), 3.90(1H, d, J=15.0 Hz), 4.22(1H, t, J=7.4 Hz), 4.37-4.43(1H, m), 7.13-7.31(15H, m)

FAB-MS(m/e, as $(C_{44}H_{56}N_4O_3+H)^+$): 689

EXAMPLE 66

(2R)-N-{2-(4-piperidyl)ethyl}-1-{(2S)-1-(3,3,3-triphenylpropanoyl)pyrrolidin-2-yl}carbonylpyrrolidine-2-carboxamide The title compound was prepared by a method similar to Example 64, using 4-aminoethyl-1-(tert-butoxycarbonyl)piperidine which was synthesized by the method of B. C. Askew, et al. [*J. Med. Chem.*, Vol. 40, 1779-1788 (1997)]. The compound was obtained as a white foamy substance.

¹H-NMR(CDCl₃, δppm): 0.98-1.12(2H, m), 1.22-1.70 (7H, m), 1.72-2.00(6H, m), 2.25-2.34(1H, m), 5.08 (2H, dt, J=1.8, 12.0 Hz),2.69-2.88(2H, m), 2.97-3.08(2H, m), 3.12-3.42(3H, m),3.44(1H, d, J=14.8 Hz), 3.76-4.01(1H, m), 3.86 (1H, d, J=14.8 Hz), 4.14(1H, t, J=6.9 Hz), 4.58 (1H, d, J=7.7 Hz), 7.12-7.30(16H, m)

FAB-MS(m/e, as $(C_{38}H_{46}N_4O_3+H)^+$): 607

EXAMPLE 67

(2R)-N-{2-(1-cyclohexylmethyl-4-piperidyl)ethyl}-1-{(2S)-1-(3,3,3-triphenylpropanoyl)pyrrolidin-2-yl}carbonylpyrrolidine-2-carboxamide The title compound was prepared by a method similar to Step 3 of Example 17, using (2R)-N-{2-(4-piperidyl)ethyl}-1-{(2S) -1-(3,3,3-triphenylpropanoyl)pyrrolidin-2-yl}carbonylpyrrolidine-2-carboxamide. The compound was obtained as a colorless oily substance.

¹H-NMR(CD₃OD, δppm): 0.83-1.82(22H, m), 1.85-2.00 (4H, m), 2.01-2.10(2H, m), 2.15-2.21(2H, m), 2.64-2.77 (1H, m), 2.86-3.00 (3H, m), 3.10-3.22(1H, m), 3.38-3.50 (2H, m), 3.54(1H, d, J=15.3 Hz), 3.76-3.84(1H, m), 3.91 (1H, d, J=15.3 Hz),1.22(1H, t, J=7.3 Hz), 4.38-4.42(1H, m), 7.13-7.32(15H, m)

FAB-MS(m/e, as $(C_{45}H_{58}N_4O_3+H)^+$): 703

EXAMPLE 68

N-{3-(2-{((3R)-1-cyclohexylmethyl-3-piperidyl) methyl}amino-2-oxoethyl)amino-3-oxopropyl}-3,3,3-triphenylpropanamide (Step 1)

Synthesis of 2-amino-N-{((3R)-1-cyclohexylmethyl-3-piperidyl)methyl}acetamide

The title compound was prepared by conducting procedures similar to Steps 1-2 of Example 17, using (3R)-3-aminomethyl-1-(cyclohexylmethyl)piperidine and (tert-butoxycarbonyl)-glycine.

(Step 2)

Synthesis of N-{3-(2-{((3R)-1-cyclohexylmethyl-3-piperidyl)methyl}amino-2-oxoethyl)amino-3-oxopropyl}-3,3,3-triphenylpropanamide The title compound was prepared by successively conducting procedures similar to Steps 1-2 of Example 17 and Step 4 of Example 45, using 2-amino-N-{((3R) -1-cyclohexylmethyl-3-piperidyl)methyl}-acetamide and N-(tert-butoxycarbonyl)-β-alanine. The compound was obtained as a white foamy substance.

¹H-NMR(CDCl₃, δppm): 0.78-2.08(22H, m), 2.54-2.64 (2H,m), 3.14-3.27(4H, m), 3.56(2H, s), 3.75(2H, d, J=5.3 Hz), 5.88-5.95(2H, m), 6.39-6.42(1H, m),7.16-7.31(15H, m)

FAB-MS(m/e, as $(C_{39}H_{50}N_4O_3+H)^+$): 623

EXAMPLE 69

(2R,4S)-N-{(1-cyclohexylmethyl-3-piperidyl)methyl}-4-hydroxy-1-{(2S,4R)-1-(3,3,3-triphenylpropanoyl)pyrrolidin-2-yl}-carbonylpyrrolidine-2-carboxamide (Step 1)

Synthesis of (2R,4S)-N-{(1-cyclohexylmethyl-3-piperidyl)methyl}-4-hydroxypyrrolidine-2-carboxamide monohydrochloride The title compound was prepared by conducting a method similar to Steps 5-6 of Example 1, using 3-aminomethyl-1-(cyclohexylmethyl)piperidine and N-(tert-butoxycarbonyl)-trans-4-hydroxy-D-proline.

(Step 2)

Synthesis of (2R,4S)-N-{(1-cyclohexylmethyl-3-piperidyl)methyl}-4-hydroxy-1-{(2S,4R)-1-(3,3,3-triphenylpropanoyl)pyrrolidin-2-yl}carbonylpyrrolidine-2-carboxamide The title compound was prepared by successively conducting procedures similar to Steps 1-3 of Example 1, using (2R,4S)-N-{(1-cyclohexylmethyl-3-piperidyl) methyl}pyrrolidine-2-carboxamide monohydrochloride and N-(tert-butoxycarbonyl)-L-proline. The product was obtained as a white solid.

¹H-NMR(CDCl₃, δppm): 0.75-0.96(3H, m), 1.08-1.32 (4H, m), 1.38-2.20(19H, m), 2.30-2.43(1H, m), 2.56-2.85 (4H,m), 2.93-3.15(1H, m), 3.25-3.32(1H, m), 3.38-3.43 (2H, m), 3.85-3.93(2H, m), 4.00-4.10(1H, m), 4.38-4.49 (1H, m), 4.65(1H, dd, J=4.4, 8.2 Hz), 7.13-7.33(16H, m)

FAB-MS(m/e, as $(C_{44}H_{56}N_4O_4+H)^+$): 705

EXAMPLE 70

(2R,4S)-N-{(1-cyclohexylmethyl-3-piperidyl)methyl}-1-{(2S,4R)-4-hydroxy-1-(3,3,3-triphenylpropanoyl)pyrrolidin-2-yl}carbonyl-4-hydroxypyrrolidine-2-carboxyamide The title compound was prepared by a method similar to Step 2 of Example 55, using (2R,4S)-N-{(1-cyclohexylmethyl-3-piperidyl)methyl}-4-hydroxypyrrolidine-2-carboxamide monohydro-chloride. The compound was obtained as a white solid.

¹H-NMR(CDCl₃, δppm): 0.70-0.94(3H, m), 1.08-1.32 (4H, m), 1.39-2.13(17H, m), 2.14-2.23(2H, m), 2.42-2.53 (1H, m), 2.57-2.70(1H, m), 2.72-2.88(2H, m), 2.88-3.08(1H, m), 3.31-3.48(2H, m), 3.56-3.62(1H, m), 3.68-3.90(2H, m), 4.27-4.39(3H, m), 4.52-4.60 (1H,m),7.13-7.30(16H,m)

FAB-MS(m/e, as $(C_{44}H_{56}N_4O_5+H)^+$): 721

EXAMPLE 71

(2R)-1-{(2S,4S)-4-acetoxy-1-(3,3,3-triphenylpropanoly)pyrrolidin-2-yl}carbonyl-N-{((3R)-1-cyclohexylmethyl-3-piperidyl)-methyl}pyrrolidine-2-carboxamide A solution of 40 mg of (2R)-N-{((3R)-1-cyclohexylmethyl-3-piperidyl)methyl}-1-{(2S,4R)-4-(methylsulfonyloxy)-1-(3,3,3-triphenylpropanoyl)pyrrolidin-2-yl}carbonylpyrrolidine-2-carboxyamide and 30 mg of tetrabutylammonium acetate in 1 ml of N,N-dimethylformamide was stirred at 85° C. for 15 hours under heating. The reaction liquid was diluted with ethyl acetate, successively washed with water and saturated brine, and dried over anhydrous sodium sulfate. The solvent was distilled off under reduced pressure, and the resulting residue was purified with a preparative thin-layer chromatography (Kieselgel™ 60F₂₅₄, Art. 5744 (Merck), chloroform/methanol/28% aqueous ammonia=100/8/1), to provide 14 mg of the title compound as a colorless oily substance.

¹H-NMR(CDCl₃, δppm): 0.78-2.10(26H, m), 2.20-2.30 (1H, m), 2.32-2.50(2H, m), 2.60-2.68(1H, m), 2.73-3.08(4H, m), 3.30-3.40 (1H,m), 3.40(1H, d, J=14.6 Hz), 3.56-3.70(1H, m), 3.72-3.80 (1H, m), 4.00(1H, d, J=14.6 Hz), 4.25-4.33(2H, m), 4.52-4.56(1H, m), 7.13-7.45(16H, m)
FAB-MS(m/e, as $(C_{46}H_{58}N_4O_5+H)^+$): 747

EXAMPLE 72

(2R)-1-{(2S,4R)-4-acetoxy-1-(3,3,3-triphenylpropanoyl)pyrrolidin-2-yl}carbonyl-N-{((3R)-1-cyclohexylmethyl-3-piperidyl)methyl}pyrrolidine-2-carboxamide The title compound was prepared by successively conducting procedures similar to Step 1 of Example 57 and Example 71, using (2R)-N-{((3R)-1-cyclohexylmethyl-3-piperidyl)methyl}-1-{(2S,4S)-4-hydroxy-1-(3,3,3-triphenylpropanoyl)pyrrolidin-2-yl}carbonylpyrrolidine-2-carboxamide. The compound was obtained as a yellow oily substance.
$^1$H-NMR(CDCl$_3$, δppm): 0.70-0.98(4H, m), 1.10-1.38 (4H, m), 1.32(1H, t, J=10.7 Hz), 1.39-2.20(15H, m), 2.05 (3H, s), 2.27-2.38 (2H, m), 2.55-2.65(1H, m), 2.68-2.80 (1H, m), 2.98-3.18(3H, m), 3.31-3.40(1H, m), 3.44 (1H, d, J=15.3 Hz), 3.74(1H, dd, J=4.6, 11.5 Hz), 3.79-3.84 (1H, m), 3.85 (1H, d, J=15.3 Hz), 4.35(1H, t, J=8.0 Hz), 4.59 (1H, d, J=6.6 Hz), 5.20-5.27(1H, m), 7.14-7.32(16H, m)
FAB-MS(m/e, as $(C_{46}H_{58}N_4O_5+H)^+$): 747

EXAMPLE 73

N-{(1-cyclohexylmethyl-3-piperidyl)methyl}-1-{1-(3,3,3-triphenylpropanoyl)pyrrolidin-2-yl}carbonylpyrrolidine-2-carboxamide The title compound was prepared by successively conducting procedures similar to Examples 41 and 44, using methyl pyrrolidine-2-carboxylate monohydrochloride and N-(tert-butoxycarbonyl)-DL-proline. The compound was obtained as a colorless oily substance.
$^1$H-NMR(CDCl$_3$, δppm): 0.60-1.12(3H, m), 1.15-2.20 (24H, m), 2.24-2.38(1H, m), 2.46-2.90(3H, m), 2.98-3.19 (1H, m), 3.20-4.65(8H, m), 7.10-8.20(16H, m)
FAB-MS(m/e, as $(C_{44}H_{56}N_4O_3+H)^+$): 689

EXAMPLE 74

(2R)-1-{(2S,4R)-4-hydroxy-1-(3,3,3-triphenylpropanoyl)pyrrolidin-2-yl}carbonyl-N-{((3R)-1-propyl-3-piperidyl)methyl}-pyrrolidine-2-carboxamide The title compound was prepared by a method similar to Example 47, using propionaldehyde. The compound was obtained as a white solid.
$^1$H-NMR(CDCl$_3$, δppm): 0.80-2.06(18H, m), 2.20-2.32 (3H, m), 2.67(1H, d, J=11.4 Hz), 2.72-2.82(2H, m), 2.83-2.93 (1H, m), 2.96-3.08(1H, m), 3.30-3.36(1H, m), 3.39 (1H, d, J=14.2 Hz), 3.61(1H, dd, J=3.6, 11.2 Hz), 3.81-3.90 (1H, m), 3.96(1H, d,J=14.2 Hz), 4.28-4.37(2H, m), 4.56 (1H, d,J=8.0 Hz), 7.17-7.38(16H, m) ESI-MS(m/e, as $(C_{40}H_{50}N_4O_4+H)^+$): 651

EXAMPLE 75

(2R)-1-{(2S,4R)-4-hydroxy-1-(3,3,3-triphenylpropanoyl)pyrrolidin-2-yl}carbonyl-N-{((3R)-1-octyl-3-piperidyl)methyl}-pyrrolidine-2-carboxamide The title compound was prepared by a method similar to Example 47, using n-octanal. The compound was obtained as a white foamy substance.
$^1$H-NMR(CDCl$_3$, δppm): 0.83-0.95(6H, m), 1.20-1.83 (18H, m), 1.86-2.02(4H, m), 2.21-2.32(3H, m), 2.64-2.80 (3H, m), 2.83-2.91(1H, m), 3.00-3.10(1H, m), 3.31-3.36 (1H, m), 3.39(1H, d, J=14.4 Hz), 3.60(1H, dd, J=3.9, 10.9 Hz), 3.81-3.90(1H, m), 3.95(1H, d, J=14.4 Hz), 4.28-4.37(2H, m), 4.56(1H, dd, J=1.6, 7.9 Hz), 7.16-7.34(16H, m)
FAB-MS(m/e, as $(C_{45}H_{60}N_4O_4+H)^+$): 721

EXAMPLE 76

(2R)-N-{((3R)-1-cyclopropylmethyl-3-piperidyl)methyl}-1-{(2S,4R)-4-hydroxy-1-(3,3,3-triphenylpropanoyl)pyrrolidin-2-yl}carbonylpyrrolidine-2-carboxamide The title compound was prepared by a method similar to Example 47, using cyclopropanecarbaldehyde. The compound was obtained as a white solid.
$^1$H-NMR(CDCl$_3$, δppm): 0.04-0.10(2H, m), 0.45-0.53 (2H, m), 88(4H, t, J=6.8 Hz), 1.22-1.38(3H, m), 1.42-1.50 (1H, m), 1.55-2.05(6H, m), 2.16-2.32(3H, m), 2.62-2.80(2H, m), 2.88-2.98 (1H, m), 2.98-3.09(2H, m), 3.30-3.37(1H, m), 3.39 (1H, d, J=14.2 Hz), 3.61(1H, dd, J=3.8, 11.1 Hz), 3.82-3.91 (1H, m), 3.97(1H, d, J=14.2 Hz), 4.28-4.37(2H, m), 4.53-4.59 (1H, m), 7.17-7.38(16H, m)
FAB-MS(m/e, as $(C_{41}H_{50}N_4O_4+H)^+$): 663

EXAMPLE 77

(2R)-N-{((3R)-1-allyl-3-piperidyl)methyl}-1-{(2S, 4R)-4-hydroxy-1-(3,3,3-triphenylpronanoyl)pyrrolidin-2-yl}-carbonylpyrrolidine-2-carboxamide To a solution of 37 mg of (2R)-N-((3S)-3-piperidylmethyl)-1-{(2S)-1-(3,3,3-triphenylpropanoyl)pyrrolidin-2-yl}carbonylpyrrolidine-2-carboxamide in 0.9 ml of acetonitrile, 0.0055 ml of allyl bromide and 25 mg of potassium carbonate were added at room temperature, followed by 1.5 hours' stirring at 80° C. under heating. The reaction liquid was diluted with chloroform, washed successively with water and 1N aqueous sodium hydroxide solution, and dried over anhydrous sodium sulfate. After distilling the solvent off under reduced pressure, the resulting residue was purified with a preparative thin-layer chromatography (Kieselgel™ 60F$_{254}$, Art 5744 (Merck), chloroform/methanol/28% aqueous ammonia=100/10/1), to provide 23 mg of the title compound as a white solid.
$^1$H-NMR(CDCl$_3$, δppm): 0.80-2.10(15H, m), 2.24-2.33 (1H, m), 2.62-2.72(1H, m), 2.73-2.82(1H, m), 2.83-2.92 (1H, m), 2.93-2.9(1H, m), 3.00-3.10(1H, m), 3.30-3.36 (1H, m), 3.39(1H, d, J=14.1 Hz), 3.58-3.66(1H, m), 3.80-3.90 (1H, m), 3.95(1H, d, J=14.1 Hz), 4.28-4.37(2H, m), 4.52-4.58 (1H, m), 5.07-5.19(2H, m), 5.82-5.96(1H, m), 7.17-7.38(16H, m)
FAB-MS(m/e, as $(C_{40}H_{48}N_4O_4+H)^+$): 649

EXAMPLE 78

(2R)-N-{((3R)-1-cyclohexylmethyl-3-piperidyl)methyl}-1-{(2S,4R)-4-hydroxy-1-(2-methyl-3,3,3-triphenylpropanoyl)pyrrolidin-2-yl}carbonylpyrrolidine-2-carboxamide The title compound was prepared by successively conducting procedures similar to Step 4 of Example 45, Example 46 and Step 3 of Example 17, using 2-methyl-3,3,3-triphenylpropionic acid. The compound was obtained as a white solid.

¹H-NMR(CDCl₃, δppm): 0.70-2.40(31H, m), 2.60-2.90 (2H, m), 2.97-3.10(1H, m), 3.33-3.43(1H, m), 3.76-3.82(1H, m), 3.87-4.00(2H, m), 4.18-4.57(2H, m), 4.60-4.75(2H, m), 6.70-6.80(1H, m), 7.10-7.30(15H, m)
FAB-MS(m/e, as (C₄₅H₅₈N₄O₄+H)⁺): 719

EXAMPLE 79

(2R)-1-{(2S,4S)-4-acetylamino-1-(3,3,3-triphenyl-propanoyl)pyrrolidin-2-yl}carbonyl-N-{((3R)-1-cyclohexylmethyl-3-piperidyl)methyl}pyrrolidine-2-carboxamide To a solution of 22 mg of (2R)-1-{(2S,4S)-4-amino-1-(3, 3,3-triphenylpropanoyl)pyrrolidin-2-yl}carbonyl-N-{((3R)-1-cyclohexylmethyl-3-piperidyl)methyl}pyrrolidine-2-carboxamide in 1 ml of chloroform, 0.0089 ml of acetic anhydride and 0.0127 ml of pyridine were added at room temperature, followed by an hour's stirring at the same temperature. The reaction liquid was diluted with chloroform, washed successively with saturated aqueous sodium bicarbonate solution and saturated brine, and dried over anhydrous sodium sulfate. After distilling the solvent off under reduced pressure, the resulting residue was purified with a preparative thin-layer chromatography (Kieselgel™ 60F₂₅₄, Art 5744 (Merck), chloroform/methanol=8/1), to provide 18 mg of the title compound as a white solid.
¹H-NMR(CDCl₃, δppm): 0.78-0.93(4H, m), 1.12-1.86 (17H, m), 1.93(3H, s), 1.94-2.10(4H, m), 2.25-2.33(1H, m), 2.50-2.70(3H, m), 2.73-2.82(1H, m), 3.10-3.27(2H, m), 3.34-3.45(1H, m), 3.39(1H, d, J=14.2 Hz), 3.84-3.93(1H, m), 3.88 (1H, d, J=14.2 Hz), 4.17(1H, d, J=9.3 Hz), 4.42-4.51 (1H, m), 4.53-4.60(1H, m), 7.10-7.33(16H, m), 8.00-8.07 (1H, m)
FAB-MS(m/e, as (C₄₆H₅₉N₅O₄+H)⁺): 746

EXAMPLE 80

(2R)-N-{((3R)-1-cyclohexylmethyl-3-piperidyl)methyl}-1-{(2S,4S)-4-(methylsulfonylamino)-1-(3,3,3-triphenylpropanoyl)pyrrolidin-2-yl}carbonylpyrrolidine-2-carboxamide The title compound was prepared by a method similar to Step 1 of Example 57, using (2R)-1-{(2S,4S)-4-amino-1-(3, 3,3-triphenylpropanoyl)pyrrolidin-2-yl}carbonyl-N-{((3R)-1-cyclohexyl-methyl-3-piperidyl)methyl}pyrrolidine-2-carboxamide. The compound was obtained as a white solid.
¹H-NMR(CDCl₃, δppm): 0.78-0.97(3H, m), 1.05-2.10 (23H, m), 2.25-2.34(1H, m), 2.53-2.85(3H, m), 2.89(3H, s), 3.07-3.20(1H, m), 3.32-3.55(3H, m), 3.83-4.00(3H, m), 4.15 (1H, d, J=8.7 Hz), 4.55-4.61(1H, m), 7.03-7.13(1H, m), 7.15-7.40(16H, m)
FAB-MS(m/e, as (C₄₅H₅₉N₅O₅S+H)⁺): 783

EXAMPLE 81

(2R)-N-{((3R)-1-cyclohexylmethyl-3-piperidyl)methyl}-1-{(2S)-4-oxo-1-(3,3,3-triphenylpropanoyl)pyrrolidin-2-yl}carbonylpyrrolidine-2-carboxamide To a solution of 0.0037 ml of oxaryl chloride in 0.3 ml of dichloromethane, 0.0065 ml of dimethyl sulfoxide was added at −78° C., followed by 20 minutes' stirring at the same temperature. Then a solution of 25 mg of (2R)-N-{((3R)-1-cyclohexylmethyl-3-piperidyl)methyl}-1-{(2S,4R)-4-hydroxy-1-(3,3,3-triphenylpropanoyl)pyrrolidin-2-yl}carbonylpyrrolidine-2-carboxamide in 0.9 ml of dichloromethane was added at the same temperature, followed by 30 minutes' stirring, addition of 0.0024 ml of triethylamine at the same temperature, and 20 minutes' stirring at room temperature. The reaction liquid was diluted with chloroform, washed with saturated brine and dried over anhydrous sodium sulfate. Distilling the solvent off under reduced pressure, the resulting residue was purified with a preparative thin-layer chromatography (Kieselgel™ 60F₂₅₄, Art5744 (Merck); chloroform/methanol=9/1), to provide 18 mg of the title compound as a pale pink solid.
¹H-NMR(CDCl₃, δppm): 0.78-2.20(22H, m) ,2.21-2.36 (1H, m), 2.47-2.52(2H, m), 2.55-2.90(3H, m), 2.98-3.20(3H, m), 3.27-3.55(2H, m), 3.80-4.03(3H, m), 4.50-4.63(2H, m), 6.88-7.05(1H, m), 7.10-7.40(15H, m)
FAB-MS(m/e, as (C₄₄H₅₄N₄O₄+H)⁺): 703

EXAMPLE 82

(2R)-1-{(2S,3R,4S)-3,4-dihydroxy-1-(3,3,3-triphenylpropanoyl)pyrrolidin-2-yl}carbonyl-N-((3S)-3-piperidylmethyl)pyrrolidine-2-carboxamide (Step 1)
Synthesis of (2S)-3,4-dehydro-1-(3,3,3-triphenylpropanoyl)pyrrolidine-2-carboxylic acid
The title compound was prepared by successively conducting procedures similar to Step 1 of Example 24 and Steps 2-4 of Example 1, using N-(tert-butoxycarbonyl)-3,4-dehydro-L-proline.

(Step 2)
Synthesis of (2R)-N-({(3R)-1-(tert-butoxycarbonyl)-3-piperidyl}methyl)-1-{(2S)-3,4-dehydro-1-(3,3,3-triphenyl-propanoyl)pyrrolidine-2-yl}carbonylpyrrolidine-2-carboxamide
The title compound was prepared by a method similar to Step 4 of Example 45, using (2S)-3,4-dehydro-1-(3,3,3-triphenylpropanoly)pyrrolidine-2-carboxylic acid and 2R)-N-({(3R)-1-(tert-butoxycarbonyl)-3-piperidyl}methyl)pyrrolidine-2-carboxamide.

(Step 3)
Synthesis of (2R)-N-({(3R)-1-(tert-butoxycarbonyl)-3-piperidyl}methyl)-1-{(2S,3R,4S)-3,4-dihydroxy-1-(3,3,3-triphenylpropanoyl)pyrrolidin-2-yl}carbonylpyrrolidine-2-carboxamide
To a solution of 29 mg of (2R)-N-({(3R)-1-(tert-butoxycarbonyl)-3-piperidyl}methyl)-1-{(2S)-3,4-dehydro-1-(3,3, 3-triphenylpropanoyl)pyrrolidin-2-yl}carbonylpyrrolidine-2-carboxamide in 1.5 ml of 33% hydrous acetonitrile, 6 mg of N-methylmorpholine-N-oxide and then 0.0027 ml of 2% aqueous osmium tetroxide solution were added under cooling with ice, followed by 66 hours' stirring at room temperature. An aqueous sodium thiosulfate solution was added to the reaction liquid, followed by extraction with chloroform and drying over anhydrous sodium sulfate. Distilling the solvent off under reduced pressure, the resulting residue was purified with a preparative thin-layer chromatography (Kieselgel™ 60F₂₅₄, Art 5744 (Merck), chloroform/methanol=10/1) to provide 21 mg of the title compound.

(Step 4)
Synthesis of (2R)-1-{(2S,3R,4S)-3,4-dihydroxy-1-(3,3,3-triphenylpropanoly)pyrrolidin-2-yl}carbonyl-N-((3S)-3-piperidylmethyl)-pyrrolidine-2-carboxamide
The title compound was prepared by a method similar to Step 2 of Example 17, using (2R)-N-({(3R)-1-(tert-butoxycarbonyl)-3-piperidyl}methyl)-1-{(2S,3R,4S)-3,4-dihydroxy-1-(3,3,3-triphenylpropanoyl)pyrrolidin-2-yl}carbonylpyrrolidine-2-carboxamide. The compound was obtained as a white solid.

$^1$H-NMR(CDCl$_3$, δppm): 0.80-2.10(12H, m), 2.10-2.25 (2H, m), 2.48-2.60(1H, m), 2.65-2.94(4H, m), 3.45 (1H, d, J=14.8 Hz), 3.50-3.68(2H, m), 3.77(1H, d, J=14.8 Hz), 3.78-3.84(1H, m), 4.10-4.20(3H, m), 4.51-4.56(1H, m), 7.17-7.32 (16H, m)

FAB-MS(m/e, as (C$_{37}$H$_{44}$N$_4$O$_5$+H)$^+$): 625

EXAMPLE 83

(2R)-N-{((3R)-1-ethyl-3-piperidyl)methyl}-1-{(2S, 3R,4S)-3,4-dihydroxy-1-(3,3,3-triphenylpropanoyl) pyrrolidin-2-yl}carbonylpyrrolidine-2-carboxamide The title compound was prepared by a method similar to Example 77, using (2R)-1-{(2S,3R,4S)-3,4-dihydroxy-1-(3, 3,3-triphenylpropanoyl)pyrrolidin-2-yl}carbonyl-N-((3S)-3-piperidyl-methyl)pyrrolidine-2-carboxamide and ethyl iodide. The compound was obtained as a white solid.

$^1$H-NMR(CDCl$_3$, δppm): 0.77-2.10(15H, m), 2.20-2.28 (1H, m), 2.30-2.42(2H, m), 2.46-2.60(1H, m), 2.73-2.82(1H, m), 2.84-2.93(2H, m), 2.94-3.04(1H, m), 3.42(1H, d, J=14.5 Hz), 3.50-3.64(2H, m), 3.76-3.83(1H, m), 3.85(1H, d, J=14.5 Hz), 4.09-4.17(2H, m), 4.18-4.22(1H, m), 9.06 (1H, dd, J=1.4, 8.2 Hz), 7.13-7.30(16H, m)

FAB-MS(m/e, as (C$_{39}$H$_{48}$N$_4$O$_5$+H)$^+$): 653

EXAMPLE 84

(2R)-N-{((3R)-1-cyclohexylmethyl-3-piperidyl)methyl})-1-{(2S,3R,4S)-3,4-dihydroxy-1-(3,3,3-triphenylpropanoyl)pyrrolidin-2-yl}carbonylpyrrolidine-2-carboxamide The title compound was prepared by a method similar to Step 3 of Example 17, using (2R)-1-{(2S,3R,4S)-3,4-dihydroxy-1-(3,3,3-triphenylpropanoyl)pyrrolidin-2-yl}-carbonyl-N-((3S)-3-piperidylmethyl)pyrrolidine-2-carboxamide. The compound was obtained as a white solid.

$^1$H-NMR(CDCl$_3$, δppm): 0.75-0.98(3H, m), 1.12-1.42 (5H, m), 1.43-2.04(15H, m), 2.05(2H, d,J=6.5 Hz), 2.18-2.27 (1H, m), 2.28-2.40(1H, m), 2.57-2.63(1H, m), 2.70-2.80(1H, m), 2.93-3.12(2H, m), 3.44(1H, d, J=14.5 Hz), 3.51-3.63(2H, m), 3.76-3.80(1H, m), 3.81(1H, d, J=14.5 Hz), 4.12-4.19(2H, m), 4.20-4.25(1H, m), 4.49-4.54(1H, m), 7.13-7.32(16H, m)

FAB-MS(m/e, as (C$_{44}$H$_{56}$N$_4$O$_5$+H)$^+$): 721

EXAMPLE 85

(2R)-1-{(2S,4R)-4-hydroxy-1-(3,3,3-triphenylpropanoyl)pyrrolidin-2-yl}carbonyl-N-{((3R)-1-isobutyl-3-piperidyl)methyl}-pyrrolidine-2-carboxamide The title compound was prepared by a method similar to Example 47, using isobutylaldehyde. The compound was obtained as a colorless oily substance.

$^1$H-NMR(CDCl$_3$, δppm): 0.75-2.10(22H, m), 2.22-2.32 (1H, m), 2.55-2.85(4H, m), 3.01-3.11(1H, m), 3.30-3.43 (2H, m),3.55-3.68(1H, m), 3.80-4.00(2H, m), 4.27-4.38(2H, m), 4.50-4.59(1H, m), 7.13-7.40(16H, m)

ESI-MS(m/e, as (C$_{41}$H$_{52}$N$_4$O$_4$+H)$^+$): 665

EXAMPLE 86

(2R)-N-{((3R)-1-propyl-3-piperidyl)methyl}-1-{(2S)-1-(3,3,3-triphenylpropanoyl)pyrrolidin-2-yl}carbonylpyrrolidine-2-carboxamide The title compound was prepared by a method similar to Step 3 of Example 17, using (2R)-N-((3S)-3-piperidylmethyl)-1-{(2S)-1-(3,3,3-triphenylpropanoyl)pyrrolidin-2-yl}carbonylpyrrolidine-2-carboxamide and propionaldehyde. The product was obtained as a white solid.

$^1$H-NMR(CDCl$_3$, δppm): 0.75-2.10(16H, m), 0.90 (3H, t, J=7.3 Hz), 2.23-2.42(3H, m), 2.69-2.86(2H, m), 2.87-3.07 (3H, m), 3.29-3.40 (2H, m), 3.42 (1H, d, J=14.2 Hz),3.78-3.88(1H, m), 3.98(1H, d, J=14.2 Hz), 4.02-4.10(1H, m), 4.53-4.59(1H, m), 7.15-7.40(16H, m)

ESI-MS(m/e, as (C$_{40}$H$_{50}$N$_4$O$_3$+H)$^+$): 635

EXAMPLE 87

(2R)-N-{((3R)-1-butyl-3-piperidyl)methyl}-1-{(2S)-1-(3,3,3-triphenylpropanoyl)pyrrolidin-2-yl}carbonylpyrrolidine-2-carboxamide The title compound was prepared by a method similar to Example 85, using n-butylaldehyde. The product was obtained as a white solid.

$^1$H-NMR(CDCl$_3$, δppm): 0.80-2.50(21H, m), 0.92 (3H, t, J=7.3 Hz), 2.69-2.83(2H, m), 2.85-3.09(3H, m), 3.29-3.40 (2H, m), 3.41 (1H, d, J=14.6 Hz), 3.78-3.86(1H, m), 3.99(1H, d, J=14.6 Hz), 4.02-4.08(1H, m), 4.52-4.60(1H, m), 7.15-7.40(16H, m)

ESI-MS(m/e, as (C$_{41}$H$_{52}$N$_4$O$_3$+H)$^+$): 649

EXAMPLE 88

(2R)-N-{(1-benzyl-2-piperidyl)methyl}-1-{(2S)-1-(3,3,3-triphenylpropanoyl)pyrrolidin-2-yl}carbonylpyrrolidine-2-carboxamide The title compound was prepared by a method similar to Example 63, using 2-aminomethyl-1-benzylpiperidine [cf. *Chem. Pharm. Bull.*, 43, 1137-1147 (1995)]. The compound was obtained as a white solid.

$^1$H-NMR(CDCl$_3$, δppm): 0.70-2.08(13H, m), 2.27-2.39 (1H, m), 2.42-2.59(1H, m), 2.60-2.85(2H, m), 3.80-3.45(6H, m), 3.50-4.18(5H, m), 4.57-4.62(1H, m), 7.10-7.40(21H, m)

ESI-MS(m/e, as (C$_{44}$H$_{50}$N$_4$O$_3$+H)$^+$): 683

EXAMPLE 89

(2R)-1-((2S,4R)-4-hydroxy-1-{3,3,3-tris(4-chlorophenyl)-propanoyl}pyrrolidin-2-yl)carbonyl-N-{((3S)-3-piperidyl)methyl}-pyrrolidine-2-carboxamide The title compound was prepared by successively conducting procedures similar to Step 4 of Example 45 and Example 46, using 3,3,3-tris(4-chlorophenyl)propionic acid. The product was obtained as a white solid.

$^1$H-NMR(CDCl$_3$, δppm): 0.80-2.10(13H, m), 2.27-2.35 (1H, m), 2.48-2.59(2H, m), 2.84-3.06(4H, m), 3.34-3.42(1H, m), 3.36(1H, d, J=15.0 Hz), 3.61(1H, dd, J=3.8, 11.0 Hz), 3.79 (1H, d, J=15.0 Hz), 3.80-3.87(1H, m), 4.37-4.48(2H, m), 4.55(1H, d, J=6.3 Hz), 7.03-7.10(1H, m), 7.14(6H, d, J=8.7 Hz), 7.25(6H, d, J=8.7 Hz)

ESI-MS(m/e, as (C$_{37}$H$_{41}$Cl$_3$N$_4$O$_4$+H)$^+$): 711

EXAMPLE 90

(2R)-1-((2S,4R)-4-hydroxy-1-{3,3,3-tris(4-fluorophenyl)-propanoyl}pyrrolidin-2-yl)carbonyl-N-{((3S)-3-piperidyl)methyl}-pyrrolidine-2-carboxamide The title compound was prepared by successively conducting procedures similar to Step 4 of Example 45 and Example 46, using 3,3,3-tris(4-fluorophenyl)propionic acid. The product was obtained as a pale yellow solid.

$^1$H-NMR(CDCl$_3$, δppm): 0.83-2.07(12H, m), 2.08-2.18 (1H, m), 2.25-2.34(1H, m), 2.48-2.60(2H, m), 2.88-3.05(4H, m), 3.32-3.40 (1H, m), 3.41(1H, d, J=15.1 Hz), 3.58-3.63(1H, m), 3.77(1H, d, J=15.1 Hz), 3.80-3.88(1H, m), 4.37-4.50(2H, m), 4.51-4.57(1H, m), 6.96(6H, dd, J$_{HF}$=8.6 Hz, J$_{HH}$=8.6 Hz), 7.05-7.20(1H, m), 7.17(6H, dd, J$_{HF}$=5.3 Hz, J$_{HH}$=8.6 Hz)

ESI-MS(m/e, as (C$_{37}$H$_{41}$F$_3$N$_4$O$_4$+H)$^+$): 663

EXAMPLE 91

(2R)-1-((2S,4R)-4-hydroxy-1-{3,3,3-tris(4-methylphenyl)-propanoyl}pyrrolidin-2-yl)carbonyl-N-{((3S)-3-piperidyl)methyl}pyrrolidine-2-carboxamide (Step 1)
Synthesis of methyl 3,3,3-tris(4-cholorophenyl)propionate The title compound was prepared by a method similar to Step 1 of Example 24, using 3,3,3-tris(4-chlorophenyl)propionic acid.

(Step 2)
Synthesis of methyl 3,3,3-tris(4-vinylphenyl)propionate

The title compound was synthesized referring to Shirakawa, et al.'s method [*J. Chem. Soc.*, Perkin Trans. 1, 2449-2450 (1997)]. To a solution of 71 mg of nickel (II)-acetylacetonate dihydrate and 289 mg of triphenylphosphine in 2 ml of 1,2-dimethoxyethane, 0.544 ml of 1.0 M diisobutylaluminium hydride-toluene solution was added at room temperature in nitrogen atmosphere, and the whole system was added to a solution of 364 mg of methyl 3,3,3-tris (4-chlorophenyl)-propionate and 1.01 g of vinyltributyltin in 5 ml of 1,2-dimethoxy-ethane at room temperature, followed by 22 hours' stirring at 80° C. Further, a system formed by adding 0.544 ml of 1.0 M diisobutyl-aluminum hydride-toluene solution to a solution of 71 mg of nickel (II)-acetylacetonate dihydrate and 289 mg of triphenylphosphine in 2 ml of 1,2-dimethoxyethane at room temperature in nitrogen atmosphere was added at room temperature, followed by 17 hours' stirring at 80° C. under heating. The reaction liquid was cooled to room temperature and 1N potassium fluoride was added, followed by 2 hours' stirring at room temperature. Filtering the reaction liquid through cerite, the filtrate was diluted with ethyl acetate, washed successively with water and saturated brine, and dried over anhydrous sodium sulfate. Distilling the solvent off under reduced pressure, the resulting residue was purified by means of silica gel column chromatography (eluting solvent: hexane/ethyl acetate=300/7—hexane/ethyl acetate=300/10) to provide 166 mg of the title compound.

(Step 3)
Synthesis of 3,3,3-tris(4-vinylphenyl)propionic acid

Fifty-four (54) mg of methyl 3,3,3-tris(4-vinylphenyl)-propionate was suspended in 0.5 ml of dioxane, and to the suspension 0.5 ml of 4N aqueous lithium hydroxide solution was added at room temperature, followed by 17 hours' stirring at 90° C. under heating. The reaction liquid was made acidic by addition of 1N hydrochloric acid, extracted with chloroform and dried over anhydrous sodium sulfate. Distilling the solvent off under reduced pressure, 52.5 mg of the title compound was obtained.

(Step 4)
Synthesis of (2R)-N-({(3R)-1-(tert-butoxycarbonyl)-3-piperidyl}methyl)-1-((2S,4R)-4-(tert-butoxy)-1-{3,3,3-tris (4-vinyl-phenyl)propanoyl}pyrrolidin-2-yl)carbonylpyrrolidine-2-carboxamide The title compound was prepared by a method similar to Step 4 of Example 45, using 3,3,3-tris(4-vinylphenyl)propionic acid.

(Step 5)
Synthesis of (2R)-N-({(3R)-1-(tert-butoxycarbonyl)-3-piperidyl}methyl)-1-((2S,4R)-4-(tert-butoxy)-1-{3,3,3-tris (4-hydroxymethylphenyl)propanoyl}pyrrolidin-2-yl)carbonylpyrrolidine-2-carboxamide To a solution of 30.6 mg of (2R)-N-({(3R)-1-(tert-butoxycarbonyl)-3-piperidyl}methyl)-1-((2S,4R)-4-(tert-butoxy)-1-{3,3,3-tris(4-vinylphenyl)propanoyl}pyrrolidin-2-yl)carbonylpyrrolidine-2-carboxamide and 48 mg of sodium periodate in 3 ml of 50% hydrous acetonitrile, 0.023 ml of 2% aqueous osmium tetroxide solution was added at room temperature in nitrogen atmosphere, followed by 20 hours' stirring at the same temperature. To the reaction liquid 41 mg of sodium borohydride was added under cooling with ice, followed by 4 hours' stirring at room temperature. To the reaction liquid an aqueous sodium thiosulfate solution was added, followed by filtration with cerite, extraction with chloroform, and drying over anhydrous sodium sulfate. Distilling the solvent off under reduced pressure, the resulting residue was purified by preparative thin layer chromatography [Kieselgel™ 60F$_{254}$, Art 5744 (Merck); chloroform/methanol=10/1], to provide 8.4 mg of the title compound.

(Step 6)
Synthesis of (2R)-1-((2S,4R)-4-hydroxy-1-{3,3,3-tris(4-methylphenyl)propanoyl}pyrrolidin-2-yl)carbonyl-N-{((3S)-3-piperidyl)methyl}pyrrolidine-2-carboxamide The title compound was prepared by successively conducting procedures similar to Example 79, Step 2 of Example 45 and Example 46, using (2R)-N-({(3R)-1-(tert-butoxycarbonyl)-3-piperidyl}methyl)-1-((2S,4R)-4-(tert-butoxy)-1-{3,3,3-tris(4-hydroxymethylphenyl)propanyl}pyrrolidin-2-yl)carbonylpyrrolidine-2-carboxamide. The product was obtained as a white solid.

$^1$H-NMR(CDCl$_3$, δppm): 0.82-2.29(14H, m), 2.30(9H,s), 2.50-2.67(2H, m), 2.92(2H, t, J=6.2 Hz), 2.98-3.10(2H, m), 3.32-3.41(1H, m), 3.33(1H, d, J=14.1 Hz), 3.58-3.68(1H, m), 3.86(1H, d, J=14.1 Hz), 3.87-3.91(1H, m), 4.25-4.36(2H, m), 4.50-4.58(1H, m), 7.06(6H, d, J=8.3 Hz), 7.18(6H, d, J=8.3 Hz), 7.37-7.46(1H, m)

ESI-MS(m/e, as (C$_{40}$H$_{50}$N$_4$O$_4$+H)$^+$): 651

EXAMPLE 92

(2R)-1-((2S,4R)-4-hydroxy-1-{3,3,3-tris(4-ethylphenyl)-propanoyl}pyrrolidin-2-yl)carbonyl-N-{((3S)-3-piperidyl)methyl}pyrrolidine-2-carboxamide (Step 1)
Synthesis of (2R)-N-({(3R)-1-(tert-butoxycarbonyl)-3-piperidyl}methyl)-1-((2S,4R)-4-(tert-butoxy)-1-{3,3,3-tris (4-ethylphenyl)propanoyl}pyrrolidin-2-yl)carbonylpyrrolidine-2-carboxamide To a solution of 15.6 mg of (2R)-N-({(3R)-1-(tert-butoxy-carbonyl)-3-piperidyl}methyl)-1-((2S,4R)-4-(tert-butoxy)-1-{3,3,3-tris(4-vinylphenyl)-propanoyl}pyrrolidin-2-yl)carbonylpyrrolidine-2-carboxamide in 0.6 ml of methanol, 5 mg of 10% palladium-carbon catalyst was added at room temperature, followed by 4.5 hours' stirring in hydrogen atmosphere. After filtering the catalyst off, the solvent was distilled off under reduced pressure to provide 12 mg of the title compound.

(Step 2)

Synthesis of (2R)-1-((2S,4R)-4-hydroxy-1-{3,3,3-tris-(4-ethylphenyl)-propanoyl}pyrrolidin-2-yl)carbonyl-N-{((3S)-3-piperidyl)methyl}pyrrolidine-2-carboxamide The title compound was prepared by a method similar to Example 46, using (2R)-N-({(3R)-1-(tert-butoxycarbonyl)-3-piperidyl}methyl)-1-((2S,4R)-4-(tert-butoxy)-1-{3,3,3-tris-(4-ethylphenyl)propanoyl}pyrrolidin-2-yl)carbonylpyrrolidine-2-carboxamide. The compound was obtained as a white solid.

$^1$H-NMR(CDCl$_3$, δppm): 0.97-2.10(12H, m), 1.22 (9H, t, J=7.6 Hz), 2.12-2.35(2H, m), 2.48-2.60(2H, m), 2.62 (6H, q, J=7.6 Hz), 2.78-3.03(4H, m), 3.30-3.40(1H, m), 3.34 (1H, d, J=14.0 Hz), 3.58-3.65(1H, m), 3.80-3.86(1H, m), 3.87(1H, d, J=14.0 Hz), 4.27-4.38(2H, m), 4.52-4.59(1H, m), 7.08(6H, d, J=8.3 Hz), 7.20(6H, d, J=8.3 Hz), 7.27-7.40(1H, m)

ESI-MS(m/e, as (C$_{43}$H$_{56}$N$_4$O$_4$+H)$^+$): 693

EXAMPLE 93

(2R)-N-{((3R)-1-ethyl-3-piperidyl)methyl}-1-((2S,4R)-4-hydroxy-1-{3,3,3-tris(4-ethylphenyl)propanoyl}pyrrolidin-2-yl)-carbonylpyrrolidine-2-carboxamide The title compound was prepared by a method similar to Example 77, using (2R)-1-((2S,4R)-4-hydroxy-1-{3,3,3-tris(4-ethylphenyl)propanoyl}pyrrolidin-2-yl)carbonyl-N-{((3S)-3-piperidyl)methyl}pyrrolidine-2-carboxamide and ethyl iodide. The compound was obtained as a white solid.

$^1$H-NMR(CDCl$_3$, δppm): 0.78-1.15(6H, m), 1.22 (9H, t, J=7.6 Hz), 1.28-2.10(11H, m), 2.24-2.32(1H, m), 2.32-2.48 (2H, m), 2.61(6H, q, J=7.6 Hz), 2.75-3.04 (4H, m), 3.29-3.40 (2H, m), 3.60-3.68(1H, m), 3.83-4.01 (2H, m), 4.20-4.33(2H, m), 4.50-4.59(1H, m), 7.08 (6H, d, J=8.4 Hz), 7.23(6H, d, J=8.4 Hz), 7.30-7.42(1H, m)

ESI-MS(m/e, as (C$_{45}$H$_{60}$N$_4$O$_4$+H)$^+$): 721

EXAMPLE 94

(2R)-1-{(2S,4R)-4-hydroxy-1-(3,3,3-triphenylpropanoyl)pyrrolidin-2-yl}carbonyl-N-((3R)-3-piperidylmethyl)pyrrolidine-2-carboxamide The title compound was prepared by successively conducting procedures similar to Steps 1-4 of Example 45 and Example 46, using (3S)-3-aminomethyl-1-(tert-butoxycarbonyl)piperidine. The compound was obtained as a white solid.

$^1$H-NMR(CDCl$_3$, δppm): 0.88-2.08(12H, m), 2.21 (1H, t, J=11.0 Hz), 2.27-2.36(1H, m), 2.46-2.58(2H, m), 2.78-2.99 (3H, m), 3.00-3.12(1H, m), 3.30-3.40(1H, m), 3.44 (1H, d, J=14.7 Hz), 3.62(1H, dd, J=4.0, 10.9 Hz), 3.78-3.85 (1H, m), 3.86(1H, d, J=14.7 Hz), 4.30-4.40(2H, m), 4.55-4.62(1H, m), 7.15-7.38(16H, m)

ESI-MS(m/e, as (C$_{37}$H$_{44}$N$_4$O$_4$+H)$^+$): 609

EXAMPLE 95

(2R)-1-{(2S,4R)-4-hydroxy-1-(3,3, 3-triphenylpropanoyl)pyrrolidin-2-yl}carbonyl-N-{((3S)-1-methyl-3-piperidyl)methyl}pyrrolidine-2-carboxamide The title compound was prepared by a method similar to Step 3 of Example 17, using (2R)-1-{(2S,4R)-4-hydroxy-1-(3,3,3-triphenypropanoyl)pyrrolidin-2-yl}carbonyl-N-((3R)-3-piperidyl-methyl)pyrrolidine-2-carboxamide and 37% aqueous formaldehyde solution. The compound was obtained as a white solid.

$^1$H-NMR(CDCl$_3$, δppm): 0.68-2.10(13H, m), 2.24(3H, s), 2.25-2.33(1H, m), 2.46-2.55(1H, m), 2.57-2.68(1H, m), 2.73-2.86(2H, m), 3.03-3.14(1H, m), 3.29-3.40(1H, m), 3.42(1H, d, J=14.8 Hz), 3.61(1H, dd, J=4.0, 10.7 Hz), 3.79-3.86(1H, m), 3.87(1H, d, J=14.8 Hz), 4.32-4.40(2H, m), 4.54-4.60(1H, m), 7.15-7.35(16H,m)

ESI-MS(m/e, as (C$_{38}$H$_{46}$N$_4$O$_4$+H)$^+$): 623

EXAMPLE 96

(2R)-N-{((3S)-1-ethyl-3-piperidyl)methyl}-1-{(2S,4R)-4-hydroxy-1-(3,3,3-triphenylpropanoyl)pyrrolidin-2-yl}carbonylpyrrolidin-2-carboxamide The title compound was prepared by a method similar to Example 95, using acetaldehyde. The product was obtained as a white solid.

$^1$H-NMR(CDCl$_3$, δppm): 0.78-2.32(14H, m), 1.06 (3H, t, J=7.2 Hz), 2.33-2.47(3H, m), 2.71-2.79(1H, m), 2.82-2.92 (2H, m), 3.00-3.12(1H, m), 3.29-3.38(1H, m), 3.44(1H, d, J=14.8 Hz), 3.59(1H, dd, J=4.0, 10.9 Hz), 3.79-3.85(1H, m), 3.86(1H, d, J=14.8 Hz), 4.32-4.40(2H, m), 4.55(1H, d, J=6.6 Hz), 7.13-7.32(16H, m)

ESI-MS(m/e, as (C$_{39}$H$_{48}$N$_4$O$_4$+H)$^+$): 637

EXAMPLE 97

(2R)-1-{(2S,4R)-4-hydroxy-1-(3,3,3-tripheny}propanoyl)pyrrolidin-2-yl}carbonyl-N-{((3S)-1-propyl-3-piperidyl)methyl}pyrrolidine-2-carboxamide The title compound was prepared by a method similar to Example 95, using propionaldehyde. The product was obtained as a white solid.

$^1$H-NMR(CDCl$_3$, δppm): 0.69-2.08(15H, m), 0.87 (3H, t, J=7.4 Hz), 2.08-2.38(3H, m), 2.49-2.60(1H, m), 2.72-2.93 (3H, m), 3.00-3.13(1H, m), 3.29-3.40(1H, m), 3.41 (1H, d, J=14.6 Hz), 3.60(1H, dd, J=3.8, 11.0 Hz), 3.80-3.87 (1H, m), 3.87(1H, d, J=14.6 Hz), 4.30-4.44(2H, m), 4.55-4.62 (1H, m), 7.15-7.43(16H, m)

ESI-MS(m/e, as (C$_{40}$H$_{50}$N$_4$O$_4$+H)$^+$): 651

EXAMPLE 98

(2R)-N-{((3S)-1-cyclopropylmethyl-3-piperidyl)methyl}-1-{(2S,4R)-4-hydroxy-1-(3,3,3-triphenyl-propanoyl)pyrrolidin-2-yl}carbonylpyrrolidine-2-carboxamide The title compound was prepared by a method similar to Example 95, using cyclopropanecarbaldehyde. The product was obtained as a white solid.

$^1$H-NMR(CDCl$_3$, δppm): 0.05-0.18(2H, m), 0.43-0.55 (2H, m), 0.70-2.07(14H, m), 2.18-2.34(3H, m), 2.42-2.55

(1H, m), 2.78-2.94(2H, m), 2.97-3.15(2H, m), 3.30-3.41(1H, m), 3.43(1H, d, J=14.9 Hz), 3.60(1H, dd, J=4.0, 11.1 Hz), 3.78-3.86(1H, m), 3.89(1H, d, J=14.9 Hz), 4.30-4.40(2H, m), 4.57(1H, d, J=7.3 Hz), 7.12-7.30(16H, m)
ESI-MS(m/e, as $(C_{41}H_{50}N_4O_4+H)^+$): 663

EXAMPLE 99

(2R)-1-((2S,4R)-4-hydroxy-1-{3,3,3-tris(4-chlorophenyl)-propanoyl}pyrrolidin-2-yl)carbonyl-N-{((3R)-3-piperidyl)methyl}pyrrolidine-2-carboxamide (Step 1)
Synthesis of (2R)-N-({(3S)-1-(tert-butoxycarbonyl)-3-peperidyl}methyl)-1-{(2S,4R)-4-(tert-butoxy)pyrrolidin-2-yl}-carbonylpyrrolidine-2-carboxamide
The title compound was prepared by a method similar to Steps 1-3 of Example 45, using (3S)-3-aminomethyl-1-(tert-butoxycarbonyl)piperidine.

(Step 2)
Synthesis of (2R)-1-((2S,4R)-4-hydroxy-1-{3,3,3-tris(4-chlorophenyl)propanoyl}pyrrolidin-2-yl)carbonyl-N-{((3R)-3-piperidyl)methyl}pyrrolidine-2-carboxamide
The title compound was prepared by a method similar to Example 88, using (2R)-N-({(3S)-1-(tert-butoxycarbonyl)-3-peperidyl}methyl)-1-{(2S,4R)-4-(tert-butoxy)pyrrolidin-2-yl}-carbonylpyrrolidine-2-carboxamide. The product was obtained as a white foamy substance.
$^1$H-NMR(CDCl$_3$, δppm): 0.83-1.82(8H, m), 1.88-2.10 (4H, m), 2.13-2.22(1H, m), 2.28-2.40(2H, m), 2.48-2.59(1H, m), 2.80-2.88(1H, m), 2.90-3.07(2H, m), 3.08-3.20(1H, m), 3.29-3.39(1H, m), 3.39(1H, d, J=15.3 Hz), 3.60-3.66(1H, m), 3.73(1H, d, J=15.3 Hz), 3.77-3.86(1H, m), 4.39-4.52(2H, m), 4.57(1H, d, J=5.6 Hz), 7.02-7.20(1H, m), 7.12(6H, d, J=8.9 Hz), 7.24(6H, d, J=8.9 Hz)
ESI-MS(m/e, as $(C_{37}H_{41}Cl_3N_4O_4+H)^+$): 711

EXAMPLE 100

(2R)-1-((2S,4R)-4-hydroxy-1-{3,3,3-tris(4-fluorophenyl)propanoyl}pyrrolidin-2-yl)carbonyl-N-{((3R)-3-piperidyl)methyl}pyrrolidine-2-carboxamide The title compound was prepared by a method similar to Step 2 of Example 99, using 3,3,3-tris(4-fluorophenyl)propionic acid. The compound was obtained as a white solid.
$^1$H-NMR(CDCl$_3$, δppm): 0.85-2.10(12H, m), 2.12-2.23 (1H, m), 2.25-2.40(2H, m), 2.47-2.58(1H, m), 2.80-2.90(1H, m), 2.91-3.00(1H,m), 3.04-3.18(2H, m), 3.30-3.42(1H, m), 3.45(1H, d, J=15.4 Hz), 3.62(1H, dd, J=4.3, 10.9 Hz), 3.72 (1H, d, J=15.4 Hz), 3.77-3.85(1H, m), 4.40-4.50(2H, m), 4.52-4.60(1H, m), 6.96(6H, dd, J$_{HF}$=8.9 Hz, J$_{HH}$=8.9 Hz), 7.09-7.20(1H, m), 7.15(6H, dd, J$_{HF}$=5.3 Hz, J$_{HH}$=8.9 Hz)
ESI-MS(m/e, as $(C_{37}H_{41}F_3N_4O_4+H)^+$): 663

EXAMPLE 101

(2R)-1-{(2S,4R)-4-hydroxy-1-(3,3,3-triphenylpropanoyl)pyrrolidin-2-yl}carbonyl-N-(4-piperidylmethyl)pyrrolidine-2-carboxamide (Step 1)
Synthesis of methyl (2R)-1-{(2S,4R)-4-(tert-butoxy)pyrrolidin-2-yl}carbonylpyrrolidine-2-carboxylate The title compound was prepared by procedures similar to Steps 1-2 of Example 45, using methyl (2R)-pyrrolidine-2-carboxylate and N-α-benzyloxycarbonyl-O-(tert-butyl)-trans-4-hydroxy-L-proline.

(Step 2)
Synthesis of (2R)-1-{(2S,4R)-4-(tert-butoxy)-1-(3,3,3-triphenylpropanoyl)pyrrolidin-2-yl}carbonylpyrrolidine-2-carboxylic acid
The title compound was obtained by successively conducting procedures which were similar to Step 4 of Example 45 and Step 4 of Example 1, using methyl (2R)-1-{(2S,4R)-4-(tert-butoxy)pyrrolidin-2-yl}carbonylpyrrolidine-2-carboxylate.

(Step 3)
Synthesis of (2R)-1-{(2S,4R)-4-hydroxy-1-(3,3,3-triphenylpropanoyl)pyrrolidin-2-yl}carbonyl-N-(4-piperidylmethyl)pyrrolidine-2-carboxamide
The title compound was prepared by successively conducting procedures which were similar to Step 5 of Example 1 and Example 46, using (2R)-1-{(2S,4R)-4-(tert-butoxy)-1-(3,3,3-triphenylpropanoyl)pyrrolidin-2-yl}carbonylpyrrolidine-2-carboxylic acid and 4-aminomethyl-1-(tert-butoxycarbonyl)piperidine. The compound was obtained as a colorless oily substance.
$^1$H-NMR(CDCl$_3$, δppm): 1.18-1.72(6H, m), 1.75-2.09 (5H, m), 2.19-2.30(1H, m), 2.57-2.76(3H, m), 2.86(1H, d, J=10.6 Hz), 3.00-3.12(1H, m), 3.18-3.40(3H, m), 3.52(1H, d, J=14.8 Hz), 3.57(1H, dd, J=4.0, 11.0 Hz), 3.78(1H, d, J=14.8 Hz), 3.79-3.86(2H, m), 4.30-4.40(2H, m), 4.50-4.59(1H, m), 7.13-7.32(15H, m), 7.33-7.41(1H, m)
ESI-MS(m/e, as $(C_{37}H_{44}N_4O_4+H)^+$): 609

EXAMPLE 102

(2R)-1-((2S,4R)-4-hydroxy-1-{3,3,3-tris(4-chlorophenyl)-propanoyl}pyrrolidin-2-yl)carbonyl-N-(4-piperidylmethyl)pyrrolidine-2-carboxamide The title compound was prepared by procedures similar to Steps 2-3 of Example 101, using 3,3,3-tris(4-chlorophenyl) propionic acid. The compound was obtained as a white foamy substance.
$^1$H-NMR(CDCl$_3$, δppm): 0.83-2.08(12H, m), 2.29-2.45 (2H, m), 2.46-2.58(2H, m), 2.98-3.16(4H, m), 3.30-3.38(1H, m), 3.39(1H, d, J=15.0 Hz), 3.6 3(1H, dd, J=4.1, 10.8 Hz), 3.71 (1H, d, J=15.0 Hz), 3.76-3.86(1H, m), 4.38-4.51(2H, m), 4.58(1H, d, J=5.9 Hz), 7.05-7.20(1H, m), 7.12(6H, d, J=8.8 Hz), 7.24(6H, d, J=8.8 Hz)
ESI-MS(m/e, as $(C_{37}H_{41}Cl_3N_4O_4+H)^+$): 711

EXAMPLE 103

(2R)-1-((2S,4R)-4-hydroxy-1-{3.3.3-tris(4-fluorophenyl)-propanoyl}pyrrolidin-2-yl)carbonyl-N-(4-piperidylmethyl)pyrrolidine-2-carboxamide The title compound was prepared by procedures similar to Steps 2-3 of Example 101, using 3,3,3-tris(4-fluorophenyl) propionic acid. The compound was obtained as a white solid.
$^1$H-NMR(CDCl$_3$, δppm): 0.80-2.08(12H, m), 2.28-2.45 (2H, m), 2.46-2.57(2H, m), 2.98-3.12(4H, m), 3.32-3.40(1H, m), 3.44(1H, d, J=15.1 Hz), 3.59(1H, dd, J=4.1, 10.8 Hz), 3.69 (1H, d, J=15.1 Hz), 3.77-3.87(1H, m), 4.40-4.51(2H, m), 4.53-4.61(1H, m), 6.96(6H, dd, J$_{HF}$=8.8 Hz, J$_{HH}$=8.8 Hz), 7.08-7.20(1H, m), 7.15(6H, dd, J$_{HF}$=5.2 Hz, J$_{HH}$=8.8 Hz)
ESI-MS(m/e, as $(C_{37}H_{41}F_3N_4O_4+H)^+$): 663

EXAMPLE 104

(2R)-1-{(2S,4R)-4-hydroxy-1-(3,3,3-triphenylpropanoyl)pyrrolidin-2-yl}carbonyl-N-(4-piperidylethyl)pyrrolidine-2-carboxamide The title compound was prepared by a method similar to Step 3 of Example 101 using 4-aminoethyl-1-(tert-butoxycarbonyl)-piperidine. The compound was obtained as a pale yellow oily substance.

$^1$H-NMR(CDCl$_3$, δppm): 1.02-2.40(15H, m), 2.52-2.64 (2H, m), 2.65-2.78(1H, m), 2.85(1H, d, H=10.8 Hz), 3.02-3.11(2H, m), 3.12-3.24(1H, m), 3.29-3.40(1H, m), 3.45(1H, d, J=14.6 Hz), 3.58(1H, dd, J=4.0, 10.9 Hz), 3.78-3.82(1H, m), 3.83(1H, d, J=14.6 Hz), 4.32-4.40(2H, m), 4.52-4.59(1H, m), 7.12-7.31(16H, m)

ESI-MS(m/e, as (C$_{38}$H$_{46}$N$_4$O$_4$+H)$^+$): 623

EXAMPLE 105

(2R)-1-{(2S,4R)-4-hydroxy-1-(3,3,3-triphenylpropanoyl)pyrrolidin-2-yl}carbonyl-N-{1-methyl-4-piperidyl)ethyl}pyrrolidine-2-carboxamide The title compound was obtained by a method similar to Step 3 of Example 17, using (2R)-1-{(2S,4R)-4-hydroxy-1-(3,3,3-propanoyl)pyrrolidine-2-yl}carbonyl-N-(4-piperidyl-ethyl)pyrrolidine-2-carboxamide and 37% aqueous formaldehyde solution. The compound was obtained as a colorless oily substance.

$^1$H-NMR(CDCl$_3$, δppm): 1.05-2.08(15H, m), 2.28(3H, s), 2.29-2.36(1H, m), 2.70-2.92(4H, m), 3.12-3.28(1H, m), 3.30-3.42(1H, m), 3.43(1H, d, J=14.5 Hz), 3.59 (1H, dd, J=3.8, 10.9 Hz), 3.78-3.83(1H, m), 3.84 (1H, d, J=14.5 Hz), 4.32-4.41(2H, m), 4.53-4.60(1H, m), 7.13-7.33(16H, m)

ESI-MS(m/e, as (C$_{39}$H$_{48}$N$_4$O$_4$+H)$^+$): 637

EXAMPLE 106

(2R)-1-((2S,4R)-4-hydroxy-1-{3,3,3-tris(4-chlorophenyl)-propanoyl}pyrrolidin-2-yl)carbonyl-N-(4-piperidylmethyl)pyrrolidine-2-carboxamide The title compound was prepared by successively conducting procedures similar to Step 2 of Example 101 and Example 104, using 3,3,3-tris(4-chlorophenyl)propionic acid. The compound was obtained as a white foamy substance.

$^1$H-NMR(CDCl$_3$, δppm): 0.95-1.88(10H, m), 1.90-2.00 (2H, m), 2.01-2.12(2H, m), 2.28-2.38(1H, m), 2.46-2.60(3H, m), 2.98-3.11(3H, m), 3.20-3.38(2H, m), 3.40(1H, d, J=15.4 Hz), 3.63(1H, dd, J=4.1, 11.0 Hz), 3.71(1H, d, J=15.4 Hz), 3.73-3.82(1H, m), 4.39-4.52(2H, m), 4.53-4.60(1H, m), 6.98-7.05(1H, m), 7.10(6H, d, J=8.8 Hz), 7.23(6H, d, J=8.8 Hz)

ESI-MS(m/e, as (C$_{38}$H$_{43}$Cl$_3$N$_4$O$_4$+H)$^+$): 725

EXAMPLE 107

(2R)-1-((2S,4R)-4-hydroxy-1-{3,3,3-tris(4-fluorophenyl)-propanoyl}pyrrolidin-2-yl)carbonyl-N-(4-piperidylmethyl)pyrrolidine-2-carboxamide The title compound was prepared by successively conducting procedures similar to Step 2 of Example 101 and Example 104, using 3,3,3-tris(4-fluorophenyl)propionic acid. The compound was obtained as a white solid.

$^1$H-NMR(CDCl$_3$, δppm): 0.85-1.86(10H, m), 1.88-2.00 (2H, m), 2.00-2.10(2H, m), 2.27-2.36(1H, m), 2.47-2.60(3H, m), 2.98-3.06(2H, m), 3.07-3.14(1H, m), 3.15-3.28(1H, m), 3.30-3.41(1H, m), 3.45(1H, d, J=15.5 Hz), 3.60 (1H, dd, J=4.2, 10.6 Hz), 3.70(1H, d, J=15.5 Hz), 3.75-3.85 (1H, m), 4.41-4.52(2H, m), 4.53-4.60(1H, m), 6.94(6H, dd, J$_{HF}$=8.5 Hz, J$_{HH}$=8.5 Hz), 7.00-7.10(1H, m), 7.13 (6H, dd, J$_{HF}$=5.3 Hz, J$_{HH}$=8.5 Hz)

ESI-MS(m/e, as (C$_{38}$H$_{43}$F$_3$N$_4$O$_4$+H)$^+$): 677

EXAMPLE 108

(2R)-1-((2S 4R)-4-hydroxy-1-{3,3,3-tris(4-fluorophenyl)-propanoyl}propanoyl}pyrrolidin-2-yl) carbonyl-N-(1-methyl-4-piperidylmethyl)pyrrolidine-2-carboxamide The title compound was prepared by a method similar to Example 105, using (2R)-1-((2S,4R)-4-hydroxy-1-{3,3,3-tris(4-fluorophenyl)propanyl}pyrrolidin-2-yl)carbonyl-N-(4-piperidylmethyl)pyrrolidine-2-carboxamide. The compound was obtained as a white solid.

$^1$H-NMR(CDCl$_3$, δppm): 1.12-2.20(13H, m), 2.31(3H, s), 2.32-2.39(1H, m), 2.48-2.58(1H, m), 2.83-2.94(2H, m), 2.99-3.10(2H, m), 3.35-3.42(1H, m), 3.45(1H, d, J=15.0 Hz), 3.62 (1H, dd, J=4.1, 11.0 Hz), 3.73(1H, d, J=15.0 Hz), 3.78-3.88 (1H, m), 4.40-4.53(2H, m), 4.59(1H, d, J=5.9 Hz), 6.92-7.03 (6H, m), 7.08-7.25(7H, m)

ESI-MS(m/e, as (C$_{38}$H$_{43}$F$_3$N$_4$O$_4$+H)$^+$): 677

EXAMPLE 109

(2R)-N-{(1-ethyl-4-piperidyl)methvyl}-1-((2S,4R)-4-hydroxy-1-{3,3,3-tris(4-fluorophenyl) propanoyl}pyrrolidin-2-yl)carbonylpyrrolidine-2-carboxamide The title compound was prepared by a method similar to Example 93, using (2R)-1-((2S,4R)-4-hydroxy-1-{3,3,3-tris (4-fluorophenyl)propanoyl}pyrrolidin-2-yl)carbonyl-N-(4-piperidyl-methyl)pyrrolidine-2-carboxamide. The compound was obtained as a white solid.

$^1$H-NMR(CDCl$_3$, δppm): 1.03-2.15(16H, m), 2.29-2.48 (3H, m), 2.50-2.60(1H, m), 2.86-2.96(2H, m), 2.97-3.10(2H, m), 3.30-3.40(1H, m), 3.42(1H, d, J=15.1 Hz), 3.63 (1H, dd, J=3.9, 11.0 Hz), 3.72(1H, d, J=15.1 Hz), 3.78-3.88 (1H, m), 4.40-4.52(2H, m), 4.53-4.61(1H, m), 6.96 (6H, dd, J$_{HF}$=8.8 Hz, J$_{HH}$=8.8 Hz), 7.07-7.20(1H, m), 7.16(6H, dd, J$_{HF}$=5.3 Hz, J$_{HH}$=8.8 Hz)

ESI-MS(m/e, as (C$_{39}$H$_{45}$F$_3$N$_4$O$_4$+H)$^+$): 691

EXAMPLE 110

(2R)-1-((2S,4R)-4-hydroxy-1-{3,3,3-tris(4-fluorophenyl)-propanoyl}pyrrolidin-2-yl)carbonyl-N-{1-(2-propyl)-4-piperidyl-methyl}pyrrolidine-2-carboxamide The title compound was prepared by a method similar to Example 109, using 2-propyl bromide. The compound was obtained as a white solid.

$^1$H-NMR(CDCl$_3$, δppm): 0.82-2.17(13H, m), 1.06 (6H, d, J=6.2 Hz), 2.28-2.37(1H, m), 2.48-2.59(1H, m), 2.66-2.93 (3H, m), 2.96-3.10(2H, m), 3.32-3.41(1H, m), 3.43(1H, d, J=15.0 Hz), 3.63(1H, dd, J=4.3, 10.8 Hz), 3.73 (1H, d, J=15.0 Hz), 3.78-3.88(1H, m), 4.38-4.51(2H, m), 4.57(1H, d, J=6.7 Hz), 6.96(6H, dd, J$_{HF}$=8.8 Hz, J$_{HH}$=8.8 Hz), 7.08-7.20(1H, m), 7.16(6H, dd, J$_{HF}$=5.4 Hz, J$_{HH}$=8.8 Hz)

ESI-MS(m/e, as (C$_{40}$H$_{47}$F$_3$N$_4$O$_4$+H)$^+$): 705

EXAMPLE 111

(2R)-N-{(1-cyclobutylmethyl-4-piperidyl)methyl}-
1-((2S,4R)-4-hydroxy-1-{3,3,3-tris(4-fluorophenyl)
propanoyl}pirrolidin-2-yl)-carbonylpyrrolidine-2-
carboxamide The title compound was prepared by a method similar to Example 109, using (bromomethyl)cyclobutane. The compound was obtained as a white solid.

$^1$H-NMR(CDCl$_3$, δppm): 0.82-2.10(20H,m),2.28-2.44 (2H, m), 2.45-2.60(2H, m), 2.76-2.92(2H, m), 2.97-3.08(2H, m), 3.30-3.40(1H, m), 3.41(1H, d, J=15.1 Hz), 3.57-3.67(1H, m), 3.72(1H, d, J=15.1 Hz), 3.78-3.87(1H, m), 4.39-4.52(2H, m), 4.54-3.61(1H, m), 6.96(6H, dd, J$_{HF}$=8.8 Hz, J$_{HH}$=8.8 Hz), 7.06-7.20(1H, m), 7.15(6H, dd, J$_{HF}$=5.3 Hz, J$_{HH}$=8.8 Hz)

ESI-MS(m/e, as (C$_{42}$H$_{49}$F$_8$N$_4$O$_4$+H)$^+$): 731

EXAMPLE 112

(2R)-N-{(1-cyclopentylmethyl-4-piperidyl)methyl}-
1-((2S,4R)-4-hydroxy-1-{3,3,3-tris(4-fluorophenyl)
propanoyl}pirrolydin-2-yl)-carbonylpyrrolidine-2-
carboxamide To a solution of 19 mg of (2R)-1-((2S,4R)-4-hydroxy-1-{3,3,3-tris(4-fluorophenyl)propanoyl}pyrrolidin-2-yl)carbonyl-N-(4-piperidyl-methyl)pyrrolidine-2-carboxamide in 1.5 ml of acetonitrile, 14 mg of methanesulfonic acid-cyclopentylmethyl, 13 mg of potassium carbonate and 5 mg of potassium iodide were added at room temperature, followed by 24 hours' stirring at 80° C. under heating. The reaction liquid was diluted with chloroform, washed successively with water and 1N aqueous sodium hydroxide solution, and dried over anhydrous sodium sulfate. Distilling the solvent off under reduced pressure, the resultant residue was purified by preparative thin-layer chromatography [Kieselgel™ 60F$_{254}$, Art 5744 (Merck), chloroform/methanol/28% aqueous ammonia=100/10/1) to provide 16 mg of the title compound as a white solid.

$^1$H-NMR(CDCl$_3$, δppm): 1.07-2.50(26H, m), 2.82-2.98 (2H, m), 3.00-3.12(2H, m), 3.32-3.40(1H, m), 3.44 (1H, d, J=15.2 Hz), 3.62(1H, dd, J=4.3, 10.8 Hz), 3.72 (1H, d, J=15.2 Hz), 3.78-3.88(1H, m), 4.40-4.52(2H, m), 4.53-4.61(1H, m), 6.96(6H, dd, J$_{HF}$=8.8 Hz, J$_{HH}$=8.8 Hz), 7.07-7.22(1H, m), 7.15(6H, dd, J$_{HF}$=5.2 Hz, J$_{HH}$=8.8 Hz)

ESI-MS(m/e, as (C$_{43}$H$_{51}$F$_3$N$_4$O$_4$+H)$^+$): 745

EXAMPLE 113

(2R)-N-{(1-cyclopentyl-4-piperidyl)methyl}-1-((2S,
4R)-4-hydroxy-1-{3,3,3-tris(4-fluorophenyl)
propanoyl}pyrrolidin-2-yl)-carbonylpyrrolidine-2-
carboxamide The title compound was prepared by a method similar to Example 109, using bromocyclopentyl. The compound was obtained as a white solid.

$^1$H-NMR(CDCl$_3$, δppm): 1.08-2.20(21H, m), 2.29-2.65 (3H, m), 3.02-3.18(4H, m), 3.30-3.92(3H, m), 3.42 (1H, d, J=15.2 Hz), 3.71(1H, d, J=15.2 Hz), 4.39-4.67(3H, m), 6.90-7.27(13H, m)

ESI-MS(m/e, as (C$_{42}$H$_{49}$F$_3$N$_4$O$_4$+H)$^+$): 731

EXAMPLE 114

(2R)-1-{(2S,4R)-4-hydroxy-1-{3,3,3-triphenylpro-
panoyl)pyrrolidin-2-yl}carbonyl-N-(1-methyl-4-
piperidylmethyl)pyrrolidine-2-carboxamide The title compound was prepared by a method similar to Example 105, using (2R)-1-{(2S,4R)-4-hydroxy-1-(3,3,3-triphenylpropanoyl)pyrrolidine-2-yl}carbonyl-N-(4-piperidylmethyl)pyrrolidine-2-carboxamide. The compound was obtained as a white solid.

$^1$H-NMR(CDCl$_3$, δppm): 1.16-2.08(13H, m), 2.27(3H, s), 2.28-2.36(1H, m), 2.70-2.79(2H, m), 2.80-2.91(2H, m), 2.93-3.04(1H, m), 3.30-3.40(1H, m), 3.43(1H, d, J=14.6 Hz), 3.60 (1H, dd, J=3.8, 1.0 Hz), 3.85(1H, d, J=14.6 Hz), 3.86-4.01 (1H, m), 4.32-4.40(2H, m), 4.58(1H, d, J=6.7 Hz), 7.17-7.36 (16H, m)

ESI-MS(m/e, as (C$_{38}$H$_{46}$N$_4$O$_4$+H)$^+$): 623

EXAMPLE 115

(2R)-N-{(3S)-(1-cyclobutylmethyl-3-piperidyl)me-
thyl}-1-{(2S,4R)-4-hydroxy-1-(3,3,3-triphenylpro-
panoyl)pyrrolidin-2-yl}carbonylpyrrolidine-2-car-
boxamide The title compound was prepared by a method similar to Example 111, using (2R)-1-{(2S,4R)-4-hydroxy-1-(3,3,3-triphenylpropanoyl)pyrrolidin-2-yl}carbonyl-N-((3R)-3-piperidylmethyl)pyrrolidine-2-carboxamide. The compound was obtained as a white solid.

$^1$H-NMR(CDCl$_3$, δppm): 0.65-2.08(19H, m), 2.25-2.33 (1H, m), 2.35(2H, d, J=6.9 Hz), 2.43-2.58(2H, m), 2.60-2.70 (1H, m), 2.71-2.82(2H, m), 3.00-3.11(1H, m), 3.29-3.39(1H, m), 3.40(1H, d, J=14.5 Hz), 3.59(1H, dd, J=3.8, 11.0 Hz), 3.80-3.90(1H, m), 3.87(1H, d, J=14.5 Hz), 4.30-4.38(2H, m), 4.52-4.59(1H, m), 7.14-7.36(16H, m)

ESI-MS(m/e, as (C$_{42}$H$_{52}$N$_4$O$_4$+H)$^+$): 677

EXAMPLE 116

(2R)-N-({(3S)-1-(2,2-dimethylcycylopentylmethyl)-
3-piperidyl}methyl)-1-{(2S,4R)-4-hydroxy-1-(3,3,3-
triphenylpropanoyl)pyrrolidin-2-
yl}carbonylpyrrolidine-2-carboxamide The title compound was prepared by a method similar to Example 95, using 2,2-dimethylcyclopentanecarbaldehyde which was synthesized following K. D. Hutchinson, et al. [Tetrahedron, Vol. 50, 6129-6136 (1994)]. The compound was obtained as a white solid.

$^1$H-NMR(CDCl$_3$, δppm): 0.74(3H, s), 0.80-2.02(20H, m), 1.01(3H, s), 2.07-2.20(1H, m), 2.21-2.36(2H, m), 2.50-2.92 (4H, m), 3.00-3.14(1H, m), 3.30-3.40(1H, m), 3.42 (1H, d, J=14.4 Hz), 3.61(1H, dd, J=2.4, 1.1 Hz), 3.81-3.90 (1H, m), 3.88(1H, d, J=14.4 Hz), 4.30-4.40(2H, m), 4.55-4.61(1H, m), 7.15-7.38(16H, m)

ESI-MS(m/e, as (C$_{45}$H$_{58}$N$_4$O$_4$+H)$^+$): 719

EXAMPLE 117

(2R)-N-{((3S)-1-{2-(1-methylcyclopropyl)ethyl}-3-
piperidyl}methyl}-1-{(2S,4R)-4-hydroxy-1-(3,3,3-
triphenylpropanoyl)pyrrolidin-2-
yl}carbonylpyrrolidine-2-carboxamide The title compound was prepared by a method similar to Examples 95, using 3-cyclopropanebutanal. The compound was obtained as a white solid.

¹H-NMR(CDCl₃, δppm): 0.18-0.30(4H, m), 0.70-2.07 (15H, m), 1.01(3H, s), 2.24-2.34(1H, m), 2.35-2.57(3H, m), 2.68-2.92(3H, m), 3.01-3.13(1H, m), 3.29-3.40(1H, m), 3.41 (1H, d, J=14.5 Hz), 3.60(1H, dd, J=3.8, 11.0 Hz), 3.79-3.87 (1H, m), 3.88(1H, d, J=14.5 Hz), 4.30-4.39(2H, m), 4.56-4.61 (1H, m), 7.15-7.38(16H, m)
ESI-MS(m/e, as $(C_{43}H_{54}N_4O_4+H)^+$): 691

EXAMPLE 118

(2R)-N-({(3S)-1-(1-cyclopentylethyl)-3-piperidyl}methyl)-1-{(2S,4R)-4-hydroxy-1-(3,3,3-triphenylpropanoyl)pyrrolidin-2-yl}carbonylpyrrolidine-2-carboxamide The title compound was prepared by a method similar to Example 112, using 1-(cyclopentyl)ethyl 4-methylbenzenesulfonate. The compound was obtained as a white foamy substance.
¹H-NMR(CDCl₃, δppm): 0.80-2.08(24H, m), 2.15-2.40 (3H, m), 2.50-3.15(5H, m), 3.30-3.53(2H, m), 3.56-3.72 (1H, m), 3.78-3.93(2H, m), 4.26-4.42(2H, m), 4.53-4.62 (1H, m), 7.15-7.43(16H, m)
ESI-MS(m/e, as $(C_{44}H_{56}N_4O_4+H)^+$): 705

EXAMPLE 119

(2R)-N-({(3S)-1-(1-cyclohexylethyl)-3-piperidyl}methyl)-1-{(2S,4R)-4-hydroxy-1-(3,3,3-triphenylpropanoyl)pyrrolidin-2-yl}carbonylpyrrolidine-2-carboxamide The title compound was prepared by a method similar to Step 3 of Example 17, using (2R)-1-{(2S,4R)-4-hydroxy-1-(3,3,3-triphenylpropanoyl)pyrrolidin-2-yl}carbonyl-N-((3R) -3-piperidyl-methyl)pyrrolidine-2-carboxamide and cyclohexyl methyl ketone. The compound was obtained as a white solid.
¹H-NMR(CDCl₃, δppm): 0.80-2.08(27H, m), 2.22-3.15 (7H, m), 3.32-3.46(2H, m), 3.58-3.77(1H, m), 3.84-3.93 (2H, m), 4.28-4.40(2H, m), 4.52-4.60(1H, m), 7.18-7.40 (16H, m)
ESI-MS(m/e, as $(C_{45}H_{58}N_4O_4+H)^+$): 719

EXAMPLE 120

(2R)-N-{((3S)-1-cyclohexyl-3-piperidyl)methyl}-1-{(2S,4R)-4-hydroxy-1-(3,3,3-triphenylpropanoyl)pyrrolidin-2-yl}carbonylpyrrolidine-2-carboxamide The title compound was prepared by a method similar to Example 119, using cyclopentanone. The compound was obtained as a white solid.
¹H-NMR(CDCl₃, δppm): 0.70-2.08(21H, m), 2.26-2.35 (1H, m), 2.39-2.53(2H, m), 2.79-3.03(3H, m), 3.04-3.18 (1H, m), 3.30-3.40(1H, m), 3.42(1H, d, J=14.5 Hz), 3.58 (1H, dd, J=4.0, 10.9 Hz), 3.79-3.90(1H, m), 3.89 (1H, d, J=14.5 Hz), 4.30-4.40(2H, m), 4.54-4.60(1H, m), 7.16-7.38(16H, m)
ESI-MS(m/e, as $(C_{42}H_{52}N_4O_4+H)^+$): 677

EXAMPLE 121

(2R)-N-(4-piperidylmethyl)-1-((2S)-1-{3,3,3-tris(4-fluorophenyl)propanoyl}pyrrolidin-2-yl)carbonylpyrrolidine-2-carboxamide The title compound was prepared by a method similar to Example 64, using 3,3,3-tris(4-fluorophenyl)propionic acid. The compound was obtained as a white foamy substance.
¹H-NMR(CDCl₃, δppm): 0.88-1.10(2H, m), 1.44-1.70 (4H, m), 1.75-2.09(7H, m), 2.30-2.40(1H, m), 2.48-2.60 (3H, m), 2.92-3.13(4H, m), 3.31-3.48(2H, m), 3.42 (1H, d, J=14.8 Hz), 3.76(1H, d, J=14.8 Hz), 3.78-3.84 (1H, m), 4.21(1H, t, J=6.9 Hz), 4.59-4.64(1H, m), 6.97 (6H, dd, $J_{HF}$=8.8 Hz, $J_{HH}$=8.8 Hz), 7.08-7.26(1H, m), 7.18 (6H, dd, $J_{HF}$=5.2 Hz, $J_{HH}$=8.8 Hz)
ESI-MS(m/e, as $(C_{37}H_{41}F_3N_4O_3+H)^+$): 647

EXAMPLE 122

(2R)-N-{(1-methyl-4-piperidyl)methyl}-1-((2S)-1-{3,3,3-tris(4-fluorophenyl)propanoyl}pyrrolidin-2-yl)carbonylpyrrolidine-2-carboxamide The title compound was prepared by a method similar to Example 95, using (2R)-N-(4-piperidylmethyl)-1-((2S)-1-{3,3,3-tris-(4-fluorophenyl)propanoyl}pyrrolidin-2-yl)carbonylpyrrolidine-2-carboxamide. The compound was obtained as a white solid.
¹H-NMR(CDCl₃, δppm): 1.12-1.33(3H, m), 1.35-1.50 (1H, m), 1.52-1.70(3H, m), 1.77-2.08(7H, m), 2.29(3H, s), 2.30-2.39(1H, m), 2.60-2.71(1H, m), 2.80-2.90(2H, m), 2.91-3.10(2H, m), 3.31-3.50(2H, m), 3.41(1H, d, J=14.9 Hz), 3.77 (1H, d, J=14.9 Hz), 3.78-3.85(1H, m), 4.20(1H, t, J=6.9 Hz), 4.58-4.63(1H, m), 6.97(6H, dd, $J_{HF}$=8.9 Hz, $J_{HH}$=8.9 Hz), 7.08-7.23(1H, m), 7.19(6H, dd, $J_{HF}$=5.2 Hz, $J_{HH}$=8.9 Hz)
ESI-MS(m/e, as $(C_{38}H_{43}F_3N_4O_3+H)^+$): 661

EXAMPLE 123

(2R)-N-{(1-ethyl-4-piperidyl)methyl}-1-((2S)-1-{3,3,3-tris-(4-fluorophenyl)propanoyl}pyrrolidin-2-yl)carbonylpyrrolidine-2-carboxamide The title compound was prepared by a method similar to Example 93, using (2R)-N-(4-piperidylmethyl)-1-((2S-1-{3,3,3-tris-(4-fluorophenyl)propanoyl}pyrrolidin-2-yl)carbonylpyrrolidine-2-carboxamide. The compound was obtained as a white foamy substance.
¹H-NMR(CDCl₃, δppm): 1.09(3H, t, J=7.1 Hz), 1.15-1.33 (3H, m), 1.34-1.50(1H, m), 1.52-1.68(3H, m), 1.74-2.08 (7H, m), 2.29-2.35(1H, m), 2.40(2H, q, J=7.1 Hz), 2.60-2.70 (1H, m), 2.87-2.98(3H, m), 2.99-3.10(1H, m), 3.30-3.50(2H, m), 3.39(1H, d, J=14.8 Hz), 3.76(1H, d, J=14.8 Hz), 3.77-3.83 (1H, m), 4.19(1H, t, J=6.9 Hz), 4.58-4.62(1H, m), 6.95 (6H, dd, $J_{HF}$=8.8 Hz, $J_{HH}$=8.8 Hz), 7.06-7.12(1H, m), 7.17 (6H, dd, $J_{HF}$=5.3 Hz, $J_{HH}$=8.8 Hz)
ESI-MS(m/e, as $(C_{39}H_{46}F_3N_4O_3+H)^+$): 675

EXAMPLE 124

(2R)-N-{(1-1)propyl-4-piperidyl)methyl}-((2S)-1-{3,3,3-tris-(4-fluorophenyl)propanoyl}pyrrolidin-2-yl)carbonylpyrrolidine-2-carboxamide The title compound was prepared by a method similar to Example 122, using propionaldehyde. The product was obtained as a white foamy substance.
¹H-NMR(CDCl₃, δppm): 0.90(3H, t, J=7.3 Hz), 1.03-2.10 (16H, m), 2.22-2.38(3H, m), 2.59-2.70(1H, m), 2.85-2.99 (3H, m), 3.00-3.10(1H, m), 3.30-3.50(2H, m), 3.40(1H, d, J=14.9 Hz), 3.77(1H, d, J=14.9 Hz), 3.78-3.84 (1H, m), 4.20 (1H, t, J=6.9 Hz), 4.57-4.62(1H, m), 6.95 (6H, dd, $J_{HF}$=8.9 Hz, $J_{HH}$=8.9 Hz), 7.06-7.15(1H, m), 7.18 (6H, dd, $J_{HF}$=5.2 Hz, $J_{HH}$=8.9 Hz)
ESI-MS(m/e, as $(C_{40}H_{47}F_3N_4O_3+H)^+$): 689

EXAMPLE 125

(2R)-N-{(1-cyclopronylmethyl-4-piperidyl)methyl}-1-((2S)-1-{3,3,3-tris(4-fluorophenyl)propanoyl}pyrrolidin-2-yl)carbonylpyrrolidine-2-carboxamide The title compound was prepared by a method similar to Example 122, using cyclopropanecarbaldehyde. The product was obtained as a white foamy substance.

$^1$H-NMR)CDCl$_3$, δppm): 0.08-0.14(2H, m), 0.48-0.56 (2H, m), 0.83-2.10(15H, m), 2.20-2.28(2H, m), 2.30-2.39 (1H, m), 2.62-2.72(1H, m), 2.89-2.97(1H, m), 2.99-3.11(3H, m), 3.30-3.50(2H, m), 3.41(1H, d, J=14.9 Hz), 3.77(1H, d, J=14.9 Hz), 3.78-3.86(1H, m), 4.20(1H, t, J=6.9 Hz), 4.58-4.63(1H, m), 6.96(6H, dd, J$_{HF}$=8.8 Hz, J$_{HH}$=8.8 Hz),. 7.03-7.12(1H, m), 7.18(6H, dd, J$_{HF}$=5.3 Hz, J$_{HH}$=8.8 Hz)

ESI-MS(m/e, as (C$_{41}$H$_{47}$F$_3$N$_4$O$_3$+H)$^+$): 701

EXAMPLE 126

N-{3-((3S)-3-piperidylmethyl)amino-3-oxopropyl}-1-(3,3,3-triphenylpropanoyl)-2-pyrrolidinecarboxamide The title compound was obtained by successively conducting procedures similar to Steps 1-5 of Example 1 and Step 2 of Example 17, using tert-butoxycarbonyl-L-proline. The compound was obtained as a white foamy substance.

$^1$H-NMR(CDCl$_3$, δppm): 0.95-1.98(11H, m), 2.06-2.12 (1H, m), 2.18-2.28(2H, m), 2.44-2.56(1H, m), 2.83-3.10 (4H, m), 3.18-3.32(1H, m), 3.33-3.54(2H, m), 3.63 (1H, d, J=15.3 Hz), 3.77(1H, d, J=15.3 Hz), 4.12-4.20(1H, m), 6.32-6.41 (1H, m), 6.63-6.71(1H, m), 7.12-7.30(15H, m)

ESI-MS(m/e, as (C$_{35}$H$_{42}$N$_4$O$_3$+H)$^+$): 567

EXAMPLE 127

N-{3-({(3R)-1-(cyclohexylmethyl)-3-piperidyl}methylamino)-3-oxopropyl}-1-(3,3,3-triphenylpropanoyl)-2-pyrrolidinecarboxamide The title compound was prepared by a method similar to Example 12, using N-{(3-((3S)-3-piperidylmethyl)amino-3-oxopropyl}-1-(3,3,3-triphenylpropanoyl)-2-pyrrolidinecarboxamide. The compound was obtained as a white foamy substance.

$^1$H-NMR)CDCl$_3$, δppm): 0.78-2.22(27H, m), 2.62-3.18 (4H, m), 3.20-3.58(3H, m), 3.64(1H, d, J=15.2 Hz), 3.77 (1H, d, J=15.2 Hz), 4.13-4.20(1H, m), 6.28-6.40(1H, m), 6.60-6.70(1H, m), 7.16-7.32(15H, m)

ESI-MS(m/e, as (C$_{42}$H$_{54}$N$_4$O$_3$+H)$^+$): 663

EXAMPLE 128

(3S)-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-1,1-dimethylpiperidinium bromide To 15 mg of (2R)-1-{(2S,4R)-4-hydroxy-1-(3,3,3-triphenylpropanoyl)pyrrolidin-2-yl}carbonyl-N-{((3S)-1-methyl-3-piperidyl)methyl}pyrrolidine-2-carboxamide, 0.5 ml of 10% methyl bromide-acetonitrile was added at room temperature, followed by 12 hours' stirring. The solvent in the reaction liquid was distilled off under reduced pressure, and the resulting residue was purified by preparative thin-layer chromatography (aluminium oxide 60F$_{254}$, Art. 5713 (Merck), choroform/methanol=18/1) to provide 15 mg of the title compound as a white solid.

$^1$H-NMR(CDCl$_3$, δppm): 0.86-2.30(12H, m),2.62-3.80 (17H, m), 3.87-3.98(1H, m), 4.36-4.48(1H, m), 4.49-4.62 (2H, m), 7.10-7.36(15H, m), 7.42-7.54(1H, m)

ESI-MS(m/e, as (C$_{39}$H$_{49}$N$_4$O$_4$)$^+$): 637

EXAMPLE 129

(3S)-1,1-diethyl-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)piperidinium chloride To 22 mg of (2R)-N-{((3S)-1-ethyl-3-piperidyl)methyl}-1-{(2S,4R)-4-hydroxy-1-(3,3,3-triphenylpropanoyl)pyrrolidin-2-yl}-carbonylpyrrolidine-2-carboxamide, 1 ml of ethyl iodide was added at room temperature, followed by 2 hours' stirring at 70° C. The resultant reaction liquid was diluted with chloroform and the solvent was distilled off under reduced pressure. The resultant residue was dissolved in ultrapure water 0.6 ml/methanol 0.1 ml and the solution was developed on reversed phase medium-pressure liquid chromatography [ODS-AQ 120-S50 (YMC)]. Purification and anion exchange were conducted by pouring 20 ml of saturated brine, washing with 150 ml of ultrapure water and eluting the title compound with methanol/water=1/1, to provide 21 mg of the title compound as a white solid.

$^1$H-NMR)CDCl$_3$, δppm): 0.82-2.30(18H, m), 2.50-3.88 (16H, m), 4.37-4.52(3H, m), 7.13-7.36(15H, m), 7.57-7.64 (1H, m)

ESI-MS(m/e, as (C$_{41}$H$_{53}$N$_4$O$_4$)$^+$): 665

EXAMPLE 130

(3S)-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-1,1-dipropylpiperidinium iodide To 4.9 mg of (2R)-1-{(2S,4R)-4-hydroxy-1-(3,3,3-triphenylpropanoyl)pyrrolidin-2-yl}carbonyl-N-{((3S)-1-propyl-3-piperidyl)methyl}pyrrolidine-2-carboxamide, 1 ml of propyl iodide was added at room temperature, followed by 15 hours' stirring at 100° C. under heating. The reaction liquid was diluted with chloroform, the solvent was distilled off under reduced pressure, and the resulting residue was purified with preparative thin-layer chromatography (aluminium oxide 60F$_{254}$, Art 5713 (Merck), chloroforom/methanol=18/1) to provide 4.1 mg of the title compound as a pale yellow solid.

$^1$H-NMR(CDCl$_3$, δppm): 0.84-0.92(1H, m), 1.01 (3H, t, J=7.1 Hz), 1.06(3H, t, J=7.1 Hz), 1.16-1.37(3H, m), 1.52-2.12(11H, m), 2.18-2.39(2H, m), 2.77-2.93(3H, m), 3.08-3.33(3H,m), 3.35-3.73(6H, m), 3.50(1H, d, J=14.8 Hz), 3.82-3.90(1H, m), 3.94(1H, d, J=14.8 Hz), 4.31-4.40(2H, m), 4.45-4.60(1H, m), 7.15-7.40(15H, m), 7.58-7.66(1H, m)

ESI-MS(m/e, as (C$_{43}$H$_{57}$N$_4$O$_4$)$^+$): 693

EXAMPLE 131

(3S)-1,1-dicyclopropylmethyl-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)piperidinium bromide The title compound was prepared by a method similar to Example 130, using (2R)-N-{((3S)-1-cyclopropylmethyl-3- piperidyl)methyl}-1-{(2S,4R)-4-hydroxy-1-(3,3,3-triphenylpropanoyl)pyrrolidin-2-yl}carbonylpyrrolidine-2-carboxamide and cyclopropylmethyl bromide. The compound was obtained as a white solid.

$^1$H-NMR)CDCl$_3$, δppm): 0.68-1.77(18H, m), 1.80-2.20 (4H, m), 2.22-2.36(1H, m), 2.64-2.78(1H, m), 2.90-3.10(2H, m), 3.30-3.70(8H, m), 3.52(1H, d, J=14.8 Hz), 3.72-4.01(2H, m), 3.88(1H, d, J=14.8 Hz), 4.36-4.60(3H, m), 7.16-7.43 (15H, m), 7.49-7.70(1H, m)

ESI-MS(m/e, as (C$_{45}$H$_{57}$N$_4$O$_4$)$^+$): 717

EXAMPLE 132

(3R)-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-1,1-dimethylpiperidinium bromide The title compound was prepared by a method similar to Example 128, using (2R)-1-{(2S,4R)-4-hydroxy-1-(3,3,3-triphenylpropanoyl)pyrrolidin-2-yl}carbonyl-N-{((3R)-1-methyl-3-piperidyl)methyl}pyrrolidine-2-carboxamide. The compound was obtained as a white solid.

$^1$H-NMR)CDCl$_3$, δppm): 0.83-2.07(9H, m), 2.12-2.34 (3H, m), 2.48-2.70(2H, m), 2.86-3.01(2H, m), 3.10-3.47(8H, m), 3.50-3.80(2H, m), 3.55(1H, d, J=14.8 Hz), 3.71(1H, d, J=14.8 Hz), 3.96-4.12(2H, m), 4.30-4.40(1H, m), 4.55-4.62 (1H, m), 4.67-4.76(1H, m), 7.10-7.38(15H, m), 7.58-7.68 (1H, m)

FAB-MS(m/e, as (C$_{39}$H$_{49}$N$_4$O$_4$)$^+$): 637

EXAMPLE 133

(3R)-1,1-diethyl-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)piperidinium chloride The title compound was prepared by a method similar to Example 129, using (2R)-N-{((3R)-1-ethyl-3-piperidyl)methyl}-1-{(2S,4R)-4-hydroxy-1-(3,3,3-triphenylpropanoyl)pyrrolidin-2-yl}carbonylpyrrolidine-2-carboxamide. The compound was obtained as a white solid.

$^1$H-NMR)CDCl$_3$, δppm): 0.89-1.46(10H, m), 1.68-2.10 (6H, m), 2.20-2.30(2H, m), 2.34-2.50(2H, m), 3.05-3.90 (12H, m), 3.60(1H, d, J=15.7 Hz), 3.71(1H, d, J=15.7 Hz), 4.37-4.45(1H, m), 4.52-4.67(2H, m), 7.13-7.40(15H, m), 7.58-7.69(1H, m)

FAB-MS(m/e, as (C$_{41}$H$_{53}$N$_4$O$_4$)$^+$): 665

EXAMPLE 134

(3R)-1,1-diallyl-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)piperidinium bromide The title compound was prepared by a method similar to Example 128, using (2R)-N-{((3R)-1-allyl-3-piperidyl)methyl}-1-{(2S,4R)-4-hydroxy-1-(3,3,3-triphenylpropanoyl)pyrrolidin-2-yl}carbonyl-pyrrolidine-2-carboxamide and allyl bromide. The compound was obtained as a white foamy substance.

$^1$H-NMR)CDCl$_3$, δppm): 0.80-2.28(13H, m), 2.52-2.65 (1H, m), 2.66-2.78(1H, m), 2.78-2.96(1H, m), 3.00-3.12 (1H, m), 3.20-3.49(4H, m), 3.50(1H, d, J=14.3 Hz), 3.72 (1H, d, J=14.3 Hz), 3.76-3.86(1H, m), 3.88-4.07(3H, m), 4.18-4.30 (1H, m), 4.30-4.42(2H, m), 4.50-4.60(2H, m), 5.70-5.78(2H, m), 5.79-5.88(1H, m), 5.90-6.10(2H, m), 7.16-7.38(15H, m), 7.62-7.70(1H, m)

FAB-MS(m/e, as (C$_{43}$H$_{53}$N$_4$O$_4$)$^+$): 689

EXAMPLE 135

(3R)-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-1,1-dipropylpiperidinium chloride The title compound was prepared by a method similar to Example 129, using (2R)-1-{(2S,4R)-4-hydroxy-1-(3,3,3-triphenylpropanoyl)pyrrolidin-2-yl}carbonyl-N-{((3R)-1-propyl-3-piperidyl)methyl}pyrrolidine-2-carboxamide and propyl iodide. The compound was obtained as a pale yellow solid.

$^1$H-NMR(CDCl$_3$, δppm): 0.80-2.10(19H, m), 2.15-2.32 (2H, m), 2.48-2.60(2H, m), 2.90-3.00(2H, m), 3.01-3.59(9H, m), 3.53(1H, d, J=14.6 Hz), 3.63-3.80(1H, m), 3.75 (1H, d, J=14.6 Hz), 3.88-3.98(1H, m), 4.30-4.38(1H, m), 4.55-4.70 (2H, m), 7.15-7.43(15H, m), 7.67-7.77(1H, m)

ESI-MS(m/e, as (C$_{43}$H$_{57}$N$_4$O$_4$)$^+$): 693

EXAMPLE 136

(3R)-1-butyl-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-1-methylpiperidinium bromide The title compound was prepared by a method similar to Example 128, using (2R)-N-{((3R)-1-butyl-3-piperidyl)methyl}-1-{(2S,4R)-4-hydroxy-1-(3,3,3-triphenylpropanoyl) pyrrolidin-2-yl}-carbonylpyrrolidine-2-carboxamide and (bromomethyl)cyclopropane. The compound was obtained as a white foamy substance.

$^1$H-NMR)CDCl$_3$, δppm): 0.82-2.17(15H, m), 2.18-2.39 (3H, m), 2.72-2.84(2H, m), 2.85-3.12(3H, m), 3.13-3.78 (9H, m), 3.52(1H, d, J=14.4 Hz), 3.71(1H, d, J=14.4 Hz), 3.83-4.06(2H, m), 4.32-4.40(1H, m), 4.49-4.82(2H, m), 7.16-7.40 (15H, m), 7.56-7.75(1H, m)

FAB-MS(m/e, as (C$_{42}$H$_{55}$N$_4$O$_4$)$^+$): 679

EXAMPLE 137

(3R)-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-1-methyl-1-(2-methylbutyl)piperidinium bromide The title compound was prepared by a method similar to Example 128, using (2R)-1-{(2S,4R)-4-hydroxy-1-(3,3,3-triphenylpropanoyl)pyrrolidin-2-yl}carbonyl-N-{((3R)-1-(2-methylbutyl)-3-piperidyl)methyl}pyrrolidine-2-carboxamide. The compound was obtained as a white solid.

$^1$H-NMR(CDCl$_3$, δppm): 0.70-2.20(18H, m), 2.22-2.50 (2H, m), 2.78-3.05(4H, m), 3.06-3.80(10H, m), 3.53 (1H, d, J=14.1 Hz), 3.69(1H, d, J=14.1 Hz), 3.83-3.95(1H, m), 4.08-4.23(1H, m), 4.32-4.80(3H, m), 7.10-7.47(15H, m), 7.48-7.80(1H, m)

FAB-MS(m/e, as (C$_{43}$H$_{57}$N$_4$O$_4$)$^+$): 693

EXAMPLE 138

(1R*,3R)- and (1S*,3R)-3-({({(2R)-1-({(2S,4R)-4-hydroxvy-1-(3,3,3-triphenylpropanoyl)-2-pyrrolidinyl}carbonyl)-2-pyrrolidinyl}-carbonyl)amino}methyl)-1-methyl-1-pentylpiperidinium bromide After conducting a procedure similar to Example 128, using (2R)-1-{(2S,4R)-4-hydroxy-1-(3,3,3-triphenylpropanoyl)pyrrolidin-2-yl}carbonyl-N-{((3R)-1-pentyl-3-piperidyl)methyl}pyrrolidine-2-carboxamide, the resulting diastereomer was separated, to provide the title compound which was expediently named (1R*)-form as a low-polarity substance in the form of a white solid, and the title compound expediently named (1S*)-form, as a high-polarity substance in the form of a white solid.

(1R*)-form
$^1$H-NMR(CDCl$_3$, δppm): 0.86-1.21(4H, m), 1.28-1.47(4H, m), 1.50-2.17(13H, m), 2.20-2.37(2H, m), 2.68-2.78(1H, m), 2.88-3.03(2H, m), 3.04-3.20(1H, m), 3.25(3H, s), 3.34-3.68 (4H, m), 3.51(1H, d, J=14.1 Hz), 3.73(1H, d, J=14.1 Hz), 3.98-4.08(2H, m), 4.28-4.40(1H, m), 4.50-4.61 (2H, m), 7.18-7.40(15H, m), 7.58-7.65(1H, m)
FAB-MS(m/e, as (C$_{43}$H$_{57}$N$_4$O$_4$)$^+$): 693

(1S*)-form
$^1$H-NMR(CDCl$_3$, δppm): 0.88-1.08(4H, m), 1.28-1.42(4H, m), 1.43-2.02(10H, m), 2.08-2.37(4H, m), 2.97-3.10(2H, m), 3.15(3H, s), 3.16-3.63(7H, m), 3.58(1H, d, J=15.5 Hz), 3.71 (1H, d, J=15.5 Hz), 3.84-3.92(1H, m), 3.92-4.03 (1H, m), 4.38-4.42(1H, m), 4.58-4.63(1H, m), 4.76(1H, t, J=8.3 Hz), 7.15-7.39(15H, m), 7.66-7.73(1H, m)
FAB-MS(m/e, as (C$_{43}$H$_{57}$N$_4$O$_4$)$^+$): 693

EXAMPLE 139

(1R*,3R)- and (1S*,3R)-3-({({(2R)-1-({(2S,4R)-4-hydroxy-1-(3,3,3-triphenylpropanoyl)-2-pyrrolidinyl}carbonyl)-2-pyrrolidinyl}-carbonyl)amino}methyl)-1-methyl-1-octylpiperidinium bromide After conducting a procedure similar to Example 128, using (2R)l-1-{(2S,4R)-4-hydroxy-1-(3,3,3-triphenylpropanoyl)pyrrolidin-2-yl}-carbonyl-N-{((3R)-1-octyl-3-piperidyl)methyl}pyrrolidine-2-carboxamide, the resulting diastereomer was separated, to provide the title compound which was expediently named (1R*)-form as a low-polarity substance in the form of a white foamy substance, and the title compound expediently named (1S*)-form, as a high-polarity substance in the form of a white solid.

(1R*)-form
$^1$H-NMR(CDCl$_3$, δppm): 0.87(3H, t, J=6.7 Hz), 0.98-2.38 (26H, m), 2.73-2.98(3H, m), 3.02-3.14(1H, m), 3.22(3H, s), 3.37-3.62(4H, m), 3.52(1H, d, J=14.2 Hz), 3.72 (1H, d, J=14.2 Hz), 3.93-4.08(2H, m), 4.30-4.38(1H, m), 4.50-4.60 (2H, m), 7.18-7.40(15H, m), 7.58-7.65(1H, m)
FAB-MS(m/e, as (C$_{46}$H$_{63}$N$_4$O$_4$)$^+$): 735

(1S*)-form
$^1$H-NMR(CDCl$_3$, δppm): 0.87(3H, t, J=6.7 Hz), 0.92-1.10 (1H, m), 1.18-2.05(21H, m), 2.10-2.40(4H, m), 2.75-3.60 (8H, m), 3.15(3H, s), 3.58(1H, d, J=15.4 Hz), 3.72 (1H, d, J=15.4 Hz), 3.79-3.90(11H, m), 3.93-4.06(1H, m), 4.34-4.45 (1H, m), 4.49-4.82(2H, m), 7.15-7.38(15H, m), 7.56-7.75 (1H, m)
FAB-MS(m/e, as (C$_{46}$H$_{63}$N$_4$O$_4$)$^+$): 735

EXAMPLE 140

(3R)-1,1-dicyclopropylmethyl-3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)piperidinium bromide The title compound was prepared by a method similar to Example 131, using (2R)-N-{((3R)-1-cyclopropylmethyl-3-piperidyl)methyl}-1-{(2S,4R)-4-hydroxy-1-(3,3,3-triphenylpropanoyl)pyrrolidin-2-yl}carbonyl pyrrolidine-2-carboxamide. The compound was obtained as a white foamy substance.

$^1$H-NMR(CDCl$_3$, δppm): 0.54-0.70(3H, m), 0.73-0.85 (2H, m), 0.88(4H, t, J=6.6 Hz), 1.00-2.25(13H, m), 2.47-2.60 (1H, m), 2.70-2.84(2H, m), 2.92-3.10(2H, m), 3.38-3.75(8H, m), 3.78-3.98(3H, m), 4.20-4.40(1H, m), 4.40-4.50(1H, m), 4.52-4.58(1H, m), 7.16-7.42(15H, m), 7.83-7.91(1H, m)
FAB-MS(m/e, as (C$_{45}$H$_{57}$N$_4$O$_4$)$^+$): 717

EXAMPLE 141

(1R*,3R)- and (1S*,3R)-1-cyclohexylmethyl-3-({({(2R)-1-({(2S,4R)-4-hydroxy-1-(3,3,3-triphenylpropanoyl)-2-pyrrolidinyl}carbonyl)-2-pyrrolidinyl}-carbonyl)amino}methyl-1-methylpiperidinium bromide After conducting a procedure similar to Example 128 using (2R)-N-{((3R)-1-cyclohexylmethyl-3-piperidyl)methyl}-1-{(2S,4R)-4-hydroxy-1-(3,3,3-triphenylpropanoyl)pyrrolidin-2-yl}carbonylpyrrolidine-2-carboxamide, the resulting diastereomer was separated, to provide the title compound which was expediently named (1R*)-form as a low polarity substance in the form of a white solid, and the title compound expediently named (1S*)-form, as a high-polarity substance in the form of a white solid.

(1R*)-form
$^1$H-NMR(CDCl$_3$, δppm): 1.02-2.23(21H, m), 2.30-2.40 (1H, m), 2.67-2.78(1H, m), 2.83-3.02(3H, m), 3.20-3.37 (5H, m), 3.38-3.65(5H, m), 3.56(1H, d, J=14.4 Hz), 3.70 (1H, d, J=14.4 Hz), 3.84-4.02(1H, m), 4.10-4.19(1H, m), 4.30-4.38 (1H, m), 4.40-4.49(2H, m), 7.15-7.40(15H, m), 7.50-7.60 (1H, m)
FAB-MS(m/e, as (C$_{45}$H$_{59}$N$_4$O$_4$)$^+$): 719

(1S*)-form
$^1$H-NMR(CDCl$_3$, δppm): 0.80-2.07(18H, m), 2.18-2.38 (4H, m), 2.72-3.36(10H, m), 3.38-3.50(4H, m), 3.56 (1H, d, J=14.9 Hz), 3.73(1H, d, J=14.9 Hz), 3.76-3.85(1H, m), 4.02-4.12(1H, m), 4.33-4.40(1H, m), 4.60(1H, d, J=6.6 Hz), 4.77 (1H, t, J=8.1 Hz), 7.12-7.40(15H, m), 7.77(1H, t, J=5.7 Hz)
FAB-MS(m/e, as (C$_{45}$H$_{59}$N$_4$O$_4$)$^+$): 719

EXAMPLE 142

(3R)-1-cycloheptylmethyl-3-({({(2R)-1-({(2S,4R)-4-hydroxy-1-(3,3,3-triphenylpropanoyl)-2-pyrrolidinyl}carbonyl)-2-pyrrolidinyl}-carbonyl)amino}methyl)-1-methylpiperidinium bromide The title compound was prepared by a method similar to Example 128, using (2R)-N-{((3R)-1-cycloheptylmethyl-3-piperidyl)methyl}-1-{(2S,4R)-4-hydroxy-1-(3,3,3-triphenylpropanoyl)pyrrolidin-2-yl}carbonylpyrrolidine-2-carboxamide. The compound was obtained as a white solid.

$^1$H-NMR(CDCl$_3$, δppm): 0.83-1.35(6H, m), 1.36-2.02 (14H, m), 2.03-2.21(3H, m), 2.22-2.64(2H, m), 2.80-3.00 (4H, m), 3.08-3.30(5H, m), 3.31-3.74(4H, m), 3.54 (1H, d, J=14.5 Hz), 3.68(1H, d, J=14.5 Hz), 3.82-3.95(1H, m), 4.09-4.18(1H, m), 4.33-4.78(3H, m), 7.10-7.39(15H, m), 7.47-7.72(1H, m)

FAB-MS(m/e, as (C$_{46}$H$_{61}$N$_4$O$_4$)$^+$): 733

EXAMPLE 143

(3R)-1,1-diethyl-3-({({(2R)-1-({(2S,3R,4S)-3,4-dihydroxy-1-(3,3,3-triphenylpropanoyl)-2-pyrrolidinyl}carbonyl)-2-pyrrolidinyl}-carbonyl)amino}methyl)piperidinium chloride The title compound was prepared by a method similar to Example 129, using (2R)-N-{((3R)-1-ethyl-3-piperidyl)methyl}-1-{(2S,3R,4S)-3,4-dihydroxy-1-(3,3,3-triphenylpropanoyl)pyrrolidin-2-yl}carbonylpyrrolidine-2-carboxamide. The compound was obtained as a white solid.

$^1$H-NMR(CDCl$_3$, δppm): 0.85-2.40(16H, m), 2.92-3.78 (16H, m), 4.18-4.35(3H, m), 4.43-4.58(2H, m), 7.10-7.35 (15H, m), 7.48-7.65(1H, m)

FAB-MS(m/e, as (C$_{41}$H$_{53}$N$_4$O$_5$)$^+$): 681

EXAMPLE 144

(3R)-1,1-diethyl-3-({({(2R)-1-({(2S,4R)-4-hydroxy-1-{3,3,3-tris-(4-chlorophenyl)propanoyl}-2-pyrrolidinyl}carbonyl)-2-pyrrolidinyl}-carbonyl)amino}methyl)piperidinium chloride The title compound was prepared by a method similar to Example 129, using (2R)-N-{((3R)-1-ethyl-3-piperidyl)methyl}-1-((2S,4R)-4-hydroxy-1-{3,3,3-tris(4-chlorophenyl)propanoyl}pyrrolidin-2-yl)carbonylpyrrolidine-2-carboxamide. The compound was obtained as a white solid.

$^1$H-NMR(CDCl$_3$, δppm): 1.26(6H, t, J=7.1 Hz), 1.32-2.19 (11H, m), 2.20-2.35(2H, m), 2.38-2.49(1H, m), 3.17-3.85 (12H, m), 3.92-4.03(1H, m), 4.16-4.30(1H, m), 4.39-4.44 (1H, m), 4.56-4.60(1H, m), 4.72-4.81(1H, m), 7.06-7.18(6H, m), 7.20-7.30(6H, m), 7.60-7.67(1H, m)

ESI-MS(m/e, as (C$_{41}$H$_{50}$Cl$_3$N$_4$O$_4$)$^+$): 767

EXAMPLE 145

(3R)-1,1-diethyl-3-({({(2R)-1-({(2S,4R)-4-hydroxy-1-{3,3,3-tris-(4-ethylphenyl)propanoyl}-2-pyrrolidinyl}carbonyl)-2-pyrrolidinyl}-carbonyl)amino}methyl)piperidinium chloride The title compound was prepared by a method similar to Example 129, using (2R)-N-{((3R)-1-ethyl-3-piperidyl)methyl}-1-((2S,4R)-4-hydroxy-1-{3,3,3-tris(4-ethylphenyl)propanoyl}pyrrolidin-2-yl)carbonylpyrrolidine-2-carboxamide. The compound was obtained as a white solid.

$^1$H-NMR)CDCl$_3$, δppm): 0.82-1.20(3H, m), 1.22 (9H, t, J=7.5 Hz), 1.30-2.55(17H, m), 2.61(6H, q, J=7.5 Hz), 2.74-4.30(14H, m), 4.32-4.46(1H, m), 4.47-4.56(2H, m), 7.01-7.22(12H, m), 7.50-7.75(1H, m)

ESI-MS(m/e, as (C$_{47}$H$_{65}$N$_4$O$_4$)$^+$): 749

EXAMPLE 146

(3R)-1-heptyl-1-methyl-3-({(3-{(2-{(3,3,3-triphenylpropanoyl)amino}acetyl)amino}propanoyl)amino}methyl)piperidinium bromide The title compound was prepared by a method similar to Example 128, using N-{2-(3-{((3R)-1-heptyl-3-piperidyl)methyl}amino-3-oxopropyl)amino-2-oxoethyl}-3,3,3-triphenylpropanamide. The compound was obtained as a white solid.

$^1$H-NMR)CDCl$_3$, δppm): 0.80-2.60(20H, m), 2.82-3.82 (17H, m), 6.62-6.88(1H,m), 7.09-7.40(16H, m), 7.85-7.99 (1H, m)

FAB-MS(m/e, as (C$_{40}$H$_{55}$N$_4$O$_3$)$^+$): 639

EXAMPLE 147

(3R)-1-heptyl-1-methyl-3-({(3-{(2-{(3,3,3-triphenylpropanoyl)-(methyl)amino}acetyl)amino}propanoyl)amino}methyl)piperidinium bromide The title compound was prepared by a method similar to Example 128, using N-{2-(3-{((3R)-1-heptyl-3-piperidyl)methy}amino-3-oxopropyl)amino-2-oxoethyl}-N-methyl-3,3,3-triphenylpropanamide. The compound was obtained as a white solid.

$^1$H-NMR)CDCl$_3$, δppm): 0.80-2.32(20H, m), 2.45-4.05 (20H, m), 6.88-8.13(17H, m)

FAB-MS(m/e, as (C$_{41}$H$_{57}$N$_4$O$_3$)$^+$): 653

EXAMPLE 148

1-Cyclooctylmethyl-1-ethyl-3-({(6-{(3,3,3-triphenylpropanoyl)amino}hexanoyl)amino}methyl)piperidinium iodide The title compound was prepared by a method similar to Example 130, using N-(6-{(1-cyclobutylmethyl-3-piperidyl)methyl}-amino-6-oxohexyl)-3,3,3-triphenylpropanamide and ethyl iodide. The compound was obtained as a pale yellow solid. $^1$H-NMR(CDCl$_3$, δppm): 1.00-2.27(31H, m), 2.78-2.97 (3H, m), 3.02-3.54(9H, m), 3.60(2H, s), 7.12-7.30 (15H, m)

FAB-MS(m/e, as (C$_{44}$H$_{62}$N$_3$O$_2$)$^+$): 664

EXAMPLE 149

(3S)-1-ethyl-1-{(2S)-2-methylbutyl}-3-({(6-{(3,3,3-triphenylpropanoyl)amino}hexanoyl)amino}methyl)piperidinium iodide (Step 1)
Synthesis of N-{6-({(3S)-1-{(2S)-2-methylbutyl}-3-piperidyl}methyl)amino-6-oxohexyl}-3,3,3-triphenylpropanamide The title compound was prepared by a method similar to Example 77, using (3S)-3-aminomethyl-1-(t-butoxycarbonyl)-piperidine and (2S)-2-methylbutane iodide. The compound was obtained as a white solid.

$^1$H-NMR(CDCl$_3$, δppm): 0.86-0.92(6H, m), 0.98-1.18 (6H, m), 1.37-1.73(7H, m), 1.82-2.00(2H, m), 2.18 (2H, t, J=7.4 Hz), 2.20-2.28(3H, m), 2.68-2.80(2H, m), 2.91 (2H, dd, J=6.0, 12.5 Hz), 3.09-3.28(2H, m), 3.56(2H, s), 4.80-4.88 (1H, m), 5.78-5.88(1H, m), 7.17-7.32(15H, m)

FAB-MS(m/e, as (C$_{38}$H$_{51}$N$_3$O$_2$+H)$^+$): 582

(Step 2)
Synthesis of (3S)-1-ethyl-1-{(2S)-2-methylbutyl}-3-({(6-{(3,3,3-triphenylpropanoyl)amino}hexanoyl)amino}methyl)-piperidinium iodide The title compound was prepared by a method similar to Example 148, using N-{6-({(3S)-1-{(2S)-2-methylbutyl}-3-piperidyl}methyl)amino-6-oxohexyl}-3,3,3-triphenylpropanamide. The title compound was obtained as a yellow oily substance.

$^1$H-NMR)CDCl$_3$, δppm): 0.98(3H, t, J=7.4 Hz), 1.01-1.78 (15H, m), 1.80-2.10(3H, m), 2.27(2H, t, J=7.5 Hz), 2.42-2.58 (1H, m), 2.89(2H, dd, J=5.9,12.0 Hz), 3.02-3.70 (10H, m), 3.56(2H, s), 3.76-3.90(1H, m), 5.03-5.12(1H, m), 7.17-7.35 (15H, m), 7.50-7.60(1H, m)

FAB-MS(m/e, as $(C_{40}H_{56}N_3O_2)^+$): 610

EXAMPLE 150

(3S)-1-ethyl-1-{(2S)-2-methylbutyl}-3-({(6-{(3,3,3-triphenylpropanoyl)amino}hexanoyl)amino}methyl) piperidinium chloride (Step 1)
Synthesis of N-(6-{((3S)-1-ethyl-3-piperidyl)methy}amino-6-oxohexyl)-3,3,3-triphenylpropanamide The title compound was prepared by a method similar to Example 27, using (3S)-3-aminomethyl-1-(t-butoxycarbonyl)-piperidine and acetaldehyde. The compound was obtained as a white solid.

$^1$H-NMR(CDCl$_3$, δppm): 0.90-1.16(8H, m), 1.43-1.80 (7H, m), 1.90(1H, t, J=10.8 Hz), 2.06(2H, t, J=7.4 Hz), 2.38 (2H, q, J=7.1 Hz), 2.77-2.85(2H, m), 2.86-2.96(2H, m), 3.10-3.20(2H, m), 3.56(2H, s), 4.80-4.90(1H, m), 5.62-5.72 (1H, m), 7.17-7.32(15H, m)

FAB-MS(m/e, as $(C_{35}H_{45}N_3O_2+H)^+$): 540

(Step 2)
Synthesis of (3S)-1-ethyl-1-{(2S)-2-methylbutyl}-3-({(6-{(3,3,3-triphenylpropanoyl)amino}hexanoyl)amino}methyl)-piperidinium chloride The title compound was prepared by a method similar to Example 129, using N-(6-{((3S)-1-ethyl-3-piperidyl)methyl}amino-6-oxohexyl)-3,3,3-triphenylpropanamide and (2S)-2-methylbutane iodide. The compound was obtained as a white foamy substance.

$^1$H-NMR)CDCl$_3$, δppm): 0.86-1.73(18H, m), 1.80-2.10 (3H, m), 2.20-2.37(2H, m), 2.39-2.56(1H, m), 2.87-2.95(2H, m), 3.08-3.70(10H, m), 3.56(2H, s), 3.87-4.05(1H, m), 5.18-5.28(1H, m), 7.14-7.38(15H, m), 8.40-8.58(1H, m)

FAB-MS(m/e, as $(C_{40}H_{56}N_3O_2)^+$): 610

EXAMPLE 151

(7R)-7-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-5-azoniaspiro [4.5]decane chloride The method of Japan Kokai (laid-open) No. Sho 62(1987)-215588 A1 was followed. In 0.6 ml of chloroform, 41 mg of(2R)-1-{(2S,4R)-4-hydroxy-1-(3,3,3-triphenylpropanoyl)pyrrolidin-2-yl)-carbonyl-N-((3S)-3-piperidylmethyl)pyrrolidine-2-carboxamide, 0.014 ml of diethylamine and 0.032 ml of 1,4-dibromobutane were dissolved, and the solution was allowed to stand in a hermetically sealed vessel for 6 days. The reaction liquid was diluted with chloroform and the solvent was distilled off under reduced pressure. The resultant residue was dissolved in a mixture of ultrapure water 0.6 ml/methanol 0.1 ml, and developed on a reversed phase medium pressure liquid chromatography [ODS-AQ 120-S50 (YMC). The product was purified and anion-exchanged by pouring 20 ml of saturated brine, washing with 150 ml of ultrapure water, and eluting from methanol/water=1/1, to provide 45 mg of the title compound as a white solid.

$^1$H-NMR(CDCl$_3$, δppm): 0.88(2H, t, J=6.8 Hz), 0.98-1.18 (1H, m), 1.21-1.34(3H, m), 1.65-2.38(12H, m), 2.52-2.68 (1H, m), 2.98-3.17(3H, m), 3.20-3.60(5H, m), 3.56 (1H, d, J=14.4 Hz), 3.70(1H, d, J=14.4 Hz), 3.79-3.95(2H, m), 3.96-4.04(1H, m), 4.37-4.41(1H, m), 4.51-4.60(2H, m), 7.17-7.39 (15H, m), 7.56(1H, t, J=6.0 Hz)

FAB-MS(m/e, as $(C_{41}H_{51}N_4O_4)^+$): 663

EXAMPLE 152

(7R)-7-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-5-azoniaspiro [4.5]dec-2-en chloride The title compound was prepared by a method similar to Example 151, using 1,4-dibromo-2-butene which was synthesized following the method of M. A. Keegstra, et al. [*Syn. Commun.* Vol. 21, 721-726 (1991)]. The compound was obtained as a white solid.

$^1$H-NMR)CDCl$_3$, δppm): 0.80-2.80(15H, m), 2.99-4.62 (16H, m), 5.80-6.00(2H, m), 7.15-7.68(16H, m)

ESI-MS(m/e, as $(C_{41}H_{49}N_4O_4)^+$): 661

EXAMPLE 153

(2R)-2-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-6-azoniaspiro [5.5]undecane chloride The title compound was prepared by a method similar to Example 151, using 1,5-dibromopentane. The compound was obtained as a white solid.

$^1$H-NMR(CDCl$_3$, δppm): 0.88(2H, t, J=6.6 Hz), 0.98-1.13 (1H, m), 1.20-1.36(3H, m), 1.68-2.07(10H, m), 2.08-2.32 (3H, m), 2.40-2.52(1H, m), 2.80-2.95(1H, m), 3.04-3.20(2H, m), 3.22-3.80(7H, m), 3.57(1H, d, J=15.3 Hz), 3.68 (1H, d, J=15.3 Hz), 3.88-3.96(1H, m), 4.07-4.16 (1H, m),4.38-4.43 (1H, m), 4.56-4.68(2H, m), 7.17-7.39 (15H, m), 7. 64(1H, t, J=6.5 Hz)

FAB-MS(m/e, as $(C42H_{53}N_4O_4)^+$): 677

EXAMPLE 154

(2R)-2-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-9,9-dimethyl-6-azoniasiro[5.51]undecane chloride The title compound was prepared by a method similar to Example 151, using 1,5-dibromo-3,3-dimethylpentane. The compound was obtained as a white solid.

$^1$H-NMR(CDCl$_3$, δppm): 0.80-2.33(18H, m), 1.09(3H, s), 1.24(3H, s), 2.60-3.92(12H, m), 3.52(1H, d, J=14.5 Hz), 3.68 (1H, d, J=14.5 Hz), 4.26-4.56(3H, m), 7.15-7.66(16H, m)

FAB-MS(m/e, as $(C_{44}H_{57}N_4O_4)^+$): 705

EXAMPLE 155

(8R)-8-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-3-oxa-6-azoniaspiro[5.5]undecane chloride The title compound was prepared by a method similar to Example 151, using 2,2'-dichlorodiethyl ether. The compound was obtained as a white solid.

$^1$H-NMR)CDCl$_3$, δppm): 0.80-2.78(17H, m), 2.95-4.51 (18H, m), 7.12-7.78(16H, m)

ESI-MS(m/e, as (C$_{41}$H$_{51}$N$_4$O$_5$)$^+$): 679

EXAMPLE 156

(7R)-2,3-epoxy-7-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-5-azoniaspiro[4.51]decane chloride The title compound was prepared by a method similar to Example 151, using 1,4-dibromo-2,3-epoxybutane (cf. Referential Example 10). The compound was obtained as a white solid.

$^1$H-NMR(CDCl$_3$, δppm): 0.80-2.50(17H, m), 2.60-4.85 (16H, m), 7.10-7.45(15H, m), 7.58-7.80(1H, m)

ESI-MS(m/e, as (C$_{41}$H$_{49}$N$_4$O$_5$)$^+$): 677

EXAMPLE 157

3-({({(2R)-1-({(2S,4R)-4-hydroxy-1-(3,3,3-triphenylpropanoyl)-2-pyrrolidinyl}carbonyl)-2-pyrrolidinyl}carbonyl)amino}methyl)-1,1-dimethylpyrrolidinium bromide (Step 1)

Synthesis of (2R)-1-{(2S,4R)-4-hydroxy-1-(3,3,3-triphenylpropanoyl)pyrrolidin-2-yl}carbonyl-N-(3-pyrrolidylmethyl)pyrrolidine-2-carboxamide The title compound was prepared by successively conducting procedures similar to Step 5 of Example 1 and Example 46, using 3-aminomethyl-1-(t-butoxycarbonyl)pyrrolidine [which was synthesized by a method similar to the one described in Japan Kokai Hei 11(1999)-193232, using 3-hydroxymethyl-1-benzylpyrrolidine [taught in Japan Kokai (laid-open) Hei 4(1992)-112868]] and (2R)-1-{(2S,4R)-4-(tert-butoxy)-1-(3,3,3-triphenylpropanoyl)pyrrolidin-2-yl}carbonyl-pyrrolidine-2-carboxylic acid.

$^1$H-NMR(CDCl$_3$, δppm): 0.80-2.34(9H, m), 2.49-2.64 (1H, m), 2.67-2.81(1H, m), 2.82-3.29(7H, m), 3.30-3.42(1H, m), 3.43-3.65(2H, m), 3.70-3.90(2H, m), 4.29-4.43(2H, m), 4.49-4.61(1H, m), 7.13-7.57(16H, m)

ESI-MS(m/e, as (C$_{36}$H$_{42}$N$_4$O$_4$+H)$^+$): 595

(Step 2)

Synthesis of (2R)-1-{(2S,4R)-4-hydroxy-1-(3,3,3-triphenylpropanoyl)pyrrolidin-2-yl}carbonyl-N-{(1-methyl-3-pyrrolidyl)methyl}pyrrolidine-2-carboxamide The title compound was prepared by a method similar to Example 48, using (2R)-1-{(2S,4R)-4-hydroxy-1-(3,3,3-triphenylpropanoyl)pyrrolidin-2-yl}carbonyl-N-(3-pyrrolidylmethyl)pyrrolidine-2-carboxamide. $^1$H-NMR(CDCl$_3$, δppm): 0.83-2.12(9H, m), 2.20-2.46(3H, m), 2.31(3H, s), 2.49-2.83(4H, m), 3.10-3.27(1H, m), 3.29-3.40 (1H, m), 3.42 (1H, d, J=14.5 Hz), 3.56-3.62(1H, m), 3.77-3.85(1H, m), 3.87(1H, d, J=14.5 Hz), 4.30-4.39(2H, m), 4.52-4.59(1H, m), 7.15-7.39(16H, m)

ESI-MS(m/e, as (C$_{37}$H$_{44}$N$_4$O$_4$+H)$^+$): 609

(Step 3)

Synthesis of 3-({({(2R)-1-({(2S,4R)-4-hydroxy-1-(3,3,3-triphenylpropanoyl)-2-pyrrolidinyl}carbonyl)-2-pyrrolidinyl}-carbonyl)amino}methyl)-1,1-dimethylpyrrolidinium bromide The title compound was prepared by a method similar to Example 130, using (2R)-1-{(2S,4R)-4-hydroxy-1-(3,3,3-triphenylpropanoyl)pyrrolidin-2-yl}carbonyl-N-{(1-methyl-3-pyrrolidyl)methyl}pyrrolidine-2-carboxamide. The compound was obtained as a colorless oily substance.

$^1$H-NMR(CDCl$_3$, δppm): 0.82-2.35(9H, m), 2.52-2.70 (1H, m), 2.72-2.89(1H, m), 3.00-3.89(18H, m), 4.25-4.60 (2H, m), 7.10-7.40(15H, m), 7.48-7.78(1H, m)

ESI-MS(m/e, as (C$_{38}$H$_{47}$N$_4$O$_4$)$^+$): 623

Referential Example 1

(3R)-3-aminomethyl-1-(tert-butoxycarbonyl)piperidine (Step 1)

Synthesis of ethyl (3S)-3-piperidinecarboxylate

To 13.0 g of ethyl (3S)-3-piperidinecarboxylate D(−)-tartarate which was synthesized following the method of P. Magnus, et al. [*J. Org. Chem.* Vol. 56, 1166-1170 (1991)], 3N aqueous sodium hydroxide solution was added to render the former basic, followed by extraction with chloroform and drying over anhydrous magnesium sulfate. Distilling the solvent off under reduced pressure, 7.50 g of the title compound was obtained.

(Step 2)

Synthesis of (3S)-3-piperidylmethanol

To solution of 7.50 g of ethyl (3S)-3-piperidinecarboxylate in 200 ml of tetrahydrofuran, 3.4 g of lithium aluminium hydrate was added under cooling with ice, followed by an hour's refluxing under heating. To the reaction liquid sodium sulfate decahydrate was added under cooling with ice, followed by 12 hours' stirring at room temperature and filtration through cerite. Distilling the filtrate off under reduced pressure, 5.89 g of the title compound was obtained.

(Step 3)

Synthesis of {(3S)-1-(tert-butoxycarbonyl)-3-piperidyl}methanol

To a solution of 5.89 g of (3S)-3-piperidylmethanol in 150 ml of chloroform, another solution of 9.3 g of di-tert-butyl dicarbonate in 50 ml of chloroform was added under cooling with ice, followed by 15 hours' stirring at room temperature. The reaction liquid was distilled off under reduced pressure, diluted with diethyl ether, washed successively with 0.5 N hydrochloric acid, water and saturated brine, and dried over anhydrous magnesium sulfate. Distilling the solvent off under reduced pressure, 8.01 g of the title compound was obtained.

(Step 4)

Synthesis of {(3S)-1-(tert-butoxycarbonyl)-3-piperidyl}methyl methanesulfonate

To a solution of 7.96 g of {(3S)-1-(tert-butoxycarbonyl)-3-piperidyl}methanol in 150 ml of chloroform, 3.4 ml of methanesulfonyl chloride and 6.7 ml of triethylamine were added under cooling with ice, followed by an hour's stirring at room temperature. The reaction liquid was distilled off under reduced pressure, diluted with ethyl acetate and saturated aqueous sodium bicarbonate solution was added, followed by 1.5 hours' stirring. Thereafter the reaction liquid was successively washed with water and saturated brine and dried over anhydrous magnesium sulfate. Distilling the solvent off, 10.50 g of the title compound was obtained.

(Step 5)

Synthesis of (3S)-3-azidomethyl-1-(tert-butoxycarbonyl)piperidine

To a solution of 10.50 of {(3S)-1-(tert-butoxycarbonyl)-3-piperidyl}methyl methanesulfonate in 100 ml of N,N-dimethylformamide, 4.9 g of sodium azide was added at room temperature, followed by 4 hours' stirring at 80° C. under heating. The reaction liquid was diluted with ethyl acetate, washed successively with water and saturated brine, and dried over anhydrous magnesium sulfate. The solvent was distilled off under reduced pressure, and resulting residue was purified by means of silica gel column chromatography (eluting solvent: from hexane to hexane/ethyl acetate=15/1) to provide 7.24 g of the title compound.

(Step 6)

Synthesis of (3R)-3-aminomethyl-1-(tert-butoxycarbonyl)piperidine

To a solution of 600 mg of (3S)-3-azidomethyl-1-(tert-butoxycarbonyl)piperidine in 12.5 ml of 20% hydrous tetrahydrofuran, 622 mg of triphenylphosphine was added at room temperature, followed by 45 minutes' refluxing under heating. The reaction liquid was rendered acidic by addition of 0.5 N hydrochloric acid, and successively washed with chloroform and ethyl acetate. Then 4N aqueous sodium hydroxide solution was added to the aqueous layer to render the latter basic, followed by extraction with chloroform and drying over anhydrous sodium sulfate. Distilling the solvent off under reduced pressure, 497 mg of the title compound was obtained.

Referential Example 2

(3R)-3-aminomethyl-1-(cyclohexylmethyl)piperidine (Step 1)

Synthesis of ((3S)-1-cyclohexylmethyl-3-piperidyl)methanol

To a solution of 900 mg of (3S)-3-piperidylmethanol in 60 ml of tetrahydrofuran, 1.05 g of cyclohexanecarbaldehyde, 0.54 ml of acetic acid and 2.5 g of sodium triacetoxyborohydrate were successively added at room temperature by the order stated, followed by 21 hours' stirring at the same temperature. The reaction liquid was rendered acidic with 1N hydrochloric acid and washed with chloroform. The aqueous layer was rendered basic with 4N aqueous sodium hydroxide solution, followed by extraction with chloroform and drying over anhydrous sodium sulfate. Distilling the solvent off under reduced pressure, 990 mg of the title compound was obtained.

(Step 2)

Synthesis of (3R)-3-aminomethyl-1-(cyclohexylmethyl)piperidine

The title compound was prepared by procedures similar to Steps 4-6 of Referential Example 1, using ((3S)-1-cyclohexylmethyl-3-piperidyl)methanol.

Referential Example 3

(3S)-3-aminomethyl-1-(tert-butoxycarbonyl)piperidine

The title compound was prepared by a method similar to Referential Example 1, using ethyl (3R)-3-piperidinecarboxylate L$^{(+)}$-tartarate which was synthesized following the method of P. Magnus, et al. [*J. Ore. Chem.*, Vol. 56, pp. 1166-1170 (1991)].

Referential Example 4

3-Aminomethyl-1-(tert-butoxycarbonyl)piperidine

The title compound was prepared by procedures similar to Steps 2-6 of Referential Example 1, using ethyl 3-piperidinecarboxylate.

Referential Example 5

3-Aminomethyl-1-(cyclohexylmethyl)piperidine

The title compound was prepared by successively conducting procedures similar to Step 2 of Referential Example 1 and Referential Example 2, using ethyl 3-piperidinecarboxylate.

Referential Example 6

3,3,3-Tris(4-fluorophenyl)propionic acid

The synthesis was conducted referring to the method of Fan Benlun, et al. [*Yiyao Gongye*, Vol.9, pp. 2-4 (1983)]. In 1.1 ml of acetic acid, 1.0 g of 3,3,3-tris (4-fluorophenyl)methanol was suspended. To the suspension 541 mg of cyanoacetic acid and 230 mg of zinc chloride were added at room temperature, followed by 4 hours' stirring at 130° C. under heating. The reaction liquid was cooled to room temperature, and 1.8 ml of conc. sulfuric acid and 0.64 ml of acetic anhydride were added, followed by 17 hours' stirring at 130° C. under heating. The reaction liquid was cooled to room temperature, diluted with water and filtered. The filter cake was thoroughly washed with water to provide 940 mg of the title compound.

Referential Example 7

Cyclopentylmethyl methanesulfonate

The title compound was synthesized by a method similar to Step 4 of Referential Example 1, using cyclopentylmethanol.

Referential Example 8

2-(1-Methylcyclopropane-1-yl)acetaldehyde (Step 1)

Synthesis of 1-methylcyclopropane-1-carbaldehyde

To a solution of 0.5 ml of 2-cyclopropanepropanol in 6 ml of dimethyl sulfoxide, 3 ml of triethylamine and a solution of 2.5 g of sulfur trioxide-pyridine complex in 4 ml of dimethyl sulfoxide were successively added at room temperature, followed by 4.5 hours' stirring at the same temperature. The reaction solution was poured into water, extracted with diethyl ether, and the organic layer was washed with water and dried over anhydrous magnesium sulfate. Distilling the solvent off under reduced pressure, about 10 ml of a diethyl ether solution of the title compound was obtained.

(Step 2)

Synthesis of 2-(1-methylcyclopropane-1-yl)acetaldehyde

Methoxymethyltriphenylphosphonium chloride 2.57 g was suspended in 40 ml of diethyl ether, and to the suspension n-butyl lithium (1.47 M hexane solution, 8.0 ml) was added under cooling with ice, followed by 2 hours' stirring at room temperature. Then 10 ml of a diethyl ether solution of 1-methylcyclopropane-1-carbaldehyde was added at room temperature, followed by an hour's stirring at the same temperature. The reaction solution was poured into water, extracted with diethyl ether, and the organic layer was washed with water and dried over anhydrous magnesium sulfate. The solvent was distilled off under slightly reduced pressure, and the resultant residue was dissolved in 10 ml of tetrahydrofuran. To the solution 10 ml of conc. hydrochloric acid and 5 ml of water were added at room temperature, followed by 12 hours' stirring at the same temperature. The reaction solution was poured into water, extracted with diethyl ether, and the organic layer was washed with water and dried over anhydrous magnesium sulfate. Distilling the solvent off under reduced pressure, about 15 ml of a diethyl ether solution of the title compound was obtained.

Referential Example 9

1-(Cyclopentyl)ethyl 4-methylbenzenesulfonate

To 0.9 ml of a pyridine solution of 1-cyclopentaneethanol, 309 mg of 4-methylbenzenesulfonyl chloride was added under cooling with ice, followed by 6.5 hours' stirring at room temperature. A hydrochloric acid solution was added under cooling with ice to render the reaction liquid acidic, followed by extraction with ethyl acetate. The organic solvent layer was washed with saturated brine and dried over anhydrous sodium sulfate. Distilling the solvent off under reduced pressure, 324 mg of the title compound was obtained.

Referential Example 10

Preparation of 1,4-dibromo-2,3-epoxybutane

To a solution of 500 mg of 1,4-dibromo-2-butene in 1 ml of chloroform, 485 mg of meta-chloroperbenzoic acid was added under cooling with ice, followed by 20 hours' stirring at room temperature. Further 606 mg of meta-chloroperbenzoic acid was added, followed by 3 days' stirring. The reaction liquid was then poured into a mixed aqueous solution of sodium hydrogencarbonate and sodium thiosulfate, extracted with chloroform and dried over anhydrous sodium sulfate. Distilling the solvent off under reduced pressure, 512 mg of the title compound was obtained.

INDUSTRIAL APPLICABILITY

Because those compounds of the present invention exhibit selective antagnism to muscarinic $M_3$ receptors, they are useful as safe and effective treating agents of diseases of the respiratory, urinary or digestive systems, exhibiting little side effect.

The invention claimed is:

1. Compounds which are represented by the following general formula (I)

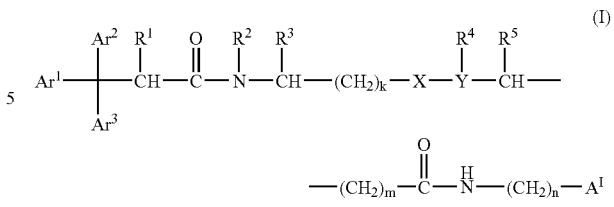

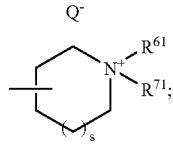

in which A stands for a group of the following formula ($b_0$)

$Ar^1$, $Ar^2$ and $Ar^3$ each independently stands for optionally substituted phenyl, the substituent being selected from the group consisting of halogen, hydroxyl, lower alkyl, lower alkenyl, lower alkoxy, carbamoyl, lower alkylcarbamoyl and di-lower alkylcarbamoyl; k means 0 or 1; m, n and s each independently means 0, 1 or 2; $R^1$ stands for hydrogen or optionally substituted lower alkyl, the substituent being selected from the group consisting of hydroxyl, amino, carbamoyl, lower alkylcarbamoyl, di-lower alkylcarbamoyl and imidazolyl; $R^2$, $R^3$, $R^4$ and $R^5$ each independently stands for hydrogen or optionally substituted lower alkyl, the substituent being selected from the group consisting of hydroxyl, amino, carbamoyl, lower alkylcarbamoyl, di-lower alkylcarbamoyl and imidazolyl, or $R^2$ and $R^3$, or $R^4$ and $R^5$, may together stand for, independently of each other, optionally substituted trimethylene, the substituent being selected from the group consisting of oxo, hydroxyl, amino, lower alkoxy, lower alkanoyloxy, lower alkylamino, di-lower alkylamino, (imino-lower alkyl)amino, lower alkanoylamino, lower alkoxycarbonylamino, (lower alkylcarbamoyl)amino, lower alkylsulfonylamino, guanidino, lower alkoxycarbonyl, carbamoyl, lower alkylcarbamoyl, di-lower alkylcarbamoyl, imidazolyl and a group represented by —$R^7$, $R^7$ standing for optionally substituted lower alkyl, the substituent being selected from the group consisting of hydroxyl, amino, carbamoyl, lower alkylcarbamoyl, di-lower alkylcarbamoyl, lower alkoxycarbonyl and imidazolyl; $R^{61}$ and $R^{71}$ each independently stands for $C_1$-$C_{10}$ alkyl, lower alkenyl, cycloalkyl, cycloalkyl-lower alkyl whose ring portion may be substituted with lower alkyl, cycloalkenyl-lower alkyl or aralkyl, X stands for carbonyl or methylene; Y stands for nitrogen or methine; and $Q^-$ stands for anion or salts thereof.

2. The compounds according to claim 1 in which $R^{61}$ and $R^{71}$ each independently is $C_1$-$C_{10}$ alkyl, lower alkenyl or cycloalkyl-lower alkyl whose ring portion may be substituted with lower alkyl.

3. The compounds according to claim 2, in which $R^{61}$ and $R^{71}$ each independently is $C_1$-$C_6$ alkyl.

4. The compounds according to claim 3, in which $R^{61}$ and $R^{71}$ each independently is methyl, ethyl, propyl or 2-methylbutyl.

5. The compounds according to claim 2, in which both $R^{61}$ and $R^{71}$ are 2-propenyl or cyclopropylmethyl; or $R^{61}$ is cyclohexylmethyl and $R^{71}$ is methyl.

6. The compounds according to claim 1, in which $Ar^1$, $Ar^2$ and $Ar^3$ each independently stands for phenyl which is optionally substituted with halogen or lower alkyl; n is 1 or 2; s is 1; and $R^1$ is hydrogen.

7. Compounds which are represented by the general formula (1-a):

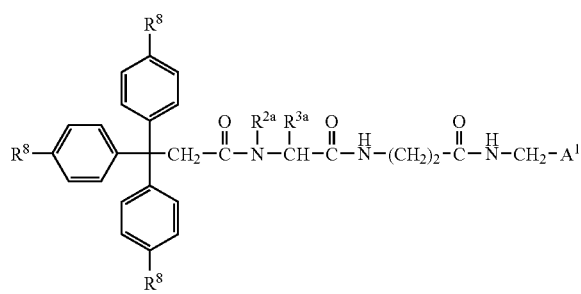

wherein $A^1$ stands for a group represented by the formula ($b_1$),

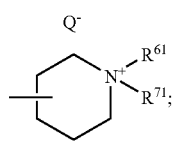

$R^{2a}$ and $R^{3a}$ each independently stands for hydrogen, or optionally substituted lower alkyl, the substituent being selected from hydroxyl, amino, carbamoyl, lower alkylcarbamoyl, di-lower alkylcarbamoyl and imidazolyl; $R^8$ stands for hydrogen, halogen or lower alkyl; $R^{61}$ and $R^{71}$ each independently stands for $C_1$-$C_{10}$ alkyl, lower alkenyl, cycloalkyl, cycloalkyl-lower alkyl whose ring portion may be substituted with lower alkyl, cycloalkenyl-lower alkyl or aralkyl, and $Q^-$ stands for anion.

8. Compounds which are represented by the general formula (1-c):

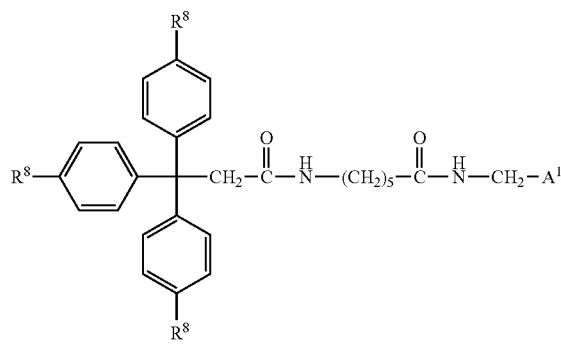

in which $A^1$ stands for a group represented by the formula ($b_1$),

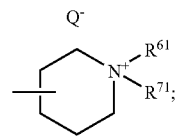

$R^8$ stands for hydrogen, halogen, or lower alkyl; $R^{61}$ and $R^{71}$ each independently stands for $C_1$-$C_{10}$ alkyl, lower alkenyl, cycloalkyl, cycloalkyl-lower alkyl whose ring portion may be substituted with lower alkyl, cycloalkenyl-lower alkyl or aralkyl, and $Q^-$ stands for anion.

9. The compounds according to claim 6, which are represented by the general formula (1-e):

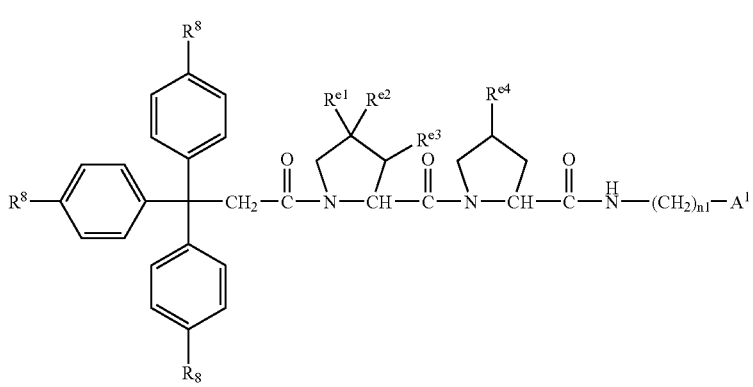

in which $A^1$ stands for a group represented by the formula $(b_1)$,

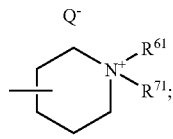

$(b_1)$ n1 stands for 1 or 2; $R^{e1}$, $R^{e2}$, $R^{e3}$ and $R^{e4}$ each independently stands for hydrogen, hydroxyl, amino, lower alkoxy, lower alkanoyloxy, lower alkylamino, di-lower alkylamino, (imino-lower alkyl)amino, lower alkanoylamino, lower alkoxycarbonylamino, (lower alkylcarbamoyl)amino, lower alkylsulfonylamino, guanidino, lower alkoxycarbonyl, carbamoyl, lower alkylcarbamoyl, di-lower alkylcarbamoyl, imidazolyl and a group represented by —$R^7$; or $R^{e1}$ and $R^{e2}$ together signify oxo group; $R^7$ stands for optionally substituted lower alkyl, the substituent being selected from the group consisting of hydroxyl, amino, carbamoyl, lower alkylcarbamoyl, di-lower alkylcarbamoyl, lower alkoxycarbonyl and imidazolyl; $R^8$ stands for hydrogen, halogen or lower alkyl; $R^{61}$ and $R^{71}$ each independently stands for $C_1$-$C_{10}$ alkyl, lower alkenyl, cycloalkyl, cycloalkyl-lower alkyl whose ring portion may be substituted with lower alkyl, cycloalkenyl-lower alkyl or aralkyl, and $Q^-$ stands for anion.

10. The compounds according to claim 9, in which $R^{e1}$ is hydrogen or hydroxyl, and all of $R^{e2}$, $R^{e3}$ and $R^{e4}$ are hydrogen.

11. The compounds according to claim 9, in which $R^{61}$ and $R^{71}$ each independently is $C_1$-$C_{10}$ alkyl, lower alkenyl or cycloalkyl-lower alkyl whose ring portion may be substituted with lower alkyl.

12. The compounds according to claim 11, in which $R^{61}$ and $R^{71}$ each independently is $C_1$-$C_6$ alkyl.

13. The compounds according to claim 12, in which $R^{61}$ and $R^{71}$ each independently is methyl, ethyl, propyl or 2-methylbutyl.

14. The compounds according to claim 11, in which both $R^{61}$ and $R^{71}$ are 2-propenyl or cyclopropylmethyl; or $R^{61}$ is cyclohexylmethyl and $R^{71}$ is methyl.

* * * * *